(12) United States Patent
Amano et al.

(10) Patent No.: US 7,465,274 B2
(45) Date of Patent: Dec. 16, 2008

(54) DIAGNOSTIC APPARATUS FOR ANALYZING ARTERIAL PULSE WAVES

(75) Inventors: Kazuhiko Amano, Suwa (JP); Hiroshi Kasahara, Kashiwa (JP); Hitoshi Ishiyama, Toride (JP); Kazuo Kodama, Yokohama (JP)

(73) Assignee: Seiko Epson Corporation, Tokyo (JP)

( * ) Notice: Subject to any disclaimer, the term of this patent is extended or adjusted under 35 U.S.C. 154(b) by 958 days.

(21) Appl. No.: 10/869,587

(22) Filed: Jun. 16, 2004

(65) Prior Publication Data

US 2004/0267141 A1  Dec. 30, 2004

Related U.S. Application Data

(62) Division of application No. 10/002,823, filed on Nov. 1, 2001, now Pat. No. 6,767,329, which is a division of application No. 09/587,050, filed on Jun. 2, 2000, now Pat. No. 6,364,842, which is a division of application No. 08/302,705, filed as application No. PCT/JP94/00011 on Jan. 7, 1994, now Pat. No. 6,261,235.

(30) Foreign Application Priority Data

| Jan. 7, 1993 | (JP) | ................................... 5-001431 |
| Mar. 8, 1993 | (JP) | ................................... 5-046826 |
| Mar. 11, 1993 | (JP) | ................................... 5-051072 |
| Aug. 9, 1993 | (JP) | ................................... 5-197569 |
| Nov. 19, 1993 | (JP) | ................................... 5-291052 |
| Nov. 30, 1993 | (JP) | ................................... 5-300549 |

(51) Int. Cl.
*A61B 5/00* (2006.01)

(52) U.S. Cl. ...................................... 600/500; 600/485
(58) Field of Classification Search ....................... None
See application file for complete search history.

(56) References Cited

U.S. PATENT DOCUMENTS

| 4,331,154 A | | 5/1982 | Broadwater et al. |
| 4,368,256 A | | 1/1983 | Mollet et al. |
| 4,510,944 A | | 4/1985 | Porges |
| 4,731,726 A | | 3/1988 | Allen, III |
| 4,770,184 A | | 9/1988 | Greene, Jr. et al. |
| 4,993,420 A | | 2/1991 | Welkowitz et al. |
| 5,000,188 A | * | 3/1991 | Kojima ........................ 600/500 |
| 5,267,568 A | * | 12/1993 | Takara ........................ 600/500 |
| 5,274,548 A | | 12/1993 | Bernard et al. |
| 5,316,004 A | | 5/1994 | Chesney et al. |

(Continued)

FOREIGN PATENT DOCUMENTS

CN  86 1 07766 A  5/1988

(Continued)

OTHER PUBLICATIONS

"*Visualization and Quantitative Analysis of The Pulse Diagnosis in Ayurveda*" Kazuo Kodama, Hitoshi Ishiyama, Hiroshi Kazahara, B1 center of the Kitasato Institute, Tokyo., Tokyo Denki Univ., Tokyo, Japan, pp. 1-20.

*Primary Examiner*—Robert L Nasser
(74) *Attorney, Agent, or Firm*—Mark P. Watson

(57) ABSTRACT

A pulse waveform of a living body is detected and is analyzed using peak point data or timing data to perform a diagnosis of a condition of the body.

20 Claims, 37 Drawing Sheets

U.S. PATENT DOCUMENTS

| | | | |
|---|---|---|---|
| 5,339,818 A | 8/1994 | Baker et al. | |
| 5,365,930 A | 11/1994 | Takashima et al. | |
| 5,381,797 A | 1/1995 | Pak et al. | |
| 5,388,585 A | 2/1995 | Tomita | |
| 5,390,679 A | 2/1995 | Martin | |
| 5,406,952 A * | 4/1995 | Barnes et al. | 600/485 |
| 5,415,167 A | 5/1995 | Wilk | |
| 5,431,170 A | 7/1995 | Mathews | |
| 5,492,127 A | 2/1996 | Chul | |
| 5,582,179 A | 12/1996 | Shimizu et al. | |
| 5,730,137 A | 3/1998 | Amano et al. | |
| 5,730,138 A | 3/1998 | Wang | |

FOREIGN PATENT DOCUMENTS

| | | |
|---|---|---|
| JP | 55-34820 | 8/1978 |
| JP | 56-43927 | 4/1981 |
| JP | 57-52054 | 3/1982 |
| JP | 61-162932 | 7/1986 |
| JP | 63-147433 | 6/1988 |
| JP | 64-27534 | 1/1989 |
| JP | 01027534 | 1/1989 |
| JP | 1-94825 | 4/1989 |
| JP | 2-4300 | 1/1990 |
| JP | 2-196334 | 8/1990 |
| JP | 3-15439 | 1/1991 |
| JP | 3-66357 | 3/1991 |
| JP | 4-9139 | 1/1992 |
| JP | 4-15037 | 1/1992 |
| JP | 4-28338 | 1/1992 |
| JP | 4-33638 | 2/1992 |
| JP | 4-108424 | 4/1992 |
| JP | 4-208136 | 7/1992 |
| JP | 4-506160 | 10/1992 |
| JP | 4-338460 | 11/1992 |
| WO | WO 90/14042 | 11/1990 |

* cited by examiner

PULSE WAVES AT V POINT (VATA POINT: 2rd FINGER)

PULSE WAVES AT P POINT (PITTA POINT: 3rd FINGER)

PULSE WAVES AT K POINT (KAPHA POINT: 4rd FINGER)

PULSE WAVES AT V POINT (VATA POINT: 2rd FINGER)

PULSE WAVES AT P POINT (PITTA POINT: 3rd FINGER)

PULSE WAVES AT K POINT (KAPHA POINT: 4rd FINGER)

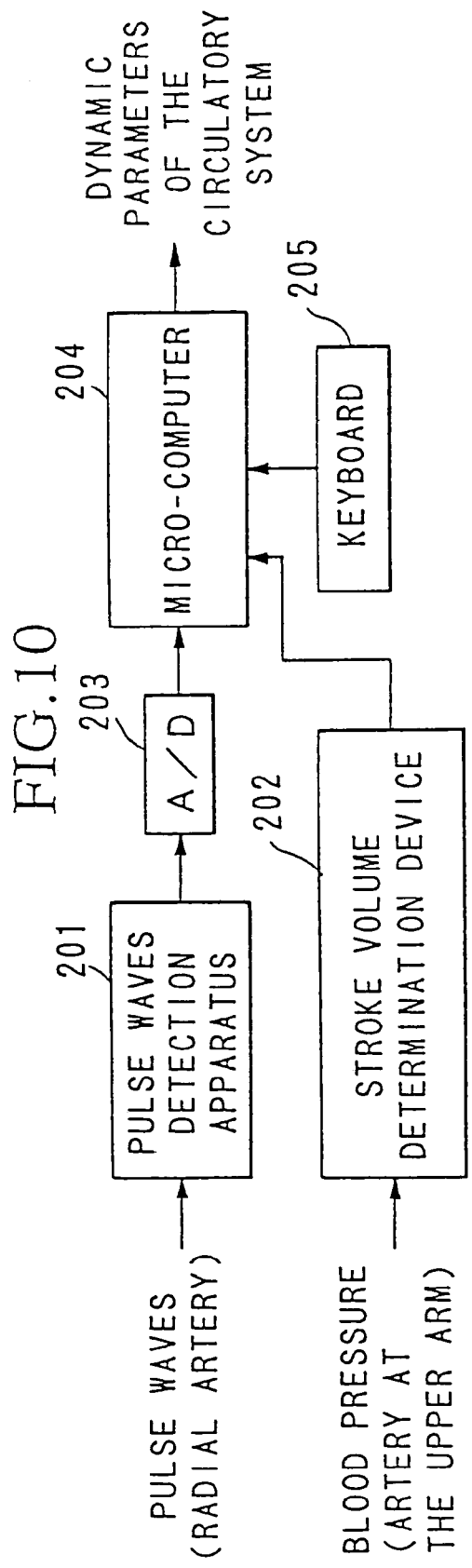
FIG.10
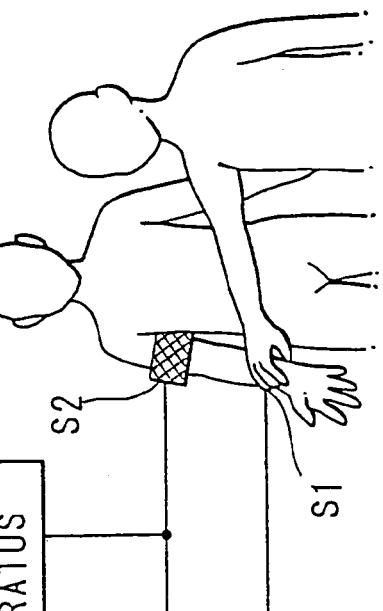
FIG.11
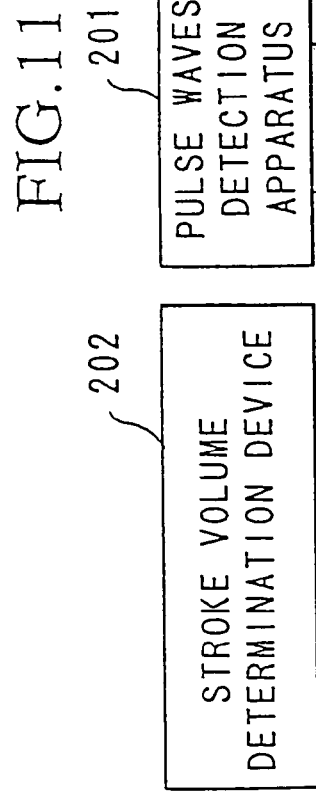

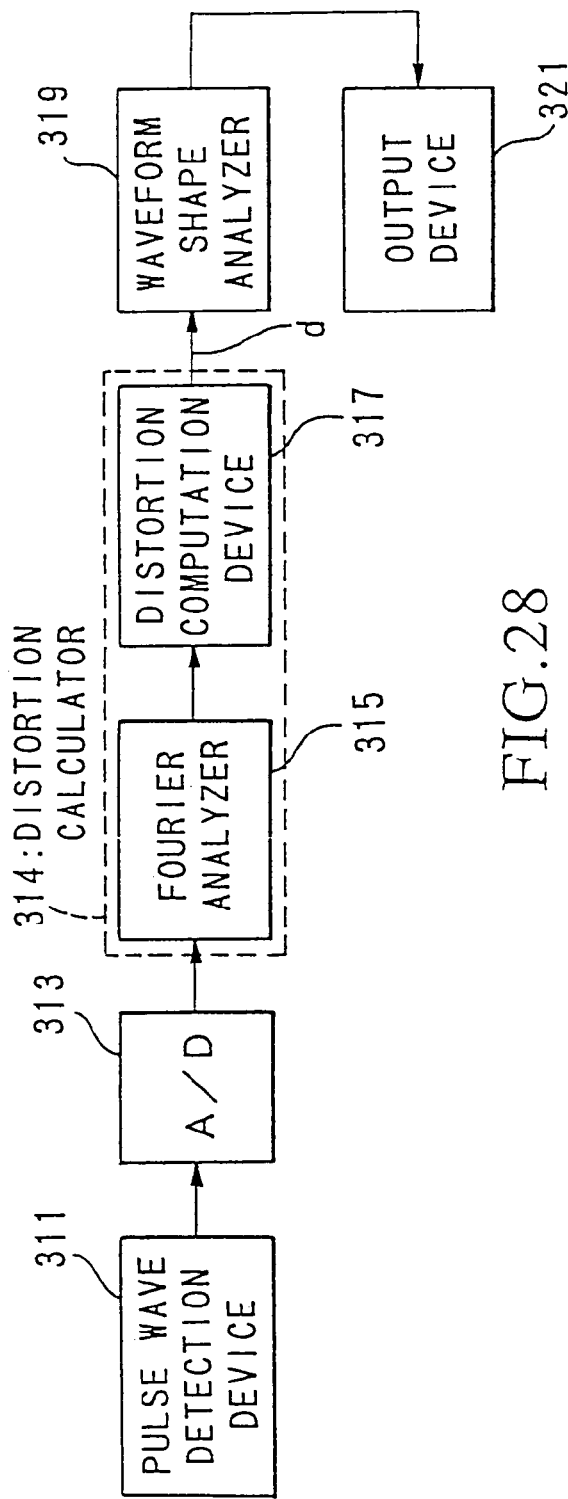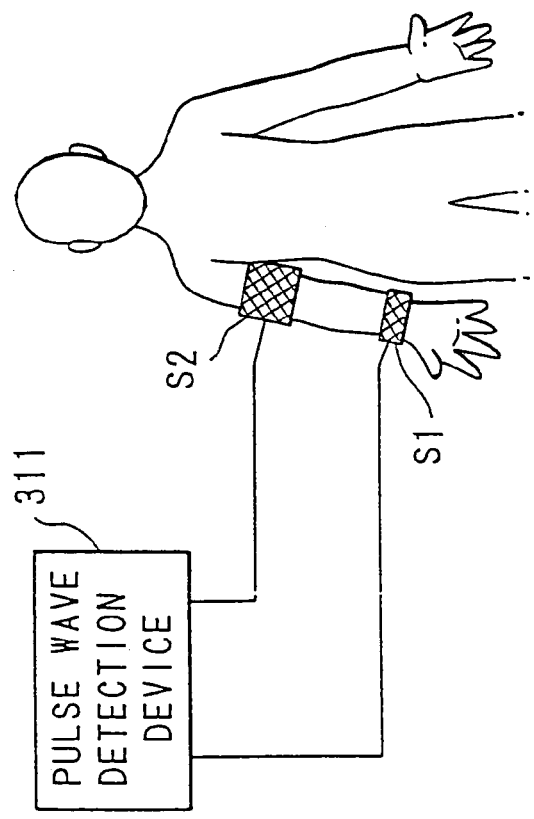

FIG.43

<PSYCHOMATIC FATIGUE LEVEL DIAGNOSTIC QUESTIONNAIRE>

I WILL ASK THE FOLLOWING CONCERNING YOUR RECENT BODY AND MIND CONDITION. CIRCLE THE APPROPRIATE PLACE.

|   | 0 | 1 | 2 | 3 |
|---|---|---|---|---|
| 1 CANNOT SLEEP AT NIGHT | (NEVER | SOMETIMES | OFTEN | ALWAYS) |
| 2 PALPITATIONS OF HEART | (NEVER | SOMETIMES | OFTEN | ALWAYS) |
| 3 EASILY TIRED /FEEL TIRED | (NEVER | SOMETIMES | OFTEN | ALWAYS) |
| 4 HEAD ACHE | (NEVER | SOMETIMES | OFTEN | ALWAYS) |
| 5 HANDS /FEET NUMB | (NEVER | SOMETIMES | OFTEN | ALWAYS) |
| 6 COLD SWEAT | (NEVER | SOMETIMES | OFTEN | ALWAYS) |
| 7 FEEL LIKE CATCHING COLD | (NEVER | SOMETIMES | OFTEN | ALWAYS) |
| 8 CHEST PAIN/UNCOMFORTABLE AROUND CHEST | (NEVER | SOMETIMES | OFTEN | ALWAYS) |
| 9 PAINFUL TO WORK | (NEVER | SOMETIMES | OFTEN | ALWAYS) |

TOTAL POINTS( )

TOTAL SORE IS PSYCHOMATIC FATIGUE LEVEL.

| PEAK ADDRESS | ADR3 | 0 | 1 | 2 | 3 | 4 |
|---|---|---|---|---|---|---|
| WAVEFORM VALVE ADDRESS | ADR1 | | | | | |
| WAVEFORM CLASSIFICATION | B/T | | | | | |
| WAVEFORM VALVE | W | | | | | |
| STROKE | STRK | | | | | |
| SLOPE INFORMATION | SLP | | | | | |

PEAK INFORMATION { (rows: WAVEFORM VALVE ADDRESS, WAVEFORM CLASSIFICATION, WAVEFORM VALVE, STROKE, SLOPE INFORMATION)

DIAGNOSTIC APPARATUS FOR ANALYZING ARTERIAL PULSE WAVES

CONTINUING APPLICATION DATA

This application is a divisional of 10/002,823 file Nov. 1, 2001, which is a divisional of Ser. No. 09/587,050 filed Jun. 2, 2000, now U.S. Pat. No. 6,364,842, which is a divisional of Ser. No. 08/302,705 file Dec. 5, 1994, now U.S. Pat. No 6,261,235 which is a 371 of PCT/JP94/00011, filed Jan. 7, 1994. The contents of each of these prior applications is incorporated herein by reference in their entirety.

BACKGROUND OF THE INVENTION

1. Technical Field

The present invention relates to a diagnostic apparatus for performing diagnostics based on parameters and data obtained from the pulse waves generated by a living body, and to a pulse wave analyzing apparatus for generating the parameters and data representing the pulse waves of the living body.

2. Background Art

The traditional medicine, for example, the Chinese medicine has long practiced pulse taking at three locations (Chun, Guan, and Chi) on an arm along the radial artery. Also, there is a method for taking pulses automatically with three piezoelectric elements which are respectively pressed at the three points. (Japanese Patent Application (JPA), Second Publication, S57-52054). Further, to equalize the finger pressure at the piezoelectric elements, it is known that air pressure is used to press down the piezoelectric elements (JPA, First Publication, H04-9139).

On the other hand, a technique called Ayurveda has been known in traditional Indian medicine from ancient times. This method will be explained with reference to FIGS. 3A and 3B.

An examiner places his fingers lightly on three locations along the radial artery of an examinee. The three locations shown in FIG. 3A are referred to as Vata (V), Pitta (P) and Kapha (K), and correspond roughly to the three locations in the Chinese Medicine known as the Chun, Guan and Chi. The examiner places his second finger on Vata (V), his third finger on Pitta (P) and his fourth finger on Kapha (K), and checks the pulsing motions at the variant depths.

Next, the examiner performs a diagnostic analysis of the health condition of the examinee based on the sections and strength of the examinee's pulse felt at the four points on his one finger as illustrated in FIG. 3B. It follows, therefore, that with the three fingers, he can perform the diagnostic analysis based on a total of twelve points.

Such wrist pulse method and the Ayurveda technique are said to provide excellent diagnostics, but because these techniques are dependent on the accumulated experience and the sensation felt by the Examiner, the techniques are difficult to be fully mastered. In particular, diagnosis by the Ayurveda method is restricted to those with extreme sensitivity at the finger tip, which can number as little as one in a thousand, or one in several thousand people. Moreover, even for those with sensitive touch, unless they have had many years of training, they cannot make an accurate diagnosis.

As described above, the pulse waves are useful index of the conditions of a living body, and potentially form an excellent basis for a diagnostic technique. If it is possible to derive information related to the conditions of the living body from the pulse waves, and to perform objective and accurate diagnostics based on such information, it would signify a great leap in the field of remedial medicine.

The present invention was made in view of the background of the diagnostics technology presented above, and some of the objectives of the present invention are to present:

(1) A diagnostic apparatus for performing diagnosis of the conditions of an examinee based on the pulse waves obtained from the examinee in a manner similar to expert medical person.

(2) A pulse wave analysis apparatus for analyzing and acquiring data which not only reflect the conditions of the examinee but enable objective diagnosis to be performed.

(3) A diagnostic apparatus for performing objective diagnosis of the conditions of the examinee based on pulse waves obtained from the examinee.

SUMMARY OF THE INVENTION

To achieve these objectives, the diagnostic apparatus of the present invention comprises: an analysis section for generating waveform parameters from the information, obtained from an examinee, representing the conditions of the examinee; and a diagnostic section for performing diagnosis of the conditions of the examinee based on the waveform parameters.

More specifically, the analysis section of the present invention generates the following waveform parameters by analyzing the pulse waves obtained from the examinee:

(1) values of the elements of an electrical circuit model (lumped four parameter circuit model) which simulates the arterial system of a living body from a proximal section to a distal section;

(2) distortion factors in the waveforms in comparison to reference waveforms obtained from a plurality of living bodies;

(3) peak points (inflection points) in the waveforms and/or their generation timing; and (4) a frequency spectrum of sequential pulse wave data.

The diagnostic items which can be analyzed by the apparatus of the present invention are illustrated by way of various embodiments, and disclosed in the claims of the present invention.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 10 is a block diagram to show a pulse wave analysis apparatus to compute dynamic parameters of the circulatory system based on the concept of a second embodiment of the present invention;

FIG. 11 is a schematic illustration of using the pulse wave detection device and the stroke volume determination device;

FIG. 27 is a schematic block diagram to show of a diagnostic apparatus based on the shape of pulse Waveforms, and based on the concept of a third embodiment of the present invention;

FIG. 28 is an illustration to explain a method of pulse wave examination;

FIG. 43 illustrates a psychosomatic fatigue level diagnostic questionnaire used in the embodiment;

DESCRIPTION OF THE PREFERRED EMBODIMENTS

Best Mode for Carrying Out the Invention

Preferred embodiments of the present invention will be explained with reference to the drawings. All of these embodiments are based on the results of analysis and diagnosis performed on actual pulse waves detected from actual examinees.

To facilitate understanding, the embodiments are presented in separate Chapters 1 to 5 so that those skilled in the art may be able to duplicate the embodiments.

In Chapter 1, an expert system is presented to perform diagnosis based on most easily recognizable waveforms so that the principle of the present invention can be understood by those skilled in the art. To perform such a diagnosis, it is necessary that the waveforms are correlated to conditions of an examinee, and additionally those parameters must be truly reflective of the conditions of the examinee.

In Chapters 2 and 3, circulatory dynamic parameters are chosen to represent the parameters representing the conditions of an examinee. A method for obtaining such hemodynamic parameters are illustrated with an embodiment, as well as an embodiment for a diagnostic apparatus for performing diagnosis based on such parameters.

In Chapter 4, an embodiment of a diagnostic apparatus is presented to obtain relevant information related to the condition of an examinee, and to perform diagnosis based on such information. The explanations provided include specific steps so that those skilled in the art may be able to construct such diagnostic apparatuses in accordance with the present invention. The disclosures of Chapter 4 are helpful to those skilled in the art to construct devices other than the psychosomatic stress level analysis apparatus presented in the embodiment.

In Chapter 5, an improved pulse wave analysis apparatus is presented to further improve the performance of the apparatuses presented in the foregoing embodiments.

Chapter 1: Diagnostic Apparatus

First, a first embodiment of the diagnostic apparatus according to the present invention will be explained. This diagnostic apparatus has a pre-recorded memory which relates the pulse wave data to the conditions of a living body, and performs comparative analysis to identify the detected waveform of an examinee with the stored waveforms in the memory.

Chapter 1 is devoted exclusively to the first embodiment of the present invention.

Chapter 1-1: Structure of the Embodiment

Figure 2:
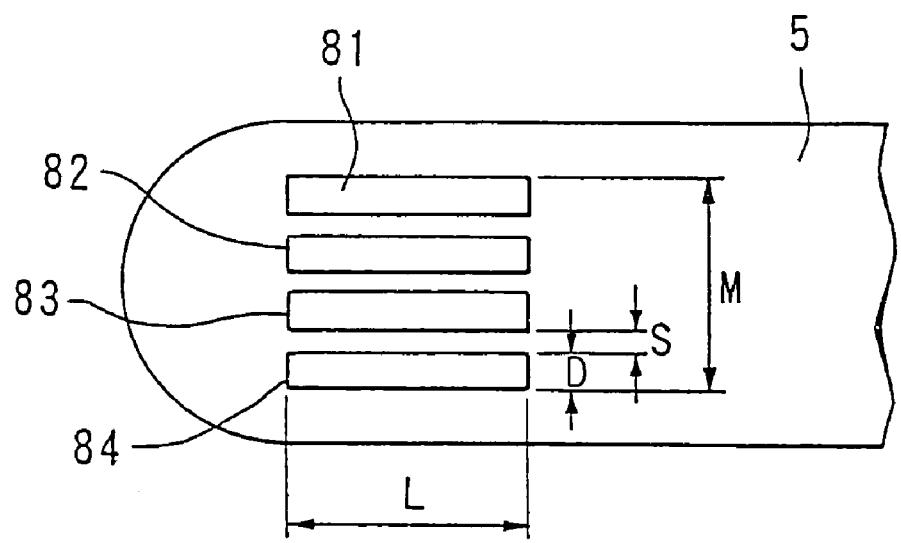
FIG. 2 is a plan view showing the essential parts of a pulse wave sensor used in the embodiment.

FIG. 2 shows a plan view of a pulse wave sensor used in the embodiment.

In FIG. 2, numerals 81-84 indicate a set of band shaped strain gages which are arranged in parallel in the longitudinal direction on a finger portion of a rubber glove 5. The thickness of the rubber glove 5 is approximately 200 μm Standard gauge type adhesive is used to fixedly attach the strain gages 81-84 to the rubber glove 5.

The details of the strain gages 81-84 are as follows:

Each of the strain gages 81-84 is a thin gauge with a gauge factor of 2.1; resistance of 120 ohms; a width (D) of 2.8 mm; a length (L) of 9.4 mm; and a thickness of 15 μm. The overall width M of the strain gages 81-84 corresponds to the contact width of the finger of the examiner when the finger is gently pressed on an arm of the examinee, and is set at approximately 12 mm. Accordingly, the distances (S) between the gauges 81-84 is approximately 0.27 mm.

Figure 3A:
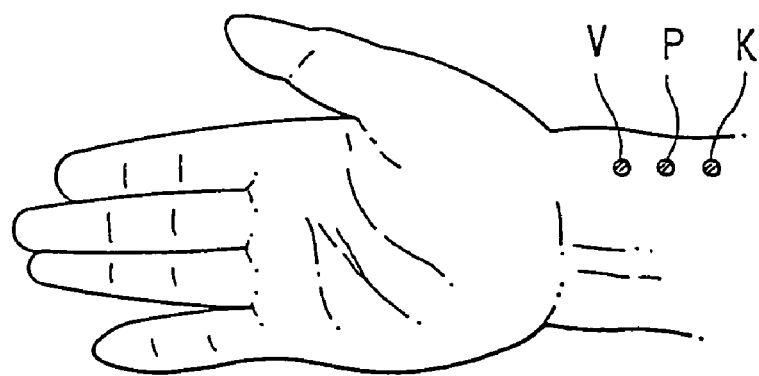
FIG. 3A is a diagram illustrating the three pulse taking location on the arm of an examinee in Ayurveda technique.
Figure 3B:
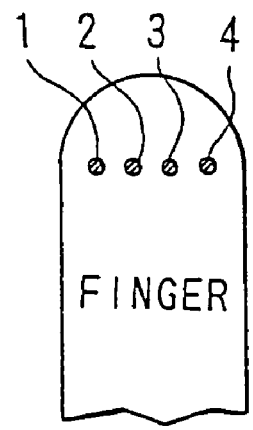
FIG. 3B is a diagram illustrating the four points on the examiner's finger in the Ayurveda technique.

The strain gauges 81-84 correspond to the measuring points 1-4 as shown in FIG. 3B, and are used to measure the pulsing motion at the respective Ayurveda shown in FIG. 3A.

The construction of the diagnostic apparatus using the strain gages 81-84 will be explained with reference to FIG. 1.

In the figure, a strain gage 81 and a resistor 12 are connected in series, with a predetermined DC voltage E applied by a voltage source 11. Accordingly, an AC voltage $V_i$ corresponding to the resistance ratio, is generated across the ends of the strain gage 81. The numeral 13 indicates a DC cut-off filter which removes the DC component of the AC voltage $V_i$.

The output signal from the DC cut-off filter 13 is amplified by an amplifier 14, and outputted by way of a low pass filter 15 which has a cut-off frequency of 20 Hz. FIG. 2 shows only the circuit corresponding to the strain gage 81. Similar circuits are respectively provided for the other strain gages 82-84.

Subsequently, the output voltage $V_o$ from the low pass filter 15, is converted into a digital signal by an A/D converter 20, and then supplied to a micro-computer 21. The micro-computer 21 comprises a CPU 24, a ROM 22, a RAM 23, and a display device DP. It also has a database 26 as an external memory. A program specifying the operation of the CPU 24, is stored in the ROM 22, while a working area is set in the RAM 23. The numeral 25 indicates an input device comprising a keyboard or the like, whereby various commands and messages can be input to the CPU 24. The numeral 30 indicates a recorder, which prints out waveform data supplied from the CPU 24, on a specified sheet.

Chapter 1-2: Operation of the Embodiment

There are two operative modes of the first embodiment; the learning mode and the diagnostic mode. The explanations for the operation of the first embodiment are divided into those two modes.

Chapter 1-2-1: Learning Mode

The learning mode is used to store the relationship between the parameters representing the pulse waves (waveform parameters) obtained from the examinee and the data representing the conditions of the examinee (i.e., diagnosis results).

With the above construction, the examiner wears the rubber glove 5 on one hand, and presses the second finger on the Vata (V), the third finger on the Pitta (P), and the fourth finger on the Kapha (K), of the examinee.

In this condition, respective voltages $V_i$ are outputted from a total of 12 strain gages, corresponding to the pulsing motion of the examinee. The direct current components of these voltages $V_i$ are filtered out in the corresponding DC cut-off filters 13, and are supplied to the micro-computer 21 by way of the respective corresponding amplifiers 14, low pass filters 15, and AID converters 20. The waveforms supplied in this way are analyzed in the micro-computer 21, and parameters indicating the characteristics are computed. These parameters are then stored temporarily in the RAM.

In the present embodiment, the amplitudes of the respective frequency components constituting the pulse waves are used as the characterizing parameters. That is to say, a frequency spectrum analysis by Fast Fourier Transform is carried out for, the respective waveforms (the program for the Fast Fourier Transform is pre-stored in ROM 22 or RAM 23), and the amplitudes of the various frequencies are used as parameters. Further, as will be explained subsequent to Chapter 2, the present invention may utilize various other parameters representing the pulse waves.

The examiner then inputs diagnosis results(as teaching data) corresponding to the computed parameters from the input unit 25. The diagnosis results in this case are those from the sense of the finger touch, and those from observation of the waveform displayed on the display device, or both of these. Additionally, a completely different method of diagnosis such as a Western medical opinion may also be used. The input may also include words directly indicating the name of an illness and symptoms can be inputted from the input unit 25. The input data may also be corresponding codes.

When the diagnosis results from the examiner are inputted, the CPU 24 stores these in the database 26 matched with the parameters stored temporarily in the RAM 23.

Next, the learning mode will be explained for each actual symptoms of an illness.

(1) Chronic Nasal Inflammation

In this example, the patient was a 28 year-old-male, diagnosed by Western medical opinion to have chronic nasal inflammation.

Figure 4A:
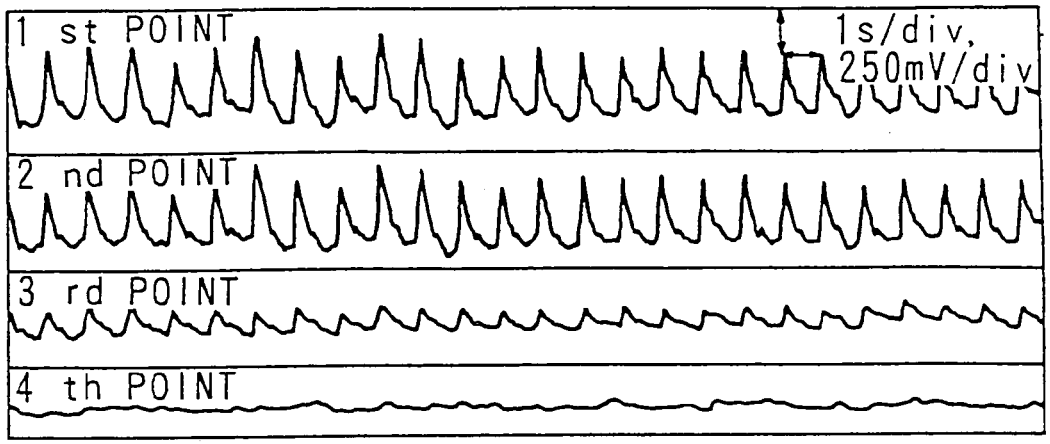
FIG. 4A to FIG. 4C are graphs showing examples of detected pulse waves.
Figure 4B:
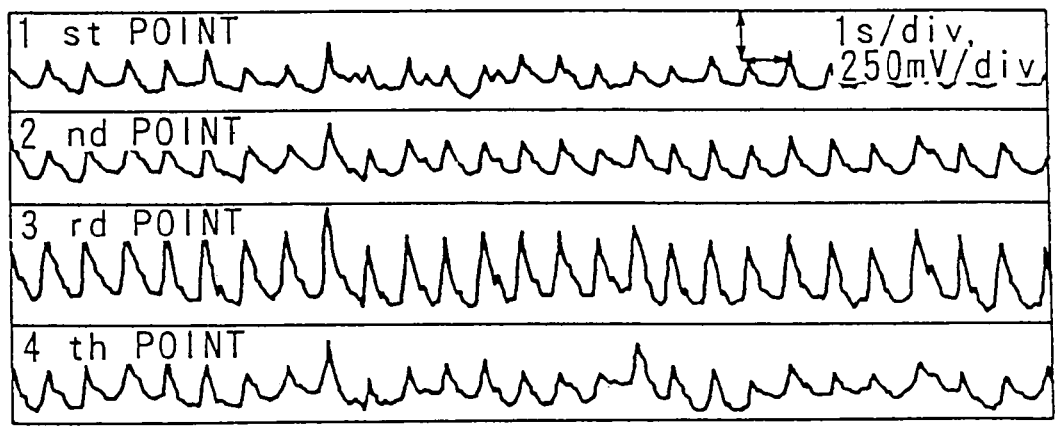
Figure 4C:
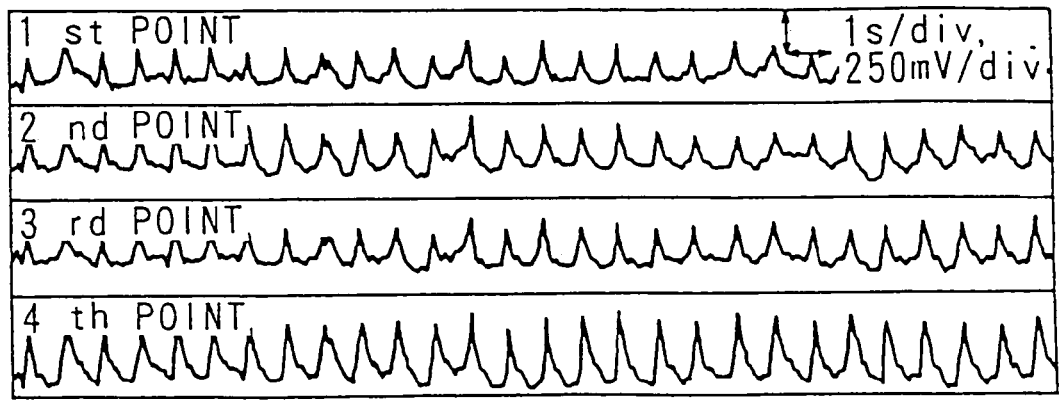

The pulse waves measured from the patient were recorded by the recorder 30. The results are shown in FIGS. 4A-4C. Here the vertical scale in FIG. 4A is 2 times that in FIGS. 4B and 4C. This is done for convenience to keep the waveform on the scale. Accordingly, the amplitude of Udana Vata (V) waveform is large compared to the other waveforms. Furthermore, from the observation of the measured results of the Vata (V) in FIG. 4(A), it can be seen that the waveform amplitudes for the first and second points are much larger compared to those for the third and fourth points.

Meanwhile, the micro-computer 21 performs a frequency spectrum analysis by Fast Fourier Transform on the respective-waveforms, and the results are stored in the RAM 23 as parameters.

For the pulse wave characteristics shown in FIG. 4, the Ayurveda technique gives a diagnostic opinion of a nasal pharynx disorder. With the appearance of such pulse waves there is a statistically high probability of a disorder in the nose, throat or bronchial tube. This has been reported in "Visualization of Quantitative Analysis of the Pulse Diagnosis in AYURVEDA: K. Kodama, H. Kasahara, The proceeding of the 4th world congress holistic approach-health for all in Bangalore, India 1991".

From the observation of the output results from the recorder 30, and the waveform shown on the screen of the display DP, and also from an Ayurveda diagnosis by sense of touch, or on the basis of a Western medical opinion, the examiner inputs an opinion for the diagnosed result (chronic nasal inflammation), or a code indicating this opinion, from the input unit 25 into the diagnostic apparatus.

Subsequently, the CPU. 24 matches the diagnosed input result with the parameters temporarily stored in the RAM 23, and stores them both in the database 26.

(2) Liver Disorder Example (i)

In this example the patient was a 28-year-old male with a liver disorder (GTO "42", GPT "63").

Figure 5A:
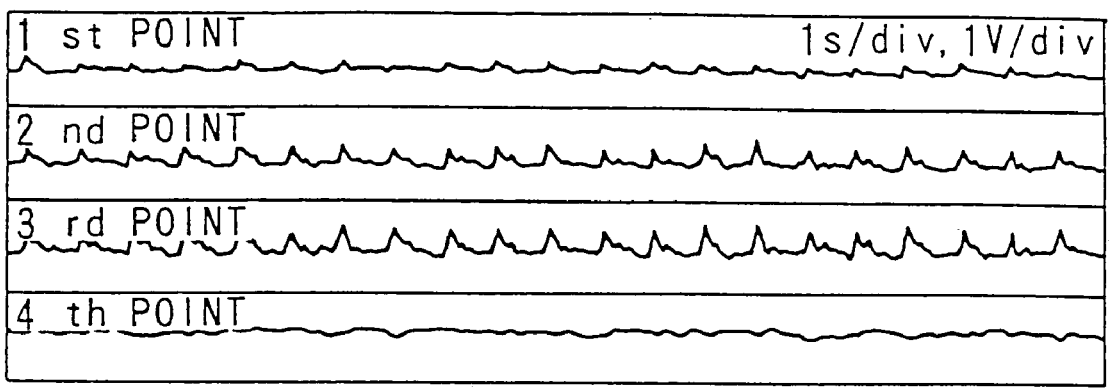
FIG. 5A to FIG. 5C are graphs showing examples of detected pulse waves.
Figure 5B:
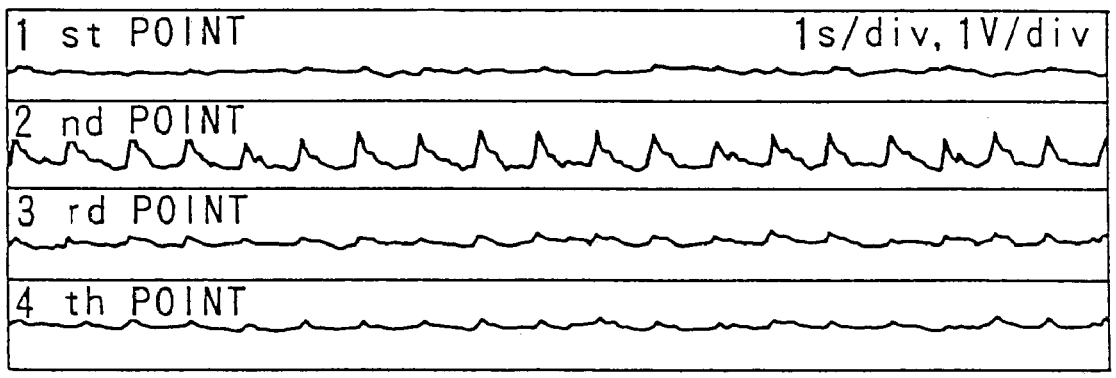
Figure 5C:
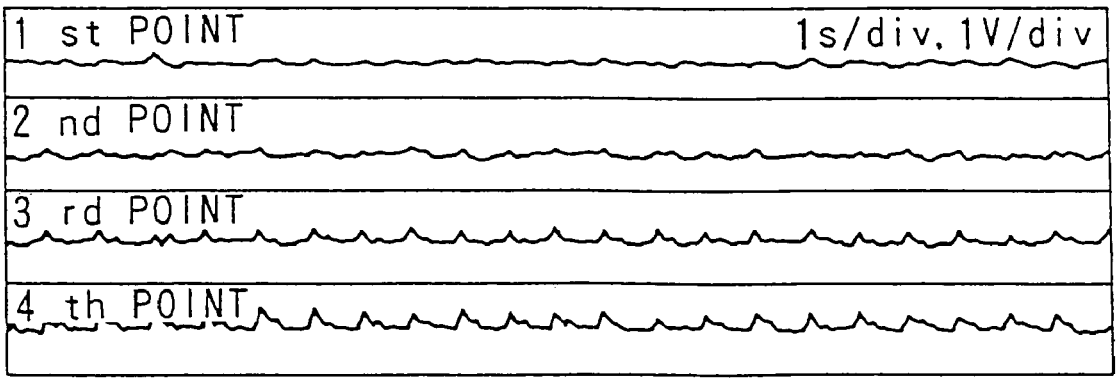
Figure 6:
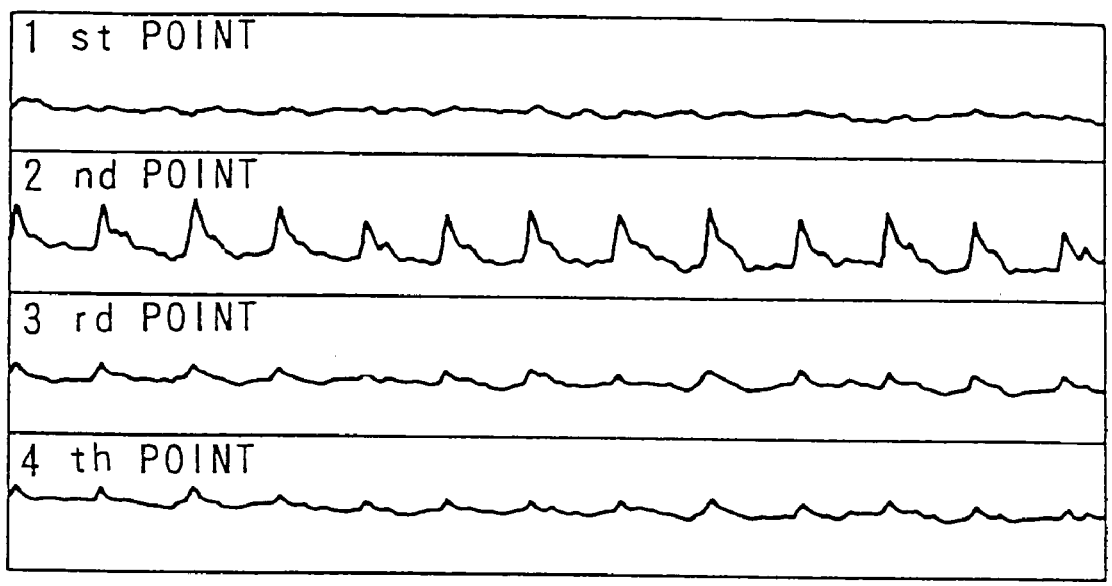
FIG. 6 is a graph showing examples of detected pulse waves.

The examiner's pulse wave measurement results are shown in FIGS. 5A-5C. The scales in these Figs. are the same. From these results it can be seen that the amplitude of the waveforms for the Ranjaka Pitta (P) of the third finger are large compared to those for the other fingers. A magnified view of FIG. 5B is shown in FIG. 6. From FIG. 6 it can be seen that the amplitude for the second point is greater than that for the other points.

The micro-computer 21 performs a frequency spectrum analysis by Fast Fourier Transform on the respective waveforms in similar manner to the above case (1), and the results are stored in the RAM 23 as parameters.

Incidentally, the Ayurveda diagnosis indicated a liver disorder or the stomach/intestine problem.

Here the examiner in a similar manner to the above mentioned case, from an Ayurveda opinion by sense of touch, or on the basis of a Western medical opinion, inputs an opinion for the diagnosed result (liver disorder), or a code, indicating this disorder, from the input unit 25 into the diagnostic apparatus.

Subsequently, the CPU 24 matches the inputted diagnosis result with the parameters temporarily stored in the RAM 23, and stores them in the database 26.

(3) Liver Disorder Example (ii)

Next example is a diagnosis for a different liver disorder. The patient was a 24-year-old male with a liver disorder (GTO "36", GPT "52").

Figure 7:
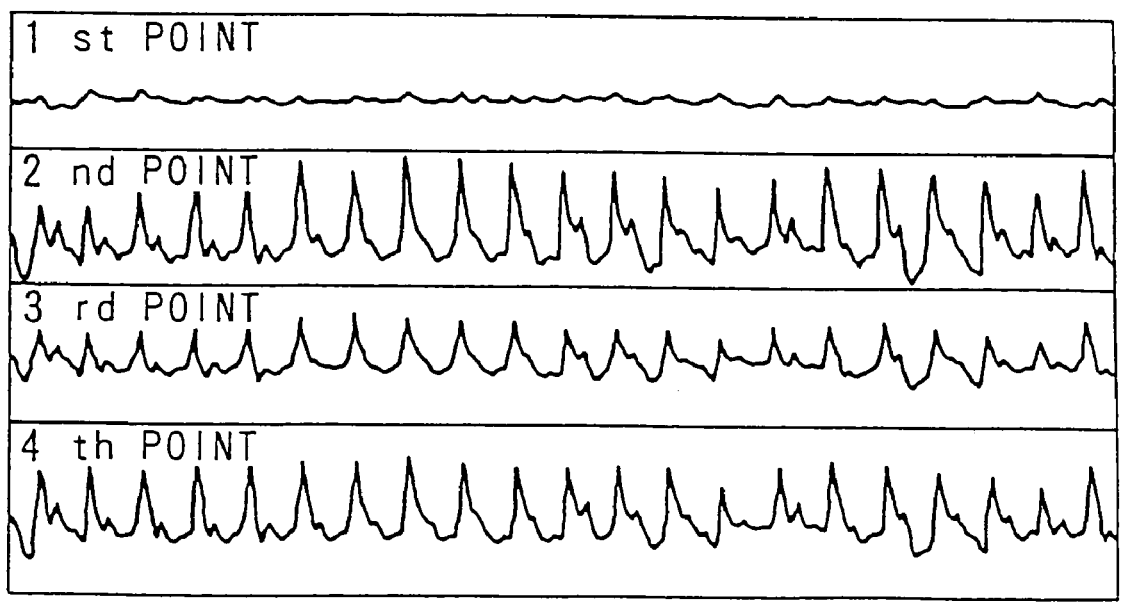
FIG. 7 is a graph showing examples of detected pulse waves.

With this patient also, the amplitude of the waveform in the Ranjaka Pitta (P) was larger than the amplitude for the other fingers. The waveform measurement results for this Pitta (P) are shown in FIG. 7. In FIG. 7 it can be seen that the amplitude for the second point is greater than that for the other points.

Accordingly, with this liver disorder example also, similar results to those of the before mentioned liver disorder example (i) were obtained.

In this case also parameter computations by the computer 24, and input of the results by the examiner are done in a similar manner to the above case. However, since the waveforms of FIG. 5 and FIG. 7 were slightly different, the parameters were slightly different to the case of the liver disorder (i). Even though the diagnostic results are the same, because a certain degree of variation appears in the possible parameter values, the reliability of the limits can be improved by accumulating many clinical examples.

(4) Heart Disorder (i)

In this example, the patient was a 26-year-old male having irregular pulses which appeared several times an hour due to an outer contracting ventricle of the heart.

Figure 8:
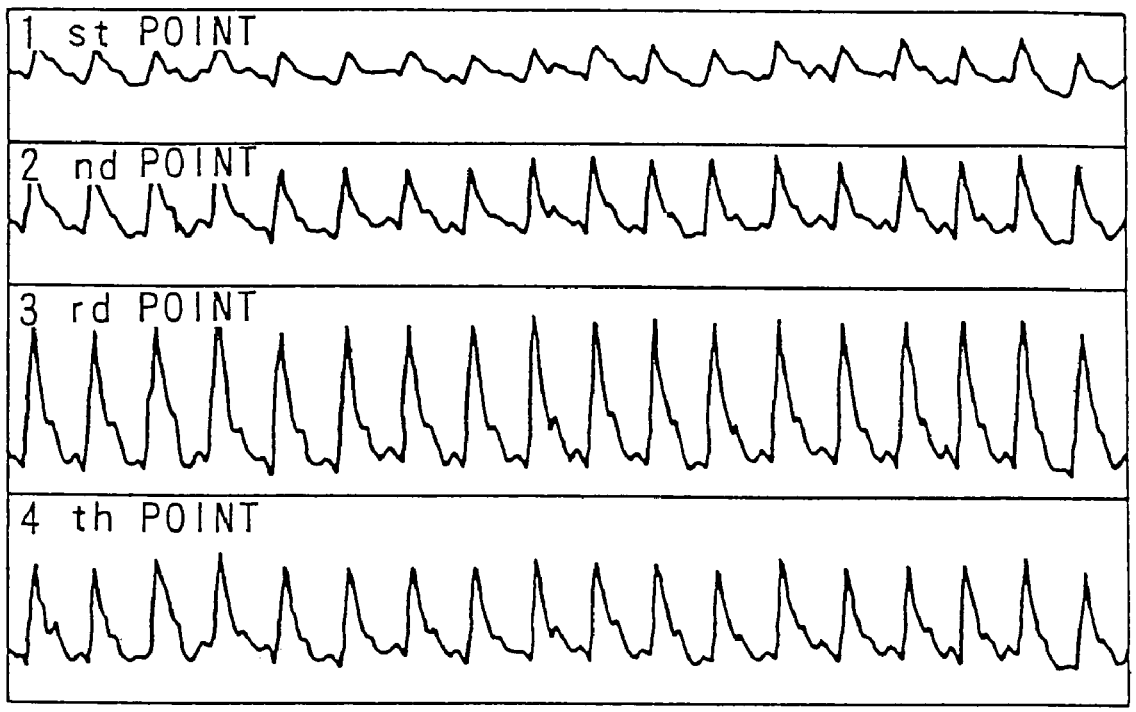
FIG. 8 is a graph showing examples of detected pulse waves.

With the waveform measurement results of the patient, the amplitude of the waveform for the Sadhaka Pitta (P) of the third finger was larger than these for the other fingers. The waveform measurement results for the Sadhaka Pitta (P) are shown in FIG. 8. As is clear from FIG. 8, the amplitude for the third point is greater than those for the other points.

Incidentally, the Ayurveda diagnosis indicated a disorder of the heart for the above illness example. Accordingly, in this diagnosis example also, the diagnosis results from the Ayurveda or from Western medical opinion were inputted for the parameters calculated by the CPU 24, and both were matched and stored in the database 26 so that the symptoms with respect to the pulse waves could be learnt.

(5) Heart Disorder (ii)

To confirm the reproducibility of the heart disorder example (i), a diagnosis was made for a different heart disorder example. The patient was a 38-year-old male having irregular pulses which appeared several times an hour due to an outer contracting ventricle of the heart.

Figure 9:
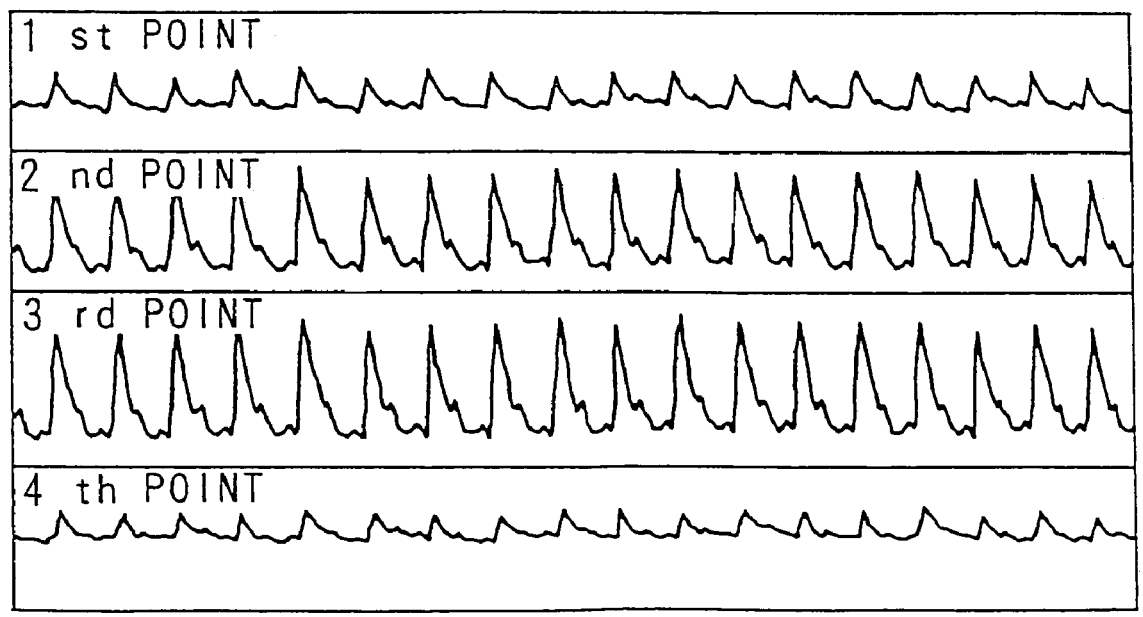
FIG. 9 is a graph showing examples of detected pulse waves.

With this patient also, the amplitude of the waveform for the Sadhaka Pitta (P) of the third finger was larger than those for the other fingers. The waveform measurement results for the Sadhaka Pitta (P) are shown in FIG. 9. As is clear from FIG. 9, the amplitude for the third point is greater than those for the other points.

In this case also parameter computations by the computer 24 and input of the results by the examiner are made in a similar manner to the above cases, and matched and stored in the database 26.

Chapter 1-2-2: Diagnosis Mode

Next, the diagnostic mode will be explained. The diagnostic mode performs: detection of pulse waves from an examinee; computation of the parameters representing the pulse waves; and diagnosis by reading out applicable diagnostic results from the database 26.

The examiner operates the input unit 25 to indicate the diagnosis mode for input to the CPU 24. Then in a similar manner to that for the learning mode, he puts one hand into the rubber glove 5, and his second finger presses the examinee at Vata (V); his third finger at Pitta (P); and his fourth finger at Kappa (K).

As a result, respective voltages Vi are output from the strain gages of the respective fingers, and supplied to the microcomputer 21 by way of the DC cut-off filter 13, amplifier 14, low pass filter 15 and A/D converter 20. The micro-computer 21 then calculates parameters to express the characteristics of the supplied waveforms, and temporarily stores these in the RAM 23. The CPU 24 then searches in the database 26, for a parameter equal to the parameter temporarily stored in the RAM 23, or the closest parameter to that parameter, reads the diagnosis result matched with that parameter, and displays this on the display device DP. In this case, if there is no equivalent parameter, the diagnosis results corresponding to the closest parameter are displayed, then that fact is also displayed at the same time. Such a message is pre-stored in the ROM as character information, and appropriately displayed.

With the display device DP as described above, diagnosis results (as teaching data) such as chronic nasal inflammation, liver disorder, heart abnormality/disorder are displayed. Accordingly, the examiner can make a diagnosis for that patient based on the displayed results.

Here, the embodiment offers an advantage that if teaching data compiled by expert Ayurveda practitioner had been preloaded in the diagnostic memory provided in the learning mode, even a beginner in the Ayurveda technique would be able to perform a diagnosis at the expert level.

Chapter 1-3: Variation of the First Embodiment

The first embodiment is not limited to the above diagnostic apparatus. For example, a number of variations such as given below are also possible.

Variation (i)

In the first embodiment, the frequency spectrum by FFT were used as waveform parameters. However, instead of this, each value of the elements of a lumped four parameter circuit model simulating the arterial system may be used. The electrical model will be described below.

Variation (ii)

Waveform spectrum obtained by discrete FFT, or waveform spectrum obtained by the so-called maximum entropy method technique may be used for the parameter.

Variation (iii)

In the above embodiment, the radial arterial pulse waves were used. However, it is possible to utilize parameters for brain waves or finger tip pulse waves. Moreover, parameters for the accelerating wave of the finger tip pulse wave may be utilized. The main point is that the present invention is applicable provided there is some wave motion which reflects the condition of the living body. The living body to be measured is not limited to human beings but may be other types of animals.

Variation (iv)

In the traditional medicine, Ayurveda for example, a large amount of diagnostic data has already been accumulated. Accordingly, if this data can be used directly and quickly in a clinical manner, then there is ease when it is better to adjust the number of measuring points to those of the traditional medicine. Hence, it is permissible to have less than four strain gages provided there is more than one. For example, it is known that the traditional medicine of Tibet considers two measurement points on one finger. Accordingly, in carrying out the diagnosis based on this traditional medicine, two gauges would sufficient.

Variation (v)

Figure 1:
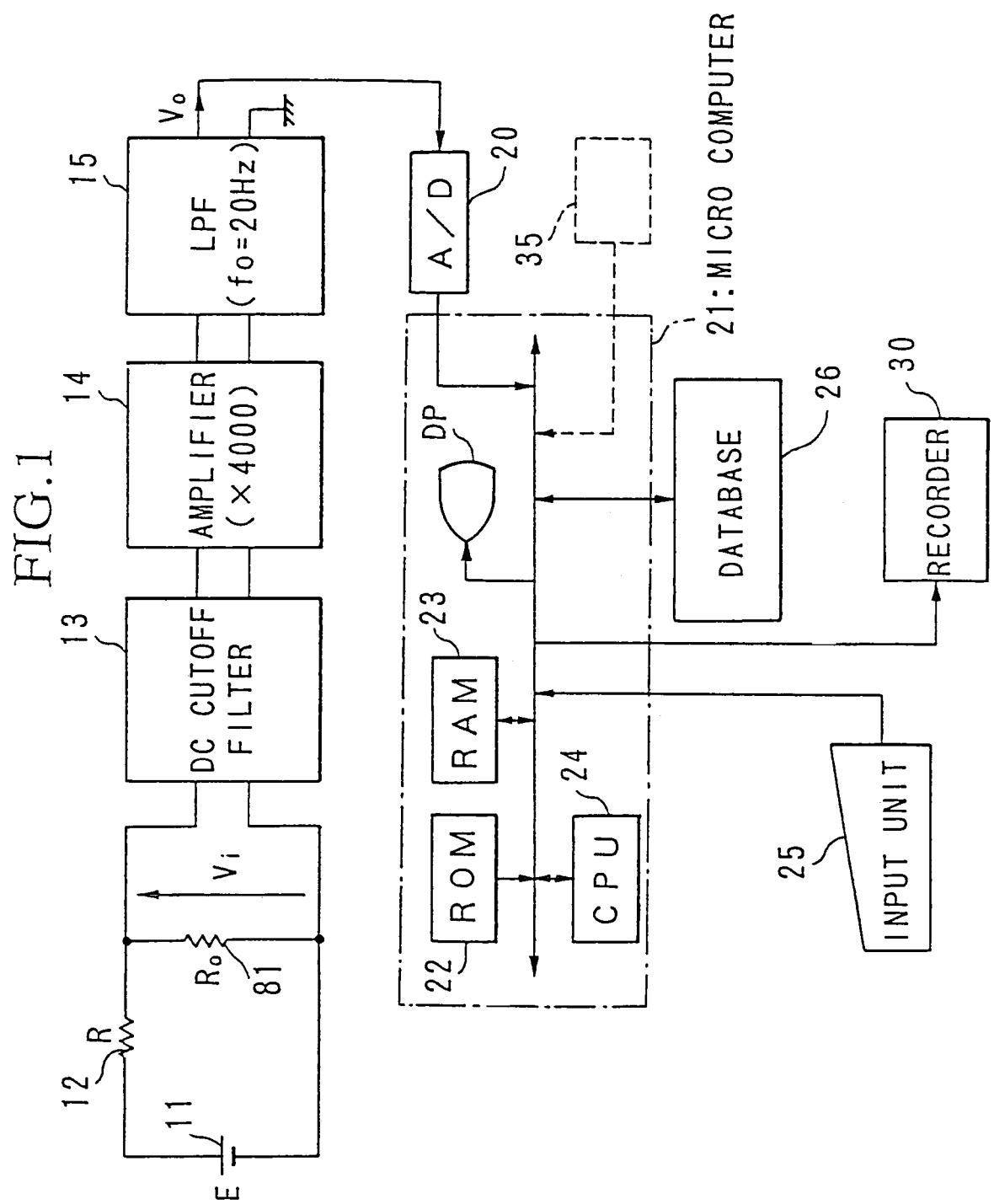
FIG. 1 is a block diagram of a diagnosis apparatus according to a first embodiment of the present invention.

In the circuit shown in FIG. 1, the pulse wave is detected by directly measuring the voltage $V_i$ across the terminals of the strain gage 81. However a bridge circuit with the strain gage 81 at one side can be constructed, and the pulse waves are detected by measuring the voltage across the opposite corners of the bridge circuit. By constructing a bridge circuit with the strain gage and three thin film resistors having the same temperature resistance coefficient as the strain gage 81 adhered to the rubber glove 5, then a temperature drift due for example to the body temperature can be compensated for, and the sensitivity can be improved.

Variation (vi)

In the circuit shown in FIG. 1, a current is supplied continuously to the strain gage 81. However the current supply to the strain gage 81 may be intermittent. That is to say, with the circuit in FIG. 1, since the portion of the frequency component of the voltage $V_i$ detected finally as pulse waves only has frequency components below 20 Hz, therefore even with the results sampled at a frequency of 40 Hz, adequate waveform reproduction is possible. Hence the current supplied to the strain gage 81 can be intermittent, enabling a reduction in power consumption, which is beneficial, particularly with portable equipment.

Variation (vii)

In the first embodiment, the parameter inside the database 26 matching the calculated parameter in the diagnostic mode is retrieved. However instead of this, respective threshold values can be set for the upper and lower limits of the respective parameters inside the database 26. When in the diagnosis mode, if the calculated parameters fall within this range, they can be considered as the relevant parameters inside the database 26, and that diagnosis result may be outputted. Moreover, with the data inside the database 26, this is updated when new diagnosis results are inputted for the same parameter. However, if a parameter of a close value is newly inputted, the above threshold value can be updated.

Variation (viii)

In the above embodiment, the pulse wave parameter is calculated, stored and a comparison is made. However, when there is no problem with increasing the memory capacity or processing time, the waveforms themselves can be stored and compared.

Variation (ix)

It is also possible to display the therapeutic procedure corresponding to the symptoms of the patient together with or instead of the diagnosis results. The therapeutic procedure may be outputted as the teaching data in the first embodiment. In the learning mode, diagnosis results together with the therapeutics (or the therapeutics instead of the diagnosis results), can be inputted easily.

In the above, the configuration of the basic diagnostic apparatus has been explained. In the following Chapters 2 through to 5, parameters representing the pulse waves will be explained together with the method of generating such parameters.

Chapter 2: Pulse Wave Analyzer for Computing Parameters of the Circulatory System In the modern medicine, the most common procedure in the examination process of the cardiovascular system of a human body, is to measure the blood pressure and the heart beat rate. However, to perform more detailed examination, other circulatory dynamic parameters such as the vascular resistance and compliance must also be examined.

Conventionally, to measure such circulatory dynamic parameters, it is necessary to determine the pressure waveforms and the blood flow rate at the aorta ascendens and at an incision site. The measurement method involves either directly by an insertion of a catheter in an artery, or indirectly by ultrasonic measurement.

However, according to the catheter method, there is a problem that a large invasive equipment is required. The ultrasonic technique can measure the blood flow non-invasively, but the technique requires expert operator, and the apparatus is also large.

To solve these problems, the present inventors therefore devised a pulse wave analysis apparatus based on an electrical simulation circuitry to non-invasively follow the hemodynamics of a living body with the use of circulatory dynamic parameters.

More specifically, the pulse wave analysis apparatus-operates by: simulating the arterial system from a proximal section to a distal section with an electrical circuit (hereinbelow referred to as the electrical model); entering electrical signals representing the pressure waveforms at the proximal section into the circuit; iterating the values of the elements of the circuit so as to duplicate the actual pressure waveforms detected from the distal section of the examinee; and outputting the computed results corresponding to each of the circulatory dynamic parameters.

In this case, it is obvious that the computed parameters may be used as the waveform parameters in the first embodiment.

In this pulse wave analysis apparatus, the radial arterial pressure waveforms are used as the waveforms to be analyzed in the distal section of the living body, and the aorta ascendens pressure waveforms are used as the waveforms to be analyzed in the proximal section of the living body.

Also in this embodiment, the basic assumption is that the pressure waveforms at the aorta ascendens are nearly constant and are not much affected by the conditions of the living body, and it is mainly the performance of the arterial system which is affected by the conditions of the living body. This assumption has been clinically verified by the inventors.

In the following, a pulse wave analysis apparatus according to a second embodiment will be explained.

Chapter 2-1: Structure of the Embodiment

FIG. 10 shows a block diagram of the pulse wave analysis apparatus in accordance with the second embodiment of the invention.

This embodiment computes the circulatory dynamic function of an examinee based on information obtained from evaluation of the circulatory dynamic parameters of a human body with a non-invasive sensor. The actual details of the circulatory dynamic parameters will be explained later.

In FIG. 10, the reference numeral 201 refers to a pulse wave detection apparatus, 202 is a stroke volume determination device. The pulse wave detection apparatus 201 determines the radial artery waveform via the pulse wave sensor S1 worn on the examiner's hand (or on the wrist of an examinee), as shown in FIG. 11, and also determines the blood pressure of the examinee via a cuff belt S2 worn on the upper arm section of the examinee. The waveform of the radial artery is corrected by the blood pressure, and the corrected waveform of the radial artery is outputted as electrical analogue signal.

The analogue signal outputted from the pulse wave detection device 201 is inputted into an A/D converter 203, and is converted into digital signals for every sampling cycle. Also, the stroke volume determination device 202 is connected to the cuff belt S2, as shown in FIG. 11, and determines the volume of blood circulated for one pulsation (beat) via the cuff belt S2, and outputs the results (digital signals) as the stroke volume per pulsation. This measurement can be provided by the so-called Contraction Surface Area method.

Figure 24:
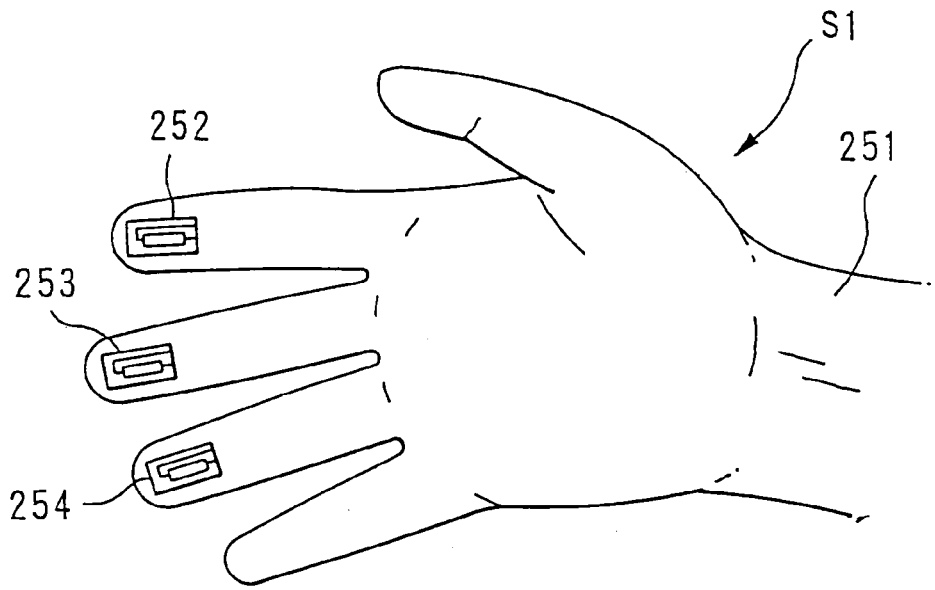
FIG. 24 is a perspective of a pulse wave sensor.

Here, the details of the pulse wave sensor S1 will be explained with reference to FIG. 24.

In this figure, the reference numeral 251 refers to a surgical rubber glove, which is provided with strain gages 252-254 at the finger pad side of the first joint of the index, third and fourth fingers. The strain gages 252-254 are thin gages, and have a gage factor (170), a resistance (2 k ohm), a width (0.5 mm) and a length (4 mm). Each of the strain gages 252-254 is-fixed on a flexible thin base, and is attached to the rubber glove 251 with thin the base.

Next, the pulse wave detection device 201 is explained with reference to FIG. 25.

In the figure, the reference numeral 268 refers to a known blood pressure meter, and measures and outputs the blood pressure value through the cuff belt S2. The numeral 261 is a constant current source, and supplies a constant current to the strain gage 252. The ends of the strain gage 252 generate a voltage $V_g$ to correspond to the degree of physical strain. The voltage $V_g$ is amplified through a direct current (DC) amplifier 262, and is supplied to the DC cut-off circuit 263 and to the averaging circuit 265. The output voltage generated by the DC amplifier 262 can be expressed as $(V_o+V_d+\Delta V)$. Here $V_o$ is the voltage generated when the examiner wears the glove 251, $V_d$ is the voltage generated when the examiner's finger is pressed against the arm of the examinee. The voltage $\Delta V$ is an alternating current (AC) voltage generated by the pulse pressure of the examinee.

The DC cut-off circuit 263 eliminates the first two DC components from the voltages, $V_o$, $V_d$ and $\Delta V$, and outputs the AC voltage $\Delta V$, i.e. the pulse wave signal. The pulse wave signal is supplied, after removing the noise, to the microcomputer 204 via a low pass filter 264 with the cut-off frequency of 20 Hz via the A/D converter 203 (See FIG. 10).

On the other hand, the averaging circuit 265 detects the maximum value of $(V_o+V_d+\Delta V)$, and taking a cycle to be to the period of the next generation of the maximum value of $(V_o+V_d+\Delta V)$, obtains an average value of $(V_o+V_d+\Delta V)$. This operation eliminates the AC component $\Delta V$, and the DC component $(V_o+V_d)$ is outputted. The reference numeral 266 is a level memory circuit, and when a switch 266a is pressed down, memorizes the output voltage value at that time of the averaging circuit 265, and outputs the voltage at the memorized level periodically. The numeral 267 is a decrementor, and subtracts the output voltage of the level memory circuit 266 from the output voltage of the averaging circuit 265, and outputs the decremented value.

Figure 25:
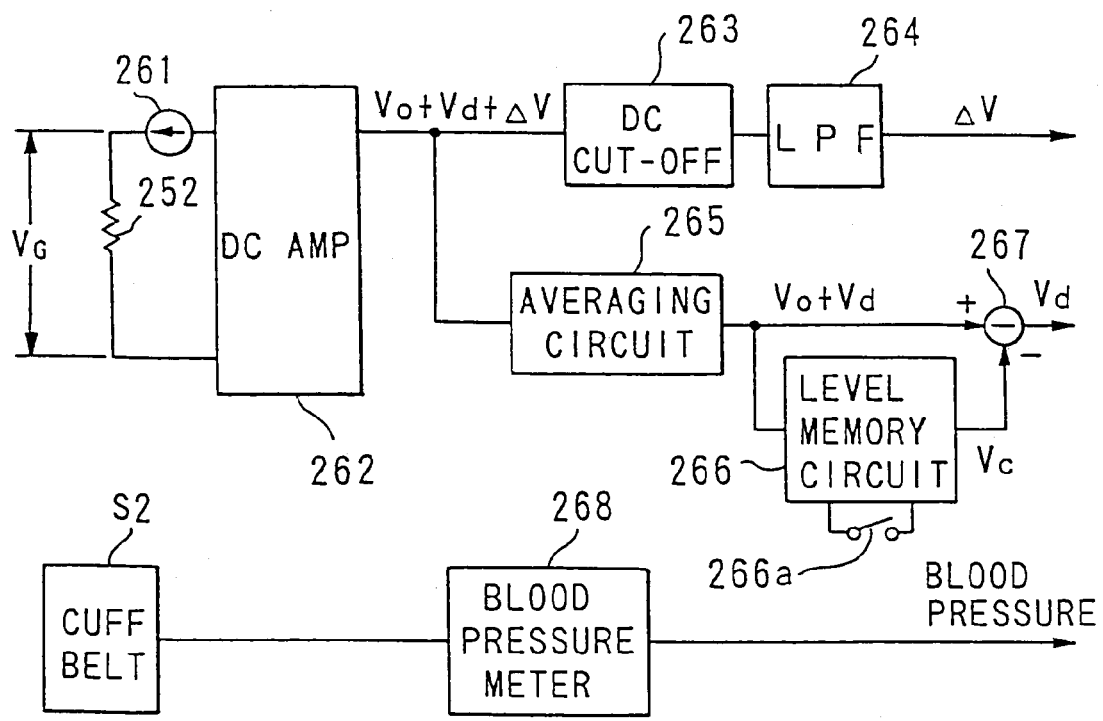
FIG. 25 is a block diagram of the pulse wave detection device.

In FIG. 25, when the examiner wears the glove 251, the DC amplifier 262 output a voltage $V_o$. When the switch 266a is pressed in this condition, the voltage $V_o$ is memorized in the level memory circuit 266. Next, the examiner presses the finger while wearing the glove 251 on the arm of the examinee, the averaging circuit 265 generates a voltage $(V_o+V_d)$, and a voltage $V_d$ corresponding to the finger pressure of the finger is outputted via the decrementor 267. At the same time, the voltage $\Delta V$ corresponding to the pulse wave is outputted successively through the DC cut-off circuit 263, and the low pass filter 264. Further, the examiner can carry out his own examination based on finger feeling using the strain gages 252-254 disposed on the thin rubber glove 251. The above circuit components 261-267 are provided to work with the strain gages 252, but similar circuit components are provided for the strain gages 253, 254.

The micro-computer 204 performs the following steps in accordance with the commands inputted through the keyboard 205.

(1) Reading of the pulse waves by storing the sequenced digital signal of the radial artery pulses obtained through the A/D converter 203 in an internal waveform memory.

(2) Averaging of the pulses taken at the three locations (Chun, Guan, Chi) and taken into the internal memory, and obtaining a corresponding radial artery pulse waveform.

(3) Taking in of pulsing volume data.

(4) Obtaining an equation to correspond with the above one pulse, and based on this equation, and calculating each parameter to correspond with an electrical model of the arterial system of the examinee.

(5) Outputting the parameters obtained by parameter computation as circulatory dynamic parameter from an output device (not shown; for example, printer, display device etc.)

The details of these processing steps will be explained under the explanation section for the operation.

Figure 12:
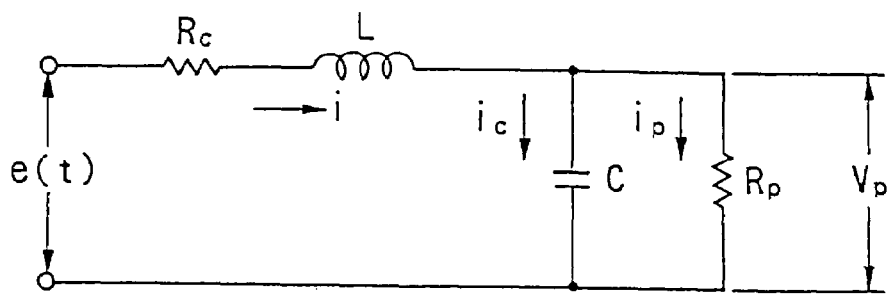
FIG. 12 is a schematic circuit diagram showing a lumped four parameter circuit model to simulate the arterial system of a human body.

Chapter 2-1-1: With Respect to the Electrical Model Utilized in this Embodiment (1) Lumped Four Parameter Circuit Model In this embodiment, a four-element lumped circuit shown in FIG. 12 is used for an electrical model simulating the circulatory arterial system of a human body. The elements of the electrical model are corresponding to four circulatory dynamic parameters:

a blood flow momentum at the proximal section in the arterial system;

a vascular resistance due to blood flow at the proximal section in the arterial system;

a vascular compliance; and a blood flow resistance at the distal section in the arterial system; which are based on the condition of the circulatory system, In the following, the relation between the four elements of the electrical model and the four parameters will be explained.

Inductance L:

the blood flow momentum at the proximal section in the arterial system (dyn·s$^2$/cm$^5$) static electrical capacity C:

the compliance at the proximal section in the arterial system (elasticity) (cm$^5$/dyn)

The compliance refers to the elasticity of the blood vessels to signify their softness.

electrical resistance $R_c$:

the vascular resistance due to blood flow at the proximal section in the arterial system (dyn·s/cm$^5$)

electrical resistance $R_p$:

the vascular resistance due to blood flow at the distal section in the arterial system (dyn·s/cm$^5$)

The electrical currents i, $i_p$, $i_c$, flowing in the various sections of the electrical model correspond to the blood flow rate (cm$^3$/s) in the corresponding sections. The general voltages e(t), applied to the various sections of the model correspond to the pressure (dyn/cm$^2$) at the aorta ascendens. The terminal voltage $V_p$ of the static electrical capacity C corresponds to the blood pressure at the radial artery.

(2) Approximate Formulas of Response in the Model

Next, the response of the electrical model will be theoretically explained with reference to FIG. 12. Firstly, the following differential equation will be formed using the four parameters in the Model shown in FIG. 12, $$e(t) = R_c i + L\frac{di}{dt} + v_p. \tag{1}$$

Here, the current i is:

$$i = i_c + i_p \tag{2}$$

$$= C\frac{dv_p}{dt} + \frac{v_p}{R_p}.$$

Therefore, the above equation (1) can be expressed as:

$$e(t) = LC\frac{d^2 v_p}{dt^2} + \left(R_c C + \frac{L}{R_p}\right)\frac{dv_p}{dt} + \left(1 + \frac{R_c}{R_p}\right)v_p. \tag{3}$$

t is known that the general solution to a differential equation such as the above equation (3) is obtained from the sum of a particular solution satisfying equation (3) and a transient solution satisfying the following equation:

$$0 = LC\frac{d^2 v_p}{dt^2} + \left(R_c C + \frac{L}{R_p}\right)\frac{dv_p}{dt} + \left(1 + \frac{R_c}{R_p}\right)v_p. \tag{4}$$

Next, a method of solving the above equation (4) will be explained. Firstly, suppose that an attenuating wave $V_p$ is expressed as follows:

$$V_p = Ae^{st} \tag{5}$$

Substituting the above equation (5) in the equation (4), $$\left\{LCs^2 + \left(R_c + \frac{L}{R_p}\right)s + \left(1 + \frac{R_c}{R_p}\right)\right\}v_p = 0. \tag{6}$$

Here, we solve the above equation (6) for s as follows:

$$s = \frac{-\left(R_c C + \frac{L}{R_p}\right) \pm \sqrt{\left(R_c C + \frac{L}{R_p}\right)^2 - 4LC\left(1 + \frac{R_c}{R_p}\right)}}{2LC}. \tag{7}$$

If $$\left(R_c C + \frac{L}{R_p}\right)^2 < 4LC\left(1 + \frac{R_c}{R_p}\right), \tag{8}$$

then the value of the root in the equation (7) is negative, and the equation (7) will be expressed as follows:

$$s = \frac{-\left(R_c C + \frac{L}{R_p}\right) \pm j\sqrt{-\left(R_c C + \frac{L}{R_p}\right)^2 - 4LC\left(1 + \frac{R_c}{R_p}\right)}}{2LC} \tag{9}$$

$$= -\alpha \pm j\omega,$$

here, $$\alpha = \frac{R_c + \frac{L}{R_p}}{2LC} \tag{10}$$

$$= \frac{L + R_p R_c C}{2LCR_p}$$

and $$\omega = \frac{-\left(R_c C + \frac{L}{R_p}\right)^2 + 4LC\left(1 + \frac{R_c}{R_p}\right)}{2LC} \tag{11}$$

Next, letting:

$$A_1 = LC, \tag{12}$$

$$A_2 = \frac{L + R_c R_p C}{R_p}, \tag{13}$$

-continued and $$A_3 = \frac{R_c + R_p}{R_p},\quad (14)$$

each of the above equations (10) and (11) will be expressed as follows:

$$\alpha = \frac{A_2}{2A_1} \quad (15)$$

and $$\omega = \sqrt{\frac{A_3}{A_1} - \alpha^2}. \quad (16)$$

Thus, the value s is finally decided, and the solution satisfying the equation (4) can be obtained. In accordance with the above analysis, the equation (5) is utilized as an approximate equation expressing the attenuating and vibrating components, included in the response wave of the electrical model.

Figure 13:
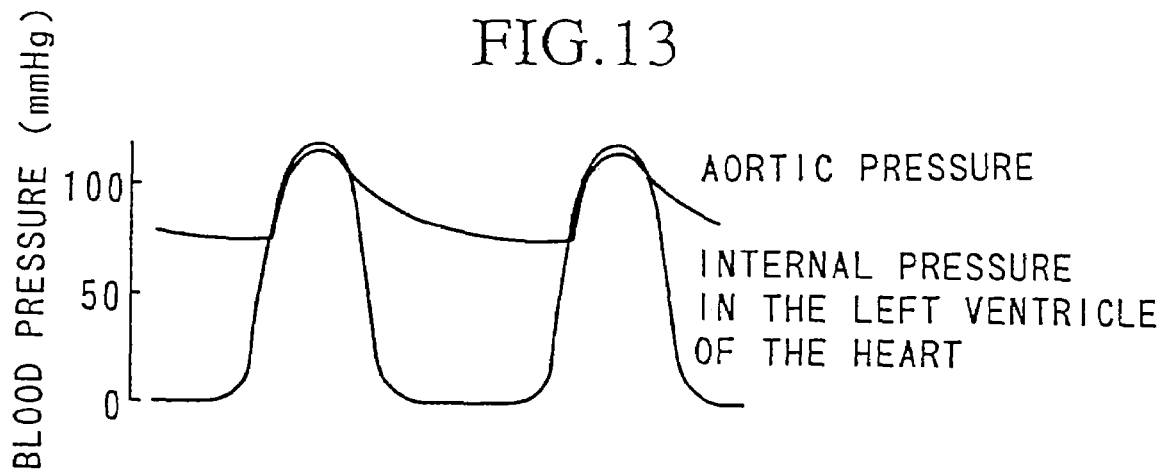
FIG. 13 is an illustration of the blood pressure waveforms at the aorta ascendens and the blood pressure waveforms in the left ventricle of the heart.
Figure 14:
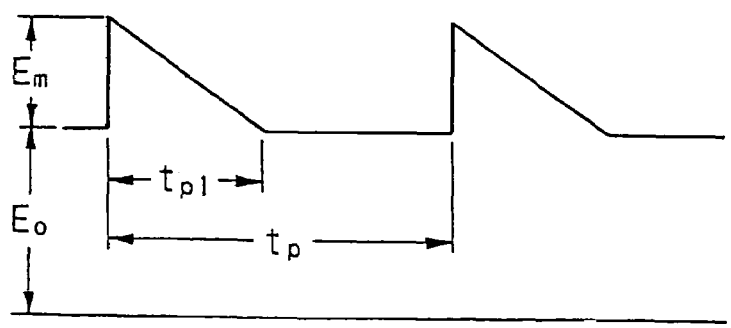
FIG. 14 is an illustration of the electrical signal waveform modeling the blood pressure waveform at the above aorta ascendens.

Next, the blood pressure waves at the aorta ascendens are modeled. FIG. 13 shows general pressure waves at the aorta ascendens. Therefore, we approximate the pressure waves with triangular pulse waves shown in FIG. 14. Letting the amplitude and the time be the voltages $E_0$ and $E_m$ and be the time $t_p$ and $t_{p1}$, the pressure waveform e(t) at a time t can be expressed as follows:

$$e(t) = E_0 + E_m\left(1 - \frac{t}{t_{p1}}\right), \quad (17)$$

when $0 \leq t < t_{p1}$; and $$e(t) = E_0 \quad (18)$$

when $t_{p1} \leq t < t_p$:
where $E_0$ is the voltage to give minimum blood pressure;
($E_0+E_m$) is the voltage to give a maximum blood pressure;
$t_p$ is the period for one pulsation; and
$t_{p1}$ is the period from the point of rise to the minimum point of the blood pressure at the aorta ascendens.

When the waveform e(t), expressed as the above equation (17) and (18), is inputted to the electrical model shown in FIG. 12, the response waveform $V_p(t)$ is:

$$v_p(t) = E_{min} + B\left(1 - \frac{t}{t_b}\right) + D_{m1}e^{-\alpha t}\sin(\omega t + \theta_1) \quad (19)$$

when $0 \leq t < t_{p1}$, $$v_p(t) = E_{min} + D_{m2}e^{-\alpha(t-t_{p1})}\sin\{\omega(t-t_{p1}) + \theta_2\} \quad (20)$$

and when $t_{p1} \leq t < t_p$.

The third term on the right in the equation (19) and the second term on the right in the equation (20) designate the attenuating components (corresponding to the equation (5)), and $\alpha$ and $\omega$ are given by the above equations (15) and (16).

(3) The Relation between Each Element of the Model and Radial Arterial Waveform

Next, other constants in the equations (19) and (20) except $\alpha$ and $\omega$ will be discussed. Firstly, substituting equations (17) and (19) in the above differential equation (3), the following equation (21) can be obtained.

$$E_0 + E_m\left(1 - \frac{t}{t_{p1}}\right) = \left(1 - \frac{R_c}{R_p}\right)(E_{min} + B) - \frac{B}{t_b}\left(R_cC + \frac{L}{R_p}\right)t + \quad (21)$$

$$\left\{LC(\alpha^2 - \omega^2)D_{m1} - \alpha D_{m1}\left(R_cC + \frac{L}{R_p}\right) + D_{m1}\left(1 + \frac{R_c}{R_p}\right)\right\}e^{-\alpha t}\sin(\omega t + \theta_1) +$$

$$\left\{\omega D_{m1}\left(R_cC + \frac{L}{R_p}\right) - 2LC\alpha\omega D_{m1}\right\}$$

$$e^{-\alpha t}\cos(\omega t + \theta_1).$$

For the equation (21) to be valid, the following conditions are necessary, $$E_0 + E_m = \left(1 + \frac{R_c}{R_p}\right)(E_{min} + B) \quad (22)$$

$$= E_0 + A_3B - \frac{B}{t_b}A_2,$$

$$\frac{E_m}{t_{p1}} = \frac{B}{t_b}\left(1 + \frac{R_c}{R_p}\right) \quad (23)$$

$$= \frac{B}{A_3t_b},$$

$$LC(\alpha^2 - \omega^2) - \alpha\left(R_cC + \frac{L}{R_p}\right) + \left(1 + \frac{R_c}{R_p}\right) = 0 \quad (24)$$

and $$R_cC + \frac{L}{R_p} = 2LC\alpha. \quad (25)$$

Because $\alpha$ and $\omega$ are given by the above equations (15) and (16), it is natural that $\alpha$ and $\omega$ satisfy equations (24) and (25).

Secondly, substituting equations (18) and (20) in the above differential equation (3), the following equation (26) can be obtained:

$$E_0 = \left(1 + \frac{R_c}{R_p}\right)E_{min} + \left\{LC(\alpha^2 - \omega^2)D_{m2} - \alpha D_{m2}\left(R_cC + \frac{L}{R_p}\right) + \quad (26)\right.$$

$$\left(1 + \frac{R_c}{R_p}\right)\right\}e^{-\alpha(t-t_{p1})}\sin\{\omega(t-t_{p1}) + \theta_2\} +$$

$$\left\{\omega D_{m2}\left(R_cC + \frac{L}{R_p}\right) - 2LC\alpha\omega D_{m2}\right\}e^{-\alpha(t-t_{p1})}$$

$$\cos\{\omega(t - t_{p1}) + \theta_2\}.$$

For the equation (26) to be valid, in addition to the equations (23) and (24), the following equation (27) must be satisfied that:

$$E_0 = \left(1 + \frac{R_c}{R_p}\right)E_{\min} \quad (27)$$
$$= A_3 E_{\min}.$$

The constants in the equations (19) and (20) will be computed in accordance with the above equations (22)~(25) and (27) which define the differential equation (3). From equation (27), $$E_{\min} = \frac{E_0}{A_3}. \quad (28)$$

While, from equation (23), B is expressed as follows:

$$B = \frac{E_m I_b}{A_3 t_{p1}}. \quad (29)$$

Here, substituting the equation (29) in the equation (22), $t_b$ is expressed as follows:

$$I_b = \frac{A_3 t_{p1} + A_2}{A_3}. \quad (30)$$

Next, the remaining constants $D_{1m}$, $D_{2m}$, $\theta_1$ and $\theta_2$ are selected so that the radial arterial waveform $v_p$ can be contiguous at $t=0$, $t_{p1}$, and $t_p$. In other words, the values are selected so as to satisfy the following conditions (a)~(d).

(a) the coincidence of $v_p(t_{p1})$ in the equation (19) with $v_p(t_{p1})$ in the equation (20)
(b) the coincidence of $v_p(t_p)$ in the equation (20) with $v_p(0)$ in the equation (19)
(c) the coincidence of the differential coefficient in the equation (19) with one in the equation (20) when $t=t_p$
(d) the coincidence of the differential coefficient it in the equation (19) at $t=0$ with the differential coefficient in the equation (20) at the time $t=t_p$ That is, the values of $D_{1m}$ and $\theta_1$ are as follows:

$$D_{1m} = \frac{\sqrt{D_{11}^2 + D_{12}^2}}{\omega}, \quad (31)$$

$$\theta_1 = \tan^{-1}\frac{D_{11}}{D_{12}}, \quad (32)$$

where $$D_{11} = (v_{01} - B - E_{\min})\omega \quad (33)$$

$$D_{12} = (v_{01} - B - E_{\min})\alpha + \frac{B}{t_b} + \frac{i_{01}}{C}. \quad (34)$$

Here, $v_{01}$ is the initial value of $v_p$ and $i_{01}$ is the initial value of $i_p$ when $t=0$.

Also, the values of $D_{2m}$ and $\theta_2$ are as follows:

$$D_{2m} = \frac{\sqrt{D_{21}^2 + D_{22}^2}}{\omega} \quad (35)$$

$$\theta_2 = \tan^{-1}\frac{D_{21}}{D_{22}}, \quad (35)$$

where $$D_{21} = (v_{02} - E_{\min})\omega \quad (36)$$

$$D_{22} = (v_{02} - E_{\min})\alpha + \frac{i_{02}}{C}. \quad (37)$$

Here, $V_{02}$ is the initial value of $v_p$ and $i_{02}$ is the initial value of $i_c$ when $t=t_{p1}$. The constants in the equation (19) and (20) are thus obtained.

Thirdly, by back-computing the angular frequency $\omega$ in the equation (16), the blood resistance $R_c$ at the artery center can be expressed as follows:

$$R_c = \frac{L - 2R_p\sqrt{LC(1 - \omega^2 LC)}}{CR_p}. \quad (39)$$

The condition necessary to make the resistance $R_c$ real and positive that:

$$\frac{4R_p^2 C}{1(2\omega R_p C)^2} \le L \le \frac{1}{\omega^2 C}. \quad (40)$$

Generally, the $R_p$ is at a level of about $10^3$ (dyn·s/cm$^5$) and the C is about $10^{-4}$ (cm$^5$/dyn), and because the $\omega$ is the angular frequency of the vibration component superimposed on the arterial pulse waves, the angular frequency $\omega$ can be considered to be over 10 (rad/s), and therefore the lower limit value of the equation (40) can be regarded as $1/\omega^2 C$. For simplification, L can be approximated by:

$$L = \frac{1}{\omega^2 C}, \quad (41)$$

then the resistance $R_c$ becomes:

$$R_c = \frac{L}{CR_p}. \quad (42)$$

Using equations (41) and (42), the attenuation constant $\alpha$ in the equation (15) is expressed as follows:

$$\alpha = \frac{1}{CR_p}. \quad (43)$$

Using the equations (41)~(43) and either $\alpha$, $\omega$ or one of the four parameters, for example L, the other parameters $R_c$, $R_p$ and C are expressed as follows:

$$R_c = \alpha L, \quad (44)$$

$$R_p = \frac{\omega^2 L}{\alpha}, \quad (45)$$

$$C = \frac{1}{\omega^2 L}. \quad (46)$$

It is clear that the parameters of the model are finally decided by $\alpha$, $\omega$ and L based on the equations (44)~(46).

Here, $\alpha$ and $\omega$ can be obtained by the actual measured waveforms of the radial arterial pulse waves. On the hand, L can be computed from the stroke volume SV per one pulsation (beat).

Next, the process of computing L based on the stroke volume SV will be explained. Firstly, the average $E_{01}$ of the pressure wave at the aorta ascendens is given by $$E_{01} = \frac{E_0 t_p + \frac{E_m t_{pl}}{2}}{t_p}. \quad (47)$$

On the hand, the $R_c$, $R_p$, $\alpha$, $\omega$ and L are related by the following equation:

$$R_c + R_p = \alpha L + \frac{\omega^2 L}{\alpha} = \frac{(\alpha^2 + \omega^2)L}{\alpha}. \quad (48)$$

Next, the average current through the four parameters model, that is the value of the average $E_{01}$ divided by ($R_c+R_p$), corresponds to an average value of a blood flow (SV/$t_p$) in the artery caused by the heart pulsing motion. Therefore, $$\frac{SV}{t_p} = 1333.22 \cdot \frac{\alpha\left(E_0 t_p + \frac{E_m t_{pl}}{2}\right)}{(\alpha^2 + \omega^2)L t_p} \quad (49)$$

where the (1333.22) is the coefficient for conversion in the pressure unit from (mmHg) to (dyn/cm$^2$).

The given equation (49) is solved for L, then the following can be obtained to compute L from the stroke volume SV.

$$L = 1333.22 \cdot \frac{\alpha\left(E_0 t_p + \frac{E_m t_{pl}}{2}\right)}{(\alpha^2 + \omega^2)SV}. \quad (50)$$

It is possible to obtain the inductance L by measuring the blood flow rate to determine the value to correspond to the average current:

$$\frac{1}{t_p}\left(E_0 t_p + \frac{E_m t_{pl}}{2}\right)$$

in the above equation (49). The known methods of measuring the blood flow rate are impedance method and Doppler method. The Doppler method can be performed by either ultrasound or laser.

(4) Expansion of the Electrical Model

Figure 26:
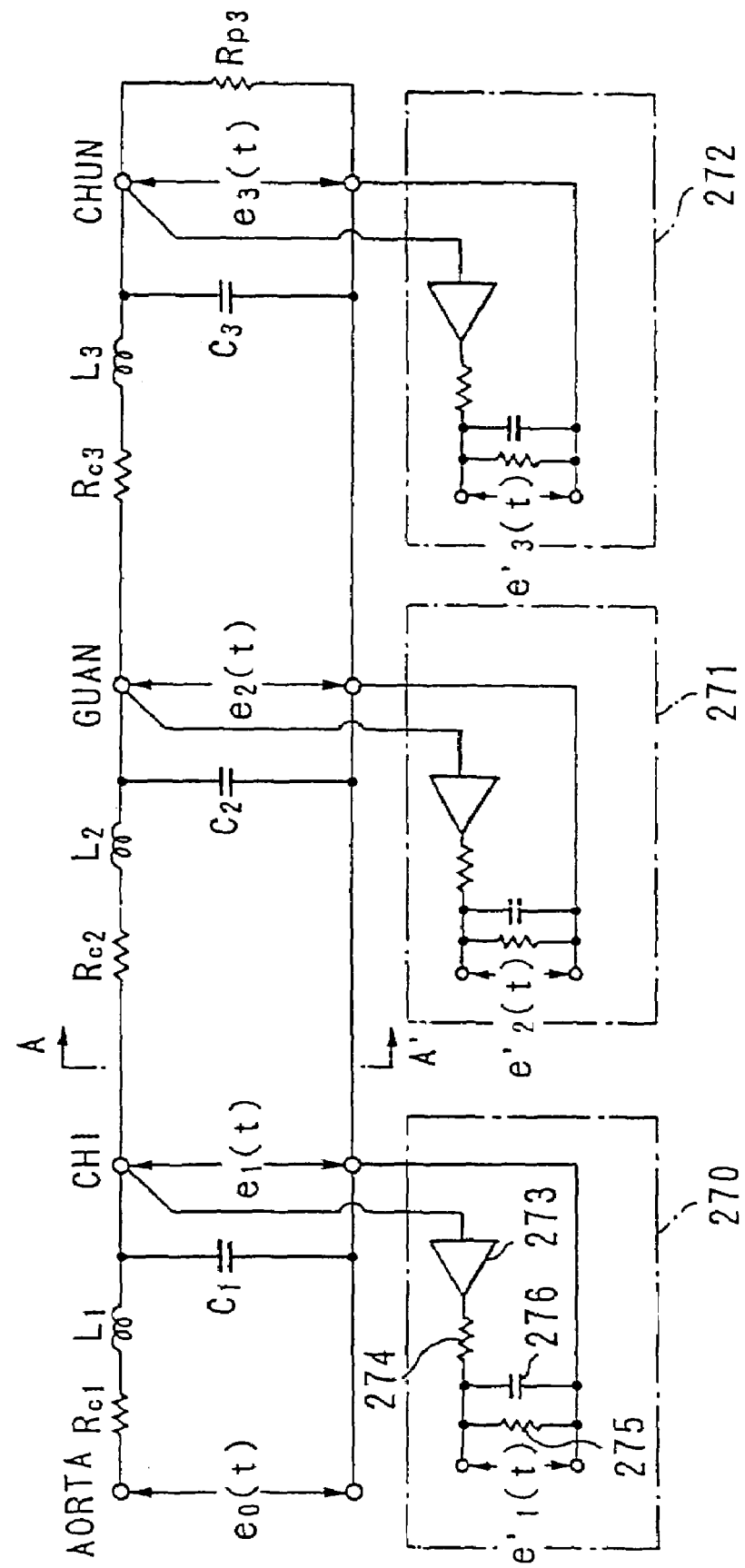
FIG. 26 is a circuit diagram representing the expansion of the lumped four parameter circuit model for the arterial system.

Next, the Model shown in FIG. 12 can be expanded to consider the pressure variations at the locations of Chun, Guan and Chi, then a circuit shown in FIG. 26 is obtained.

In this figure, the pressures at the aorta ascendens, Chi, Guan and Chun are expressed by the general voltages $e_o(t)$, $e_1(t)$, $e_2(t)$ and $e_3(t)$, respectively, and the inductance $L_1 \sim L_3$, representing the inertia of the blood, the static electrical capacity $C_1 \sim C_3$, representing the vascular compliance and the resistances $R_{c1} \sim R_{c3}$, representing the resistance of the blood vessels are connected between the voltage measuring terminals.

Also, the electrical resistance $R_p$ in FIG. 12 represents the vascular resistance in further distal blood vessels than the arterial distal blood vessel which are to be measured. Therefore, in the Model presented in FIG. 26, the electrical resistance shown $R_p$ in FIG. 12 corresponds to the combined impedance in the later stages of the circuit. For example, in FIG. 26, if the combined impedance to the right side of the single dot line A-A' is equated to the electrical resistance $R_p$, the model in FIG. 26 becomes the same as the Model in FIG. 12.

Therefore, in the Expansion Model shown in FIG. 26, it is possible to obtain the values of the elements of the Expansion Model by the same technique employed in the Model in FIG. 12. That is, if the combined impedance to the right side of the single dot line A-A' is equated to the electrical resistance $R_p$, according to the method presented above, the parameters $R_{c1}$, $L_1$ and $C_1$ are obtained on the basis of the waveforms of the general voltages $e_o(t)$ and $e_1(t)$, similarly the parameters $R_{c2}$, $L_2$ and $C_2$ are obtained on the basis of the waveforms of the general voltages $e_1(t)$ and $e_2(t)$, and similarly the parameters $R_{c3}$, $L_3$, $C_1$ and $R_{p3}$ are obtained on the basis of the waveforms of the general voltages $e_2(t)$ and $e_3(t)$.

In the above explanation, the waveforms corresponding to the general voltages $e_1(t) \sim e_3(t)$ are assumed to represent the at-source blood pressure directly. However, in practice, the waveforms, generated in the blood vessels of the examinee, are changed while being propagated through the muscles, fat tissues and skin of the examinee before being detect by the strain gages 252~254.

Therefore, in order to carry out more detailed analysis, it is necessary to consider the pressure waveforms. It is suggested that, in such a case, it would be suitable to provide a pressure waveform transformation circuits 270~272 as shown in FIG. 26. In the circuit 270, the numeral 273 represents a voltage follower circuit; 274, 275 are electrical resistances, 276 is a condenser. The electrical resistances 274, 275 simulate the blood pressure drop between the strain gage 254 and the location to correspond to the Chi of the artery of the examinee. The electrical resistance 275 and the condenser 276 simulate the frequency response, i.e. the decay in the high frequency waveforms. The voltage follower circuit 273 is provided before the electrical resistance 274 because it is considered that the effects of the muscle, fat tissues and skin on the artery itself is slight. In this model, the voltage $e_1(t)$ is transformed by the pressure waveform transformation circuit 270 and is detected as $e_1'(t)$. Therefore, to obtain the correct waveform of the voltage $e_1$, it is necessary to obtain the constants for each element in the pressure waveform transformation circuit 270. This is possible by applying sound signals of various frequencies and waveforms to the examinee's arm, and analyzing the attenuation and changes in such sound signals. That is, because the configuration of the circuit of the pressure waveform transformation circuit 270 is the same as the Model shown in FIG. 12, the same method can be used. Here, it should be noted that the values in the circuit 270 are not fixed, and change in accordance with the finger pressures of the examiner; therefore, it is preferable to record the results of applying various sound signals under various finger pressure on the examinee's arm, so as to relate the constants to the various pressing pressures.

The above descriptions provided an explanation of the relationship among the radial arterial waveforms, stroke volume and each of the elements in the electrical Model. The microcomputer 204 (See FIG. 10) in this embodiment computes the values of the parameters in the model in accordance with the relationship presented in the foregoing.

Chapter 2-2: Operation of the Apparatus

Figure 20:
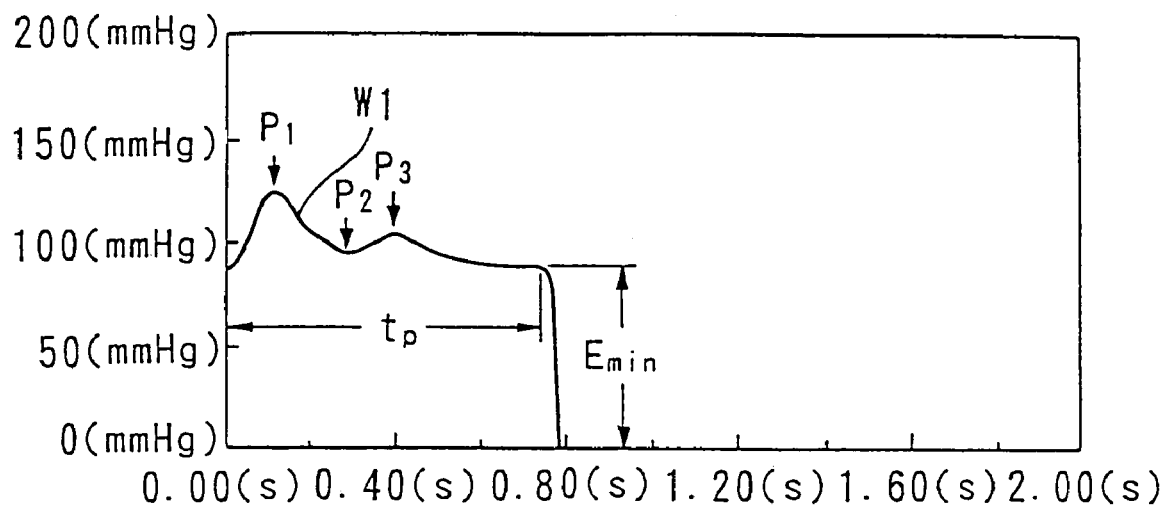
FIG. 20 is an example waveform showing the radial arterial waveform obtained by an averaging process.
Figure 21:
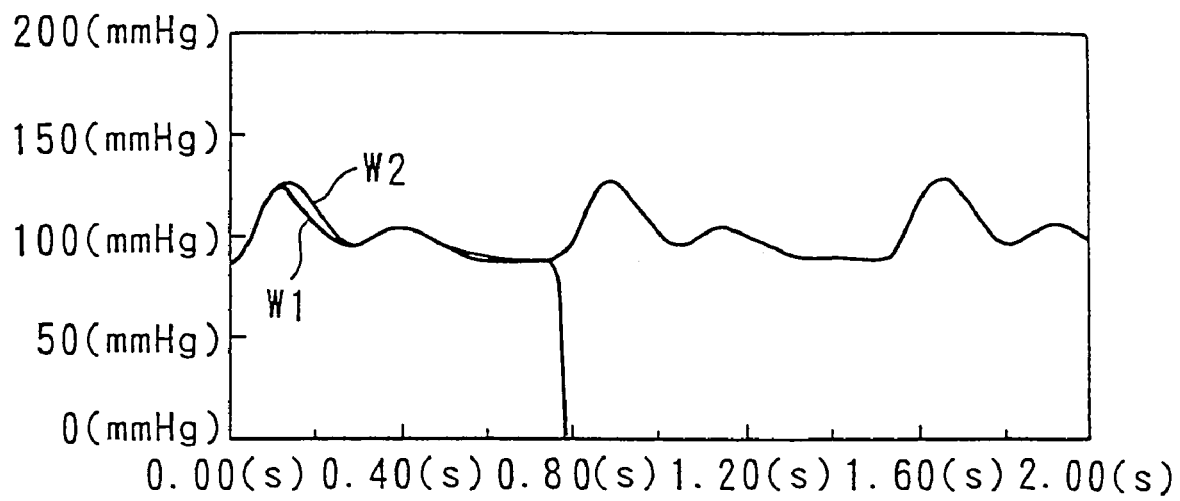
FIG. 21 is an illustration of the overlap display of a radial arterial waveform obtained by the averaging process and a radial arterial waveform obtained by the computation processing.

FIGS. 15 to 19 show flowcharts for the operation of the waveform analysis apparatus. FIG. 20 shows the waveforms of the radial artery obtained by the averaging process, FIG. 21 shows the comparison between the radial artery waveforms W1 obtained by the averaging process and the radial artery waveforms W2 obtained by the parameter computation. The following explanations are provided with reference to these figures.

Chapter 2-2-1: Ordinary Computation Procedure (1) Reading of Pulse Wave Data

The computation of the circulatory dynamic parameters is performed by: attaching the cuff belt S2 to the examinee as shown in FIG. 11; attaching the pulse wave sensor S1 to the hand of the examiner; pressing down the switch 266a (see FIG. 25); and inputting various commands through the keyboard 205. In response to these commands, the microcomputer 204 sends a command to begin measurements of the pulse waves to the pulse wave detection apparatus 201. The pulse wave detection apparatus 201 receives the radial artery pulse wave signals through the strain gages 252~254, and the sequential digital signals expressing the radial pulse waves are outputted from the A/D converter 203, and the microcomputer 204 takes in the readings for a set period of time (about one minute). Thus the microcomputer 204 accumulates sequential digital signals of the plurality of waveforms of the pulsation's.

(2) Averaging Process

Next, the microcomputer 204 computes an average waveform during the one-minute-period based on the plurality of waveforms of the radial artery, and stores this waveform as the representative waveform of the radial artery in the internal memory (step S1). At the same time, averaging is performed on the finger pressures detected via the decrementor 267 (see FIG. 25). A representative waveform W1 of the radial artery stored in the memory is shown in FIG. 20.

(3) Stroke Volume Computation

When the above averaging process is completed, the microcomputer 204 sends out a command to activate the stroke pulsing volume determination device 202. The results of the measurement data per pulsation is forwarded to the microcomputer 204 (step S2).

(4) Parameter Computation Process

Figure 16:
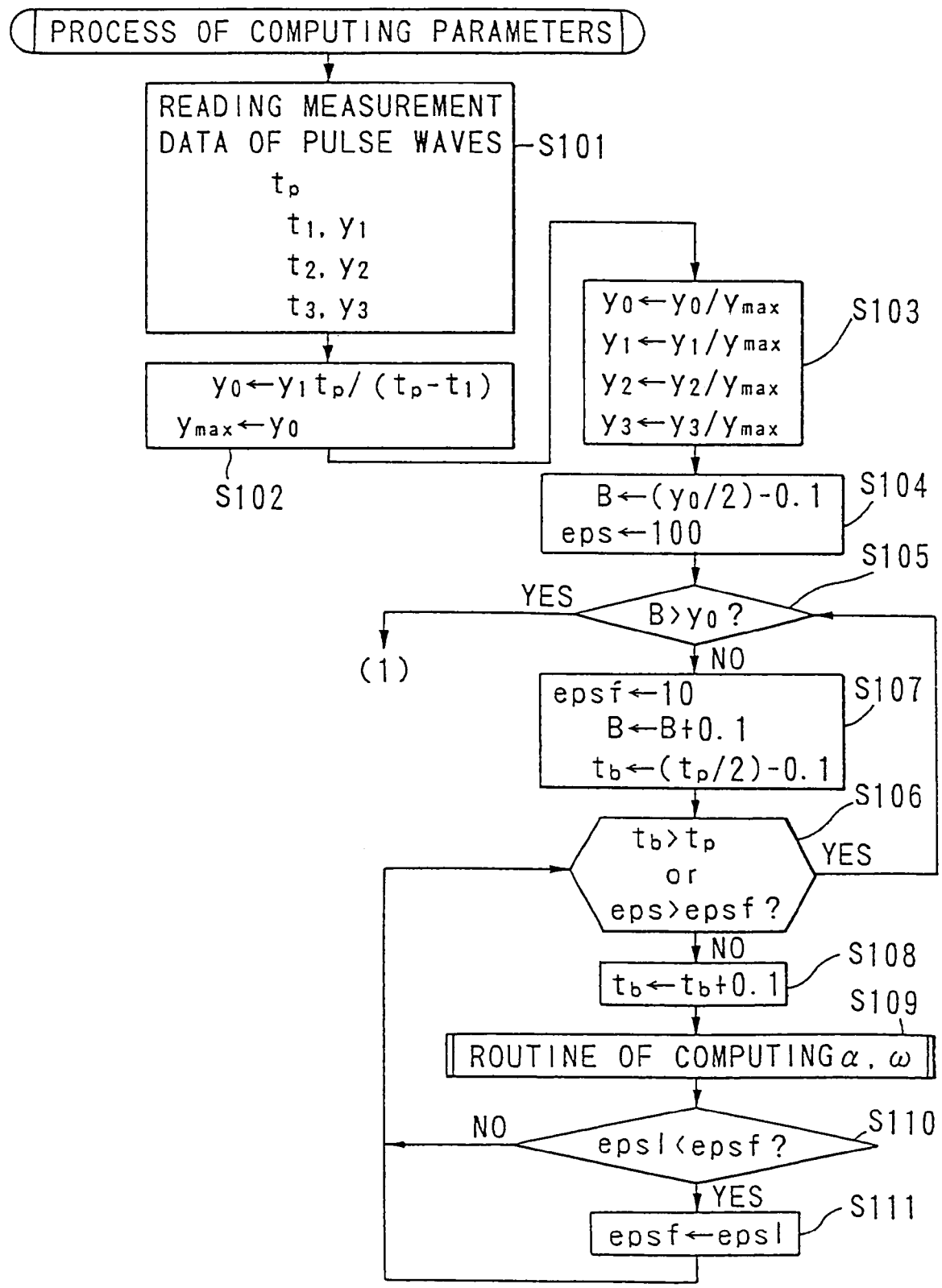
FIG. 16 is a flowchart showing the routine for the operation of the embodiment.
Figure 17:
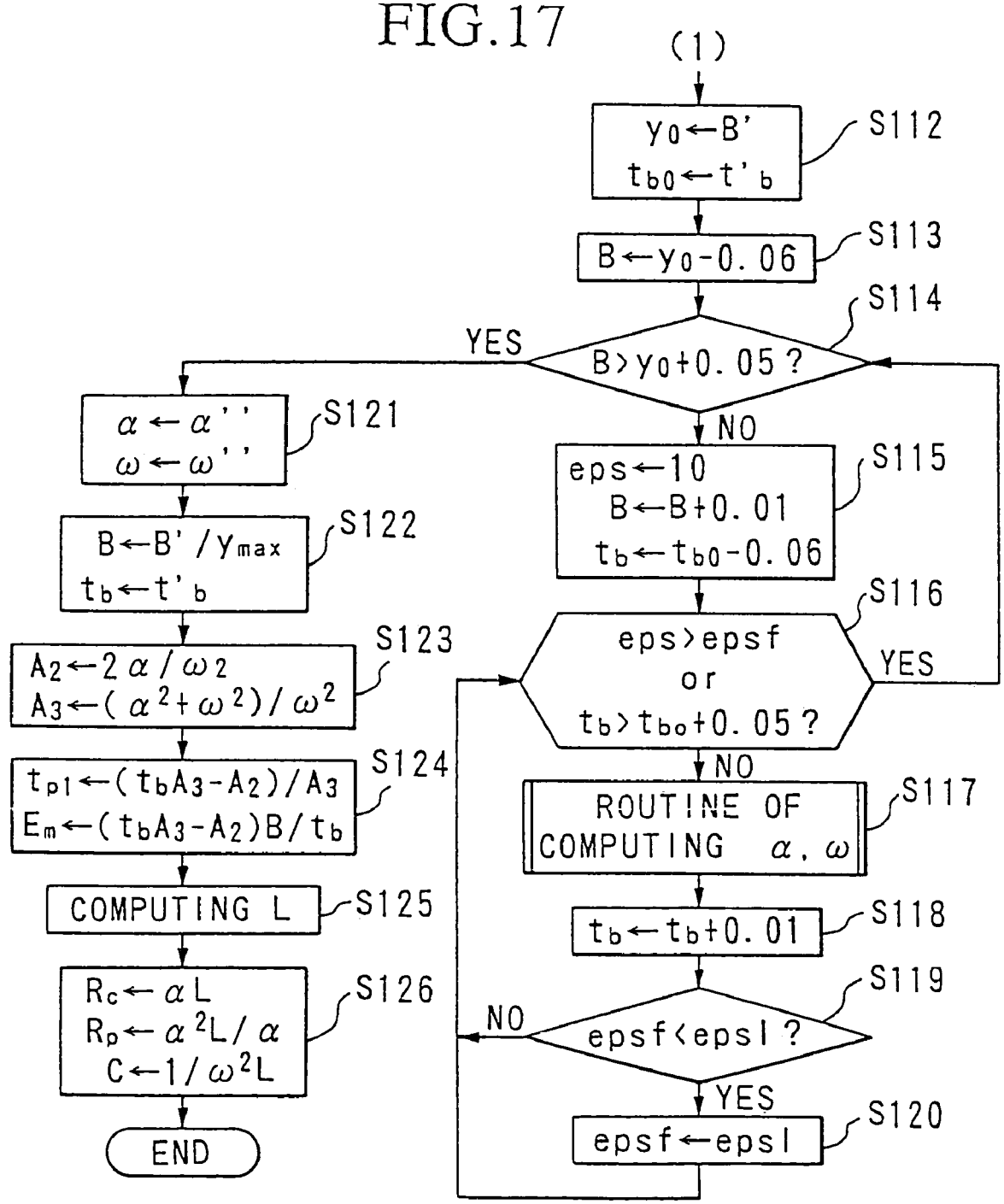
FIG. 17 is a flowchart showing the routine for the operation of the embodiment.
Figure 18:
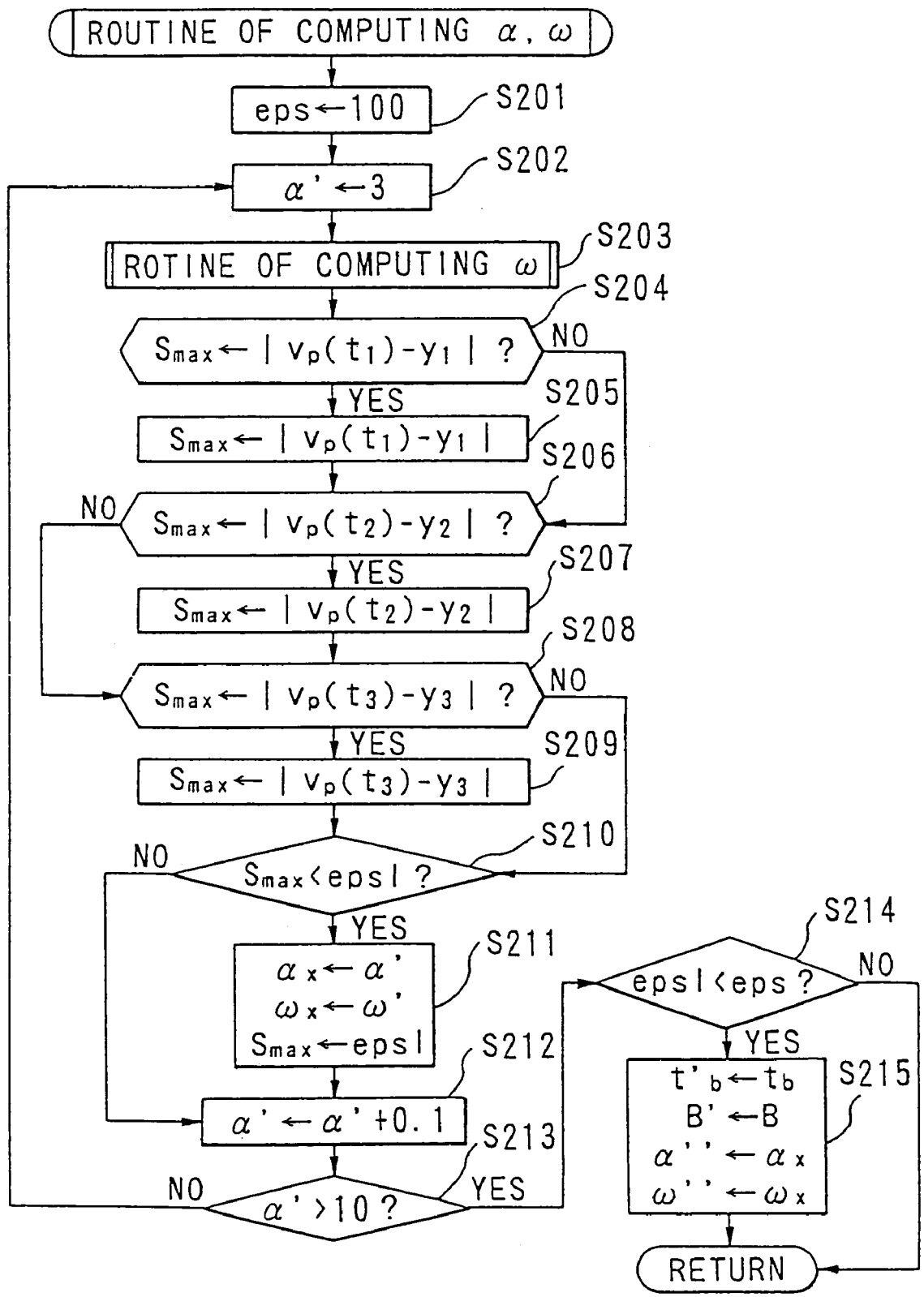
FIG. 18 is a flowchart showing the routine for the operation of the embodiment.
Figure 19:
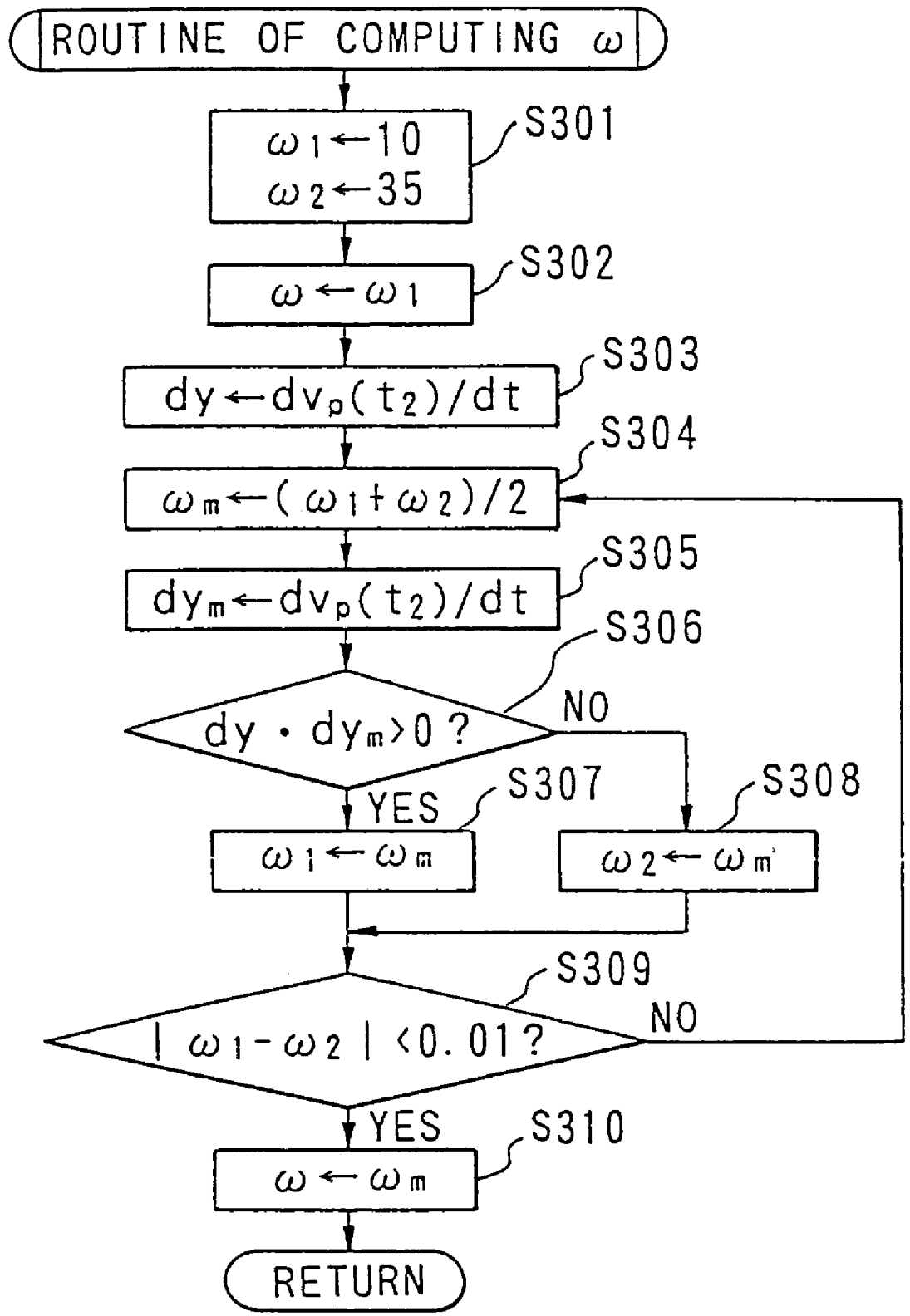
FIG. 19 is a flowchart showing the routine for the operation of the embodiment.

Next, the processing by the microcomputer 204 proceeds to step S3, and performs the parameter computation routine whose flowcharts are shown in FIGS. 16 and 17. With the execution of this routine, the routine of computing α and ω (steps S109 and S117) shown in FIG. 18, is executed for each of the Chun, Guan and Chi locations. With the execution of these α and ω computing routines, the ω computing routine is performed (step S203). To simplify the explanation, it is assumed that the pressure waveforms corresponding to the electrical voltages $e_1(t) \sim e_3(t)$ in FIG. 26 are obtained directly from the strain gages 252~254.

The following is an explanation of the routines described above.

First, the microcomputer 204 examines the radial artery waveforms per pulse in the memory, and determines the first point $P_1$ in terms of the time $t_1$ and blood pressure level $y_1$ corresponding to the maximum blood pressure; the second point $P_2$ in terms of the time $t_2$ and blood pressure level $y_2$ corresponding to the temporary drop in the blood pressure; and the third point $P_3$ in terms of the time $t_3$ and blood pressure $y_3$ corresponding to the next rise in the blood pressure. Also, the microcomputer 204 determines the time duration $t_p$, the minimum blood pressure value $E_{min}$ (which corresponds to the 1st term of each of the equations (3) and (4)) with respect to one pulsation of the radial arterial waveforms in the memory (step S101). The above processing produces the following data, for example, necessary for the parameters computation.

First Point: $t_1$=0.104 s, $y_1$=123.4 mmHg
Second Point: $t_2$=0.264 s, $y_2$=93.8 mmHg
Third Point: $t_3$=0.380 s, $y_3$=103.1 mmHg
Pulse duration: $t_p$=0.784 s
Min. Press: $E_{min}$=87.7 mmHg
Stroke vol.: SV=103.19 cc/beat In this case, when the pulse waveform is such that it is difficult to distinguish the second point $P_2$ from the third point $P_3$, then the times for the point $P_2$ and $P_3$ are chosen as $$t_2 = 2t_1, t_3 = 3t_1,$$

and the blood pressure value is determined at these points.

Figure 22:
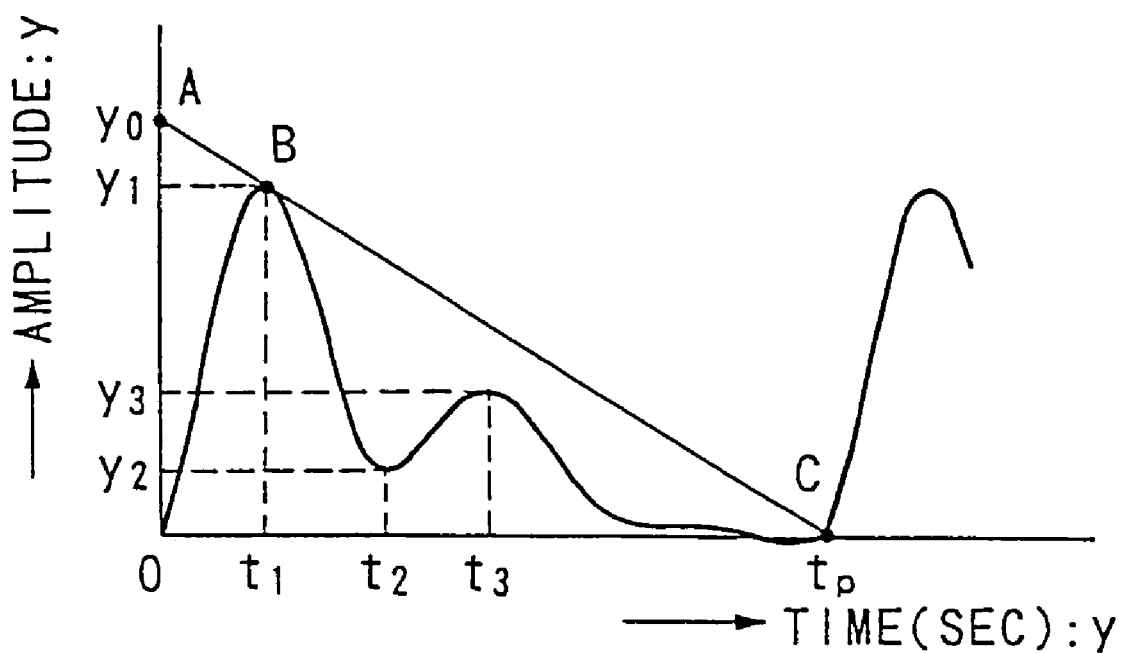
FIG. 22 is an example of the radial arterial waveform obtained by the averaging process.

To simplify the calculations, using the value of the blood pressure $y_o$ at the point A shown in FIG. 22, $y_1$ to $y_3$ are normalized in steps S102, 103, and the initial value of B is determined as:

$$\frac{y_0}{2} - 0.1$$

in step S104.

Next, the optimum values of the B, $t_b$, α and ω are obtained by the following steps.

(a) First, B is varied between $y_0/2$ to $y_0$, and simultaneously is varied between $t_p/2$ to $t_p$ at an interval of +0.1, and the values of B, $t_b$, α and ω are determined so as to minimize $V_p(t_1)-y_1$, $v_p(t_2)-y_2$ and $v_p(t_3)-y_3$.

(b) For the values of B, $t_b$, α and ω, the values of B, $t_b$, α and ω are determined so as to minimize the values of $V_p(t_1)-y_1$, $v_p(t_2)-y_2$ and $v_p(t_3)-y_3$.

(c) Based on the values of the B and $t_b$, repeat the steps (a) and (b) within the range of B $$B \pm 0.05, t_b \pm 0.05$$

(d) In the above process (a), (b) and (c), the value of α is varied in increments of 0.1 between 3 to 10 to calculate the optimum values of ω for each α.

The values of ω for α are determined so as to make $$\frac{dv_p(t_2)}{dt} = 0$$

by the binary method (refer to FIG. 10). Furthermore, the values of $v_p$ are calculated with the initial value of $v_{01}$=0.

According to the above procedure, the following example values are determined.

$\alpha=4.2$ (s$^{-1}$); $\omega=24.325$ (rad/s);

$B=27.2$ (mmHg); $t_b=0.602$ (s)

(e) Next, the values of $t_{p1}$, $E_m$ and $E_0$ are calculated from the equations (28)~(30), and (44)~(46) in steps S123, S124. The results of this example is shown below.

$t_{p1}=0.588$(s)

$E_m=46.5$ mmHg $E_0=90.3$ mmHg (f) Next, using the equation (50), the value of L from the pulsing volume rate in step S125, and the remaining parameters are obtained from the equations (44)~(46) in step S126. The following examples values are obtained.

$L=7.021$ (dyn·s$^2$/ cm$^5$)

$C=2.407\times10^{-4}$ (cm$^5$/dyn)

$R_c=29.5$ (dyn·s/cm$^5$)

$R_p=989.2$ (dyn·s/cm$^5$)

Also, total direct current resistance (averaging) value TPR (Total Peripheral Resistance) is obtained by the following equation.

$TPR=R_c+R_p=1018.7$ (dyn·s/cm$^5$)

(5) Output Processing

When the above discussed parameter processing is completed, the microcomputer 204 outputs the values of L, C, $R_c$ and $R_p$ from the output device in step S4. That is, for each waveform from the Chun, Guan, Chi sections, the above computation processes are performed, and the values of the parameters $L_1$ to $L_3$, $C_1$ to $C_3$, $R_{c1}$ to $R_{c3}$ shown in FIG. 26 are obtained.

For confirmation, the parameter values computed are put in equation (40), then $6.696 \leq L \leq 7.021$ is obtained, and the approximation by equation (41) appears to be proper. Also, as shown in FIG. 21, the radial arterial waveforms calculated from the parameter values are quite similar to those actually observed by averaging over one minute period.

Chapter 2-2-2: Continuous Computation

Figure 15:
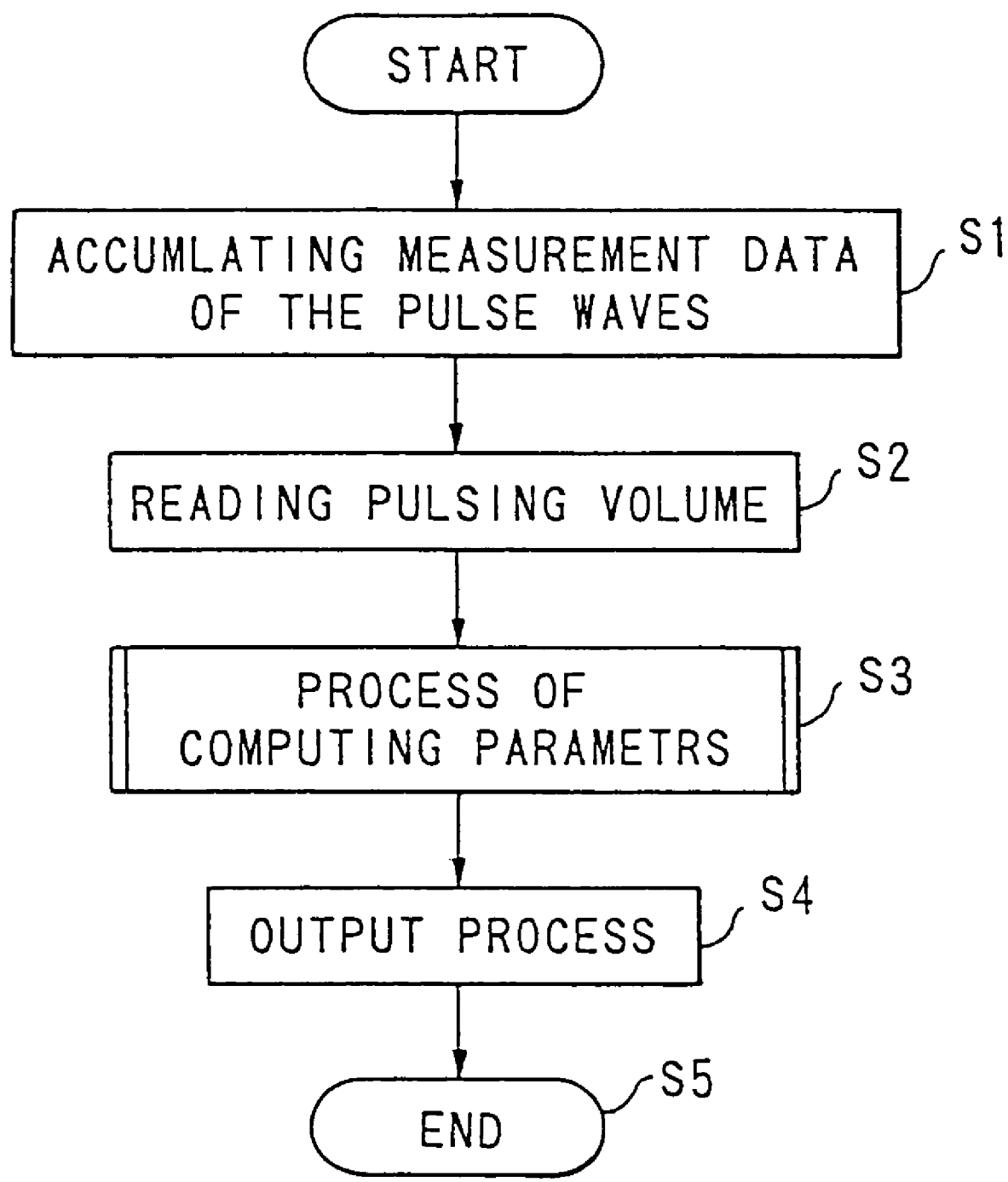
FIG. 15 is a flowchart showing the routine for the operation of the second embodiment.

The embodiment according to this invention is provided with a timer, and it is possible to measure the circulatory dynamic parameters continuously over a prolonged period of time. To perform continuous measurements, the examiner inputs a command for continuous measurement through the keyboard 205. When the resulting step S4 (output process) shown in FIG. 15 is completed, the timer is set, and after a set time has elapsed, the steps from S1 are re-executed, the parameters are computed in step S3, and the results are recorded in a recording medium in step S4. By repeating this process, the continuous computations of the parameters are performed.

The examiner may alter the finger pressure suitably after each elapsing of a set time period. That is, in a general pulse examination, the examiner alters his finger pressure suitably to obtain information on various items, therefore the present embodiment may also be used in conjunction with such an examination procedure. By so doing, it becomes possible to obtain various data in accordance with the varying finger pressures.

Chapter 2-3: Variations of the Second Embodiment

In addition to the second embodiment presented above, the following variations may be practiced.

Variation (i)

The circulatory dynamic parameters for the radial artery may be obtained without measuring the stroke volume, and assuming the value of L. To supplement lowering of the computational accuracy, the embodiment may be configured so as to have an overlap display of the computed and measured radial artery waveforms as shown in FIG. 21, and to have the examiner enter various values of L. In such an embodiment, the examiner performs trial and error process of optimizing the value of L to obtain matching of the two waveforms.

Variation (ii)

Figure 23:
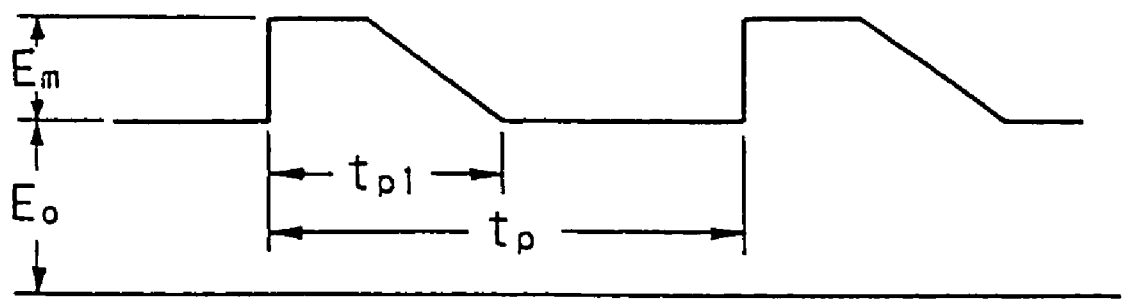
FIG. 23 is an illustration of the other electrical signal waveform modeling the blood pressure waveform at the above aorta ascendens.

As a model of the radial artery waveform, a waveform shown in FIG. 23, a step-and-ramp waveform may be chosen instead of a triangular waveform. This form is closer to the true waveform than the triangular waveform, and more accurate representation for the circulatory dynamic parameters is obtainable.

Variation (iii)

In the above embodiment, the dynamic parameters were obtained by means of equations and computations, the waveforms may be simulated by varying the parameters within ranges by a simulation circuitry, and the parameters which represent the measured waveforms most accurately may be outputted. In this case, more complex electrical models for the arterial system and for the pressure waveforms for the aorta ascendens may be chosen to obtain more accurate representation of the actual performance, and the measurement accuracy can be improved.

Variation (iv)

The measurement locations for the radial artery and the stroke volume are not limited to those shown in FIG. 11. For example, by providing blood pressure sensor on the rubber glove 251, both the radial arterial waveforms and the stroke volume may be determined simultaneously. In this case, the examinee does not need to roll up the sleeves, and it is more convenient, in some cases.

Similarly, the stroke volume determination device may be made on arm, hand or finger on the arm opposite to the pulse taking arm.

Variation (v)

In the above embodiment, to simplify the explanation, the waveforms corresponding to the voltages $e_1$~$e_3$ were assumed to be obtained directly from the strain gages 252~254, but it is permissible to examine using a model that incorporates the model for the pressure waveform transformation circuits 270~272.

Chapter 3: A diagnostic Apparatus Based on Distortions in the Pulse Waveforms

Next, a diagnostic apparatus according to a third embodiment of the present invention will be explained. This apparatus first determines the distortions of the detected pulse waveforms obtained from an examinee.

The distortion in the waveforms refers to deviations from the "normal" pulse waveform shape of a living body, and the waveform shape is obviously closely related to the conditions of the living body, and therefore, computations of distortions in the waveforms serve as an excellent guide to diagnostics.

As will be described later in this Chapter, the waveform distortions are also related to the circulatory dynamic parameters described in Chapter 2, and therefore, computations of the waveform distortions will also serve as indicators for circulatory dynamic parameters, and will enable diagnosis to be performed based on computed distortions.

In this Chapter, the relationship between waveform distortions and waveform types/circulatory dynamic properties will be explained first, followed by the presentation of a diagnostic apparatus of a third embodiment which utilizes this relationship, and a variation of the third embodiment.

Chapter 3-0: Relationship between Distortion, Pulse Waveform Shape and Dynamic Parameters Before explaining the operations of the pulse wave diagnostic apparatus of this invention, the relationship between the waveform distortion, the pulse waveform shape and circulatory dynamic parameters will be explained with reference to the drawings provided on the basis of the inventors experience.

In the following embodiment, the distortion factor d is defined as follows:

$$d = \frac{\sqrt{Q_2^2 + Q_3^2 + \ldots + Q_n^2}}{Q_1}$$

where $Q_1$ is the amplitude of the fundamental wave;
$Q_2$ is the amplitude of the 2nd harmonics; and
$Q_n$ is the amplitude of the nth harmonics in the Fourier analysis of the pulse waves.

Chapter 3-0-1: Relationship Between Waveform Distortion and Waveform Shape

First, the relationship between the waveform distortion and waveform shapes of the pulse waves will be explained.

Figure 31A:
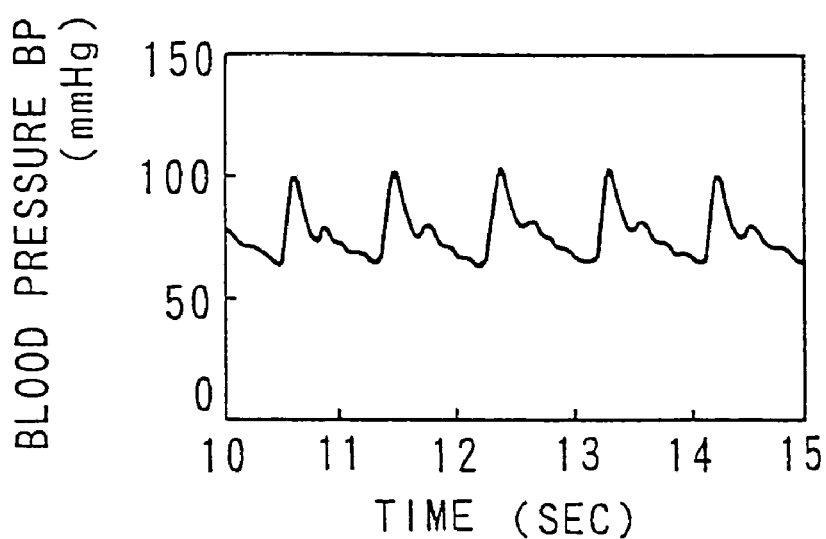
FIG. 31A is a typical waveform of Ping mai type.
Figure 31B:
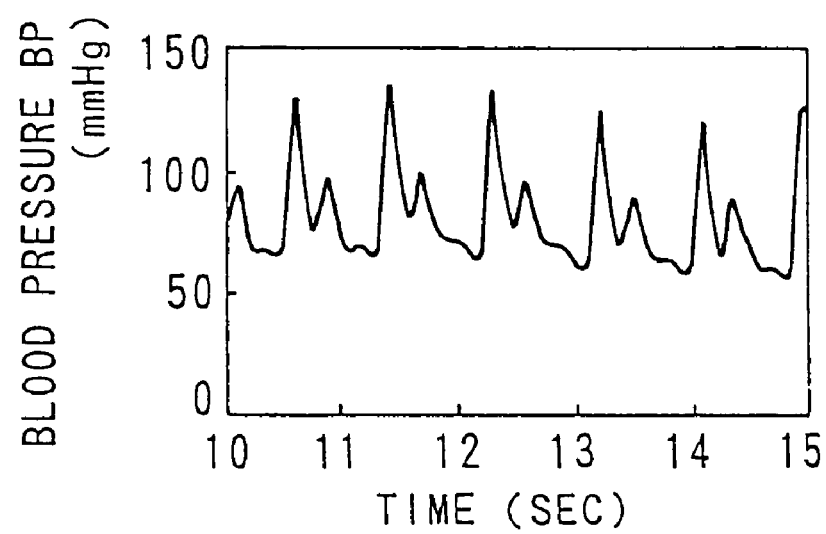
FIG. 31B is a typical waveform of Hua mai type.
Figure 31C:
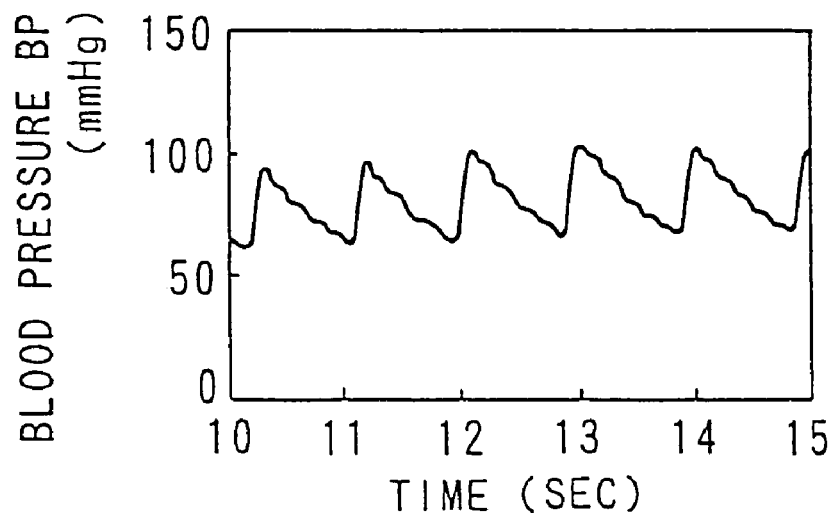
FIG. 31C is a typical waveform of Xuan mai type.

From a variety of shapes of pulse waveforms, those defined as Ping mai type, Hua mai type and Xuan mai type waveforms are typically illustrated in FIGS. 31A, 31B and 31C, respectively. The graphs show blood pressure BP in mmHg plotted on the vertical axis and the time in seconds plotted on the horizontal axis.

The Ping mai is typical shape of a healthy adult, and the waveform shown in FIG. 31A is from a 34-year-old male. The Ping mai type waveform is characterized by a gentle double peak waveform having a regular rhythm, and is free of irregularities.

The Hua mai is caused by hemodynamic irregularities, and is symptomatic of an illness causing rapid pulsations of the heart. A typical example shown in FIG. 31B is from a 28-year-old male patient. The Hua mai type waveform is characterized by a rapid rise and fall in the blood pressure, and by the steeply rising and falling second peak.

The Xuan mai is caused by vascular hardening and is symptomatic of an illness including liver and kidney ailments. This waveform is associated with tensions in the autonomic nerve system to cause the walls of the blood vessels to stiffen, and the blood pulsations cannot be properly reflected in the pulse waveform. A typical example is shown in FIG. 31C which is taken from a 34-year-old male patient. The Xuan mai type waveform is characterized by a rapid rise followed by a gradual drop in the blood pressure over a period of time.

Figure 32:
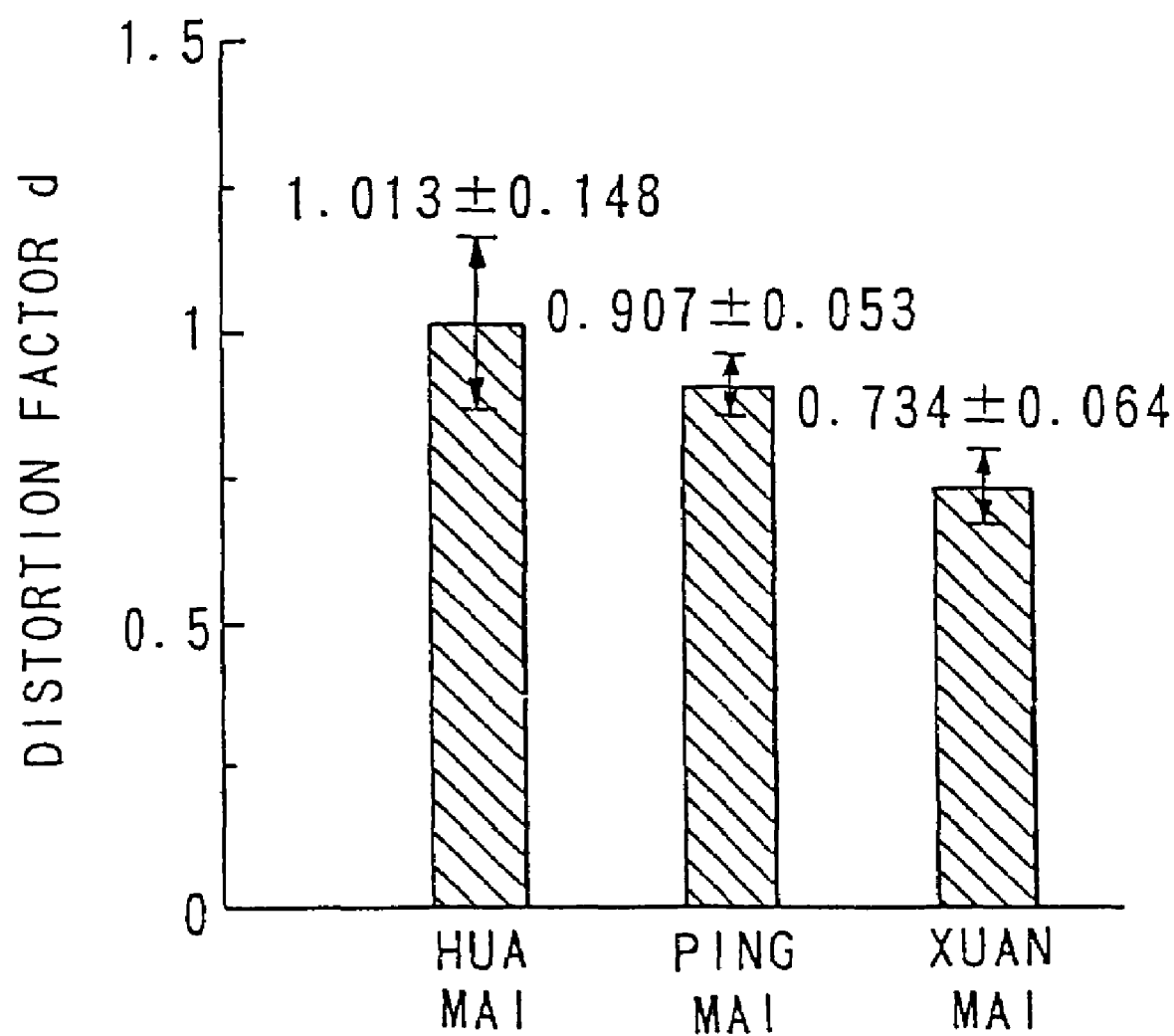
FIG. 32 is a bar graph to show the relationship between the distortion factor d and the three types of pulse waveform.

FIG. 32 is a bar graph showing the variations of the distortion factor d in Hua mai, Ping mai and Xuan mai waveform shapes, and shows the analytic results of many examinations (21 cases of Hua mai, 35 cases of Ping mai, 22 cases of Xuan mai).

It is shown that in the Ping mai type the pulsing pressure is centered around a distortion factor d at 0.907 with a deviation of ±0.05; in the Hua mai type, the distortion factor d is larger than the one of the Ping mai type at 1.013 with a deviation of ±0.148; in the Xuan mai type, the distortion factor d is the smallest of the three types, and is centered around 0.734 with a deviation of ±0.064.

The statistical significance of the distortion factors of the waveform types was analyzed by t-test, and it was found that the differences in the waveform shapes were statistically significant with uncertainty of less than 0.05.

Chapter 3-0-2: Relationship Between Waveform Distortion and Circulatory Parameters Second, the relationship between the waveform distortion and the circulatory dynamic parameters described in Chapter 2-1-1 will be explained.

Figure 33:
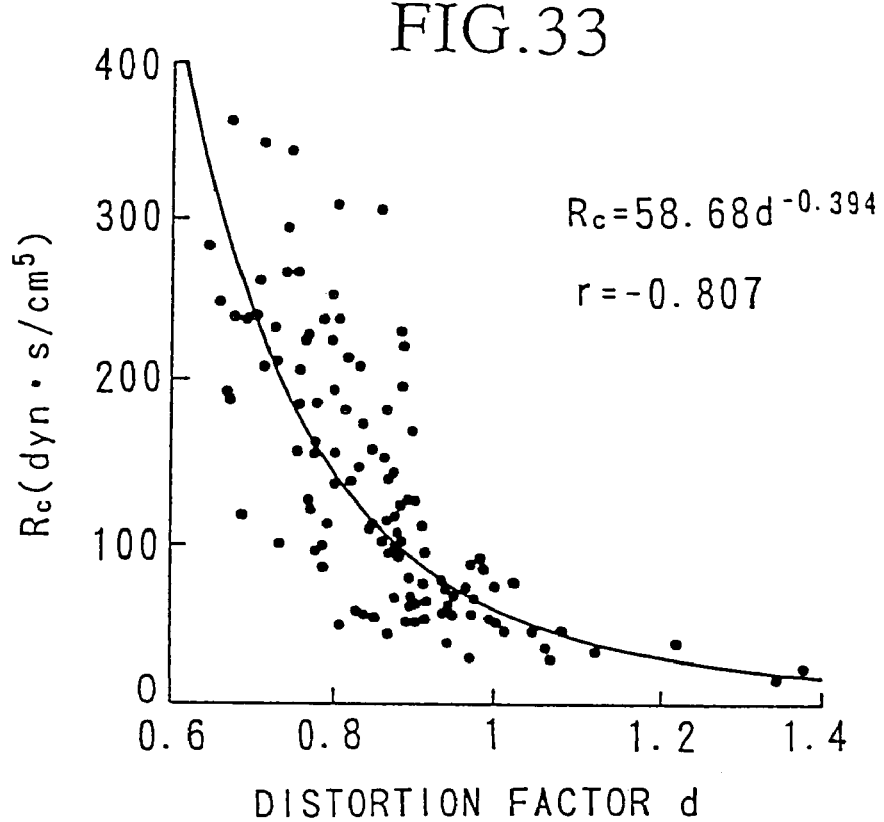
FIG. 33 is a graph to show the relationship between the distortion factor d and the proximal section resistance $R_c$.

The relationships of the distortion factor d to the circulatory dynamic parameters are shown in FIGS. 33 to 36. These data were taken from a experiment of 120 cases. FIG. 33 shows the relationship of the distortion factor d to the proximal vascular resistance $R_c$, which is expressed mathematically as:

$$R_c = 58.68 \cdot d^{-0.394}$$

where the correlation coefficient $r=-0.807$

Figure 34:
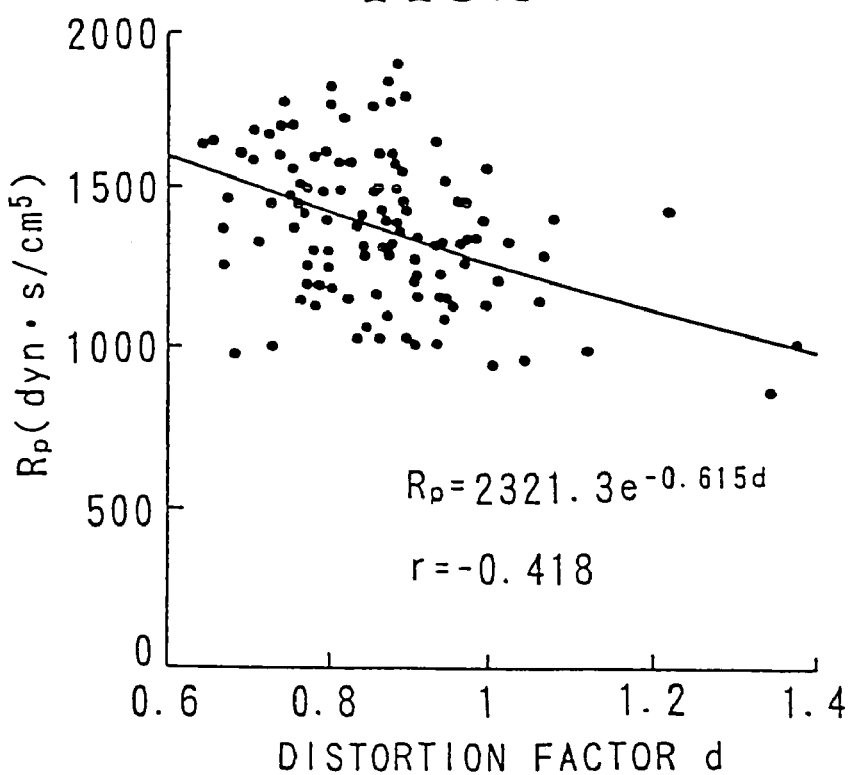
FIG. 34 is a graph to show the relationship between the distortion factor d and the distal section blood flow resistance $R_p$.

FIG. 34 shows the relationship between the distortion factor d and the distal vascular resistance $R_p$ which is expressed as:

$$R_p = 2321 \cdot e^{-0.615d}$$

where the correlation coefficient $r=-0.418$

Figure 35:
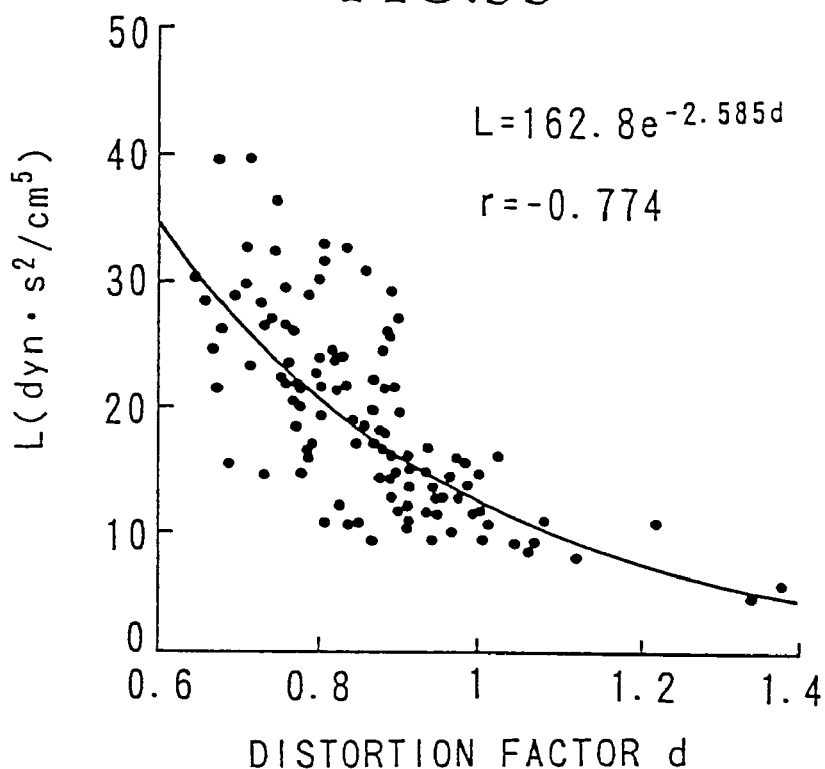
FIG. 35 is a graph to show the relationship between the distortion factor d and the blood flow momentum L.

FIG. 35 shows the relationship between the distortion factor d and the momentum L, which is expressed as:

$$L = 162.8 \cdot e^{-2585d}$$

where the correlation coefficient $r=-0.774$

Figure 36:
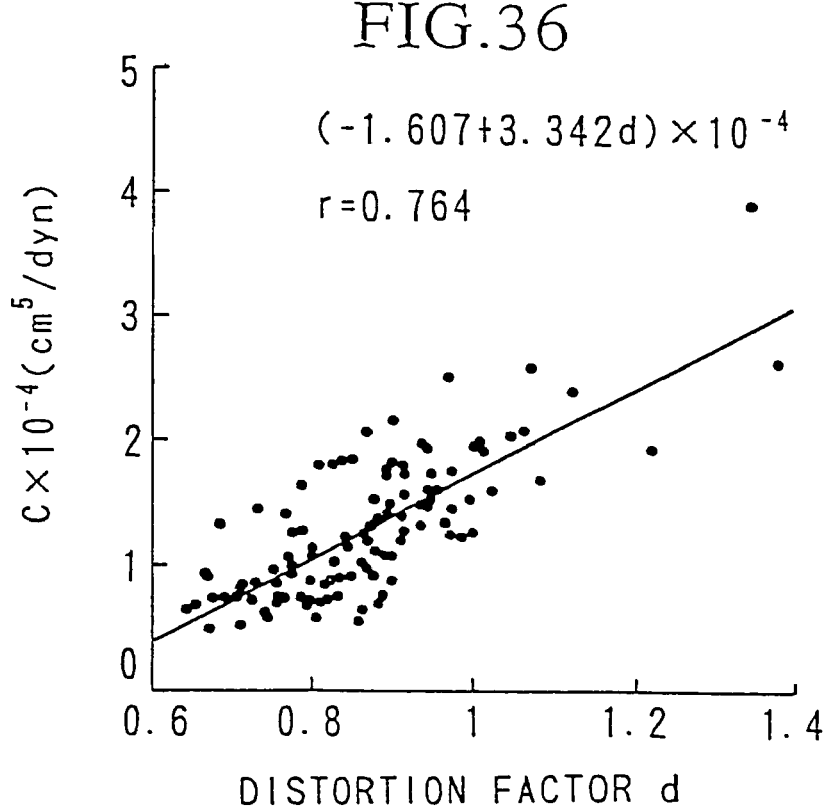
FIG. 36 is a graph to show the relationship between the distortion factor d and the vascular compliance C.

FIG. 36 shows the relationship of the distortion factor d to the compliance C, which is expressed as:

$$C = 10^{-4}(-1.607 + 3.342 \cdot d)$$

where the correlation coefficient $r=0.764$.

Chapter 3-0-3: Relationship Between Circulatory Parameters and Waveform Shape

Just for, the relationship between the circulatory parameters and waveform shape will be explained.

Figure 37:
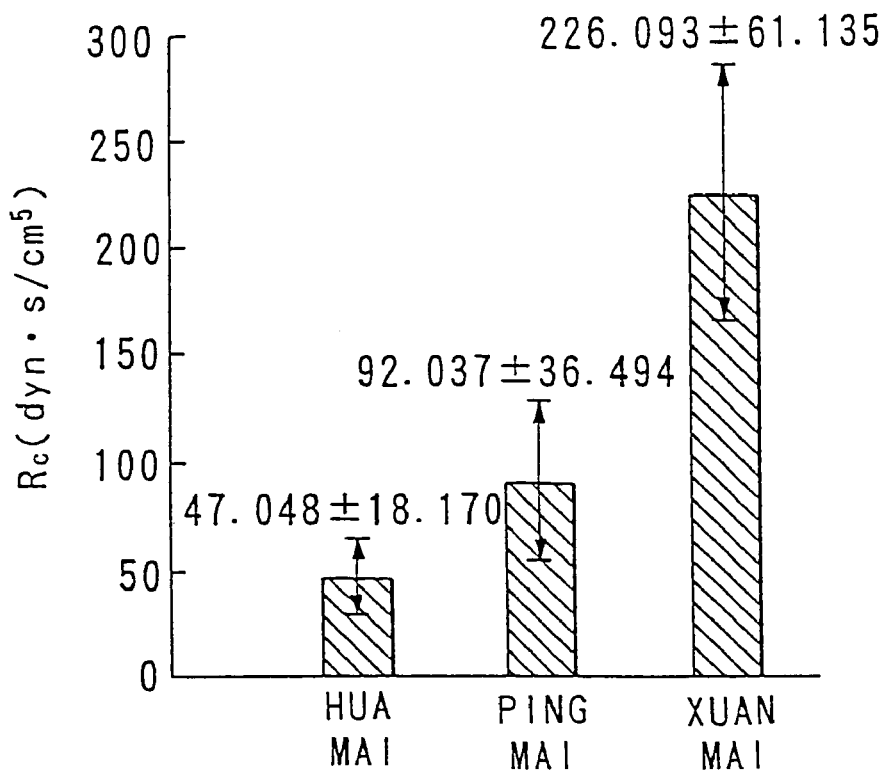
FIG. 37 is a bar graph to show the relationship between the proximal section blood flow resistance $R_c$ and the three types of waveforms.

FIGS. 37 to 40 are bar graphs showing the four circulatory dynamic parameters for the three waveform types: Hua mai, Ping mai and Xuan mai. FIG. 37 shows the proximal resistance $R_c$ for the three waveform types. The resistance is the smallest in the Hua mai type at $47.048 \pm 18.170$ (dyn·s/cm$^5$). The next smallest is the resistance in the Ping Mai type at $92.037 \pm 36.494$ (dyn·s/cm$^5$). The largest resistance is exhibited in the Xuan mai type at $226.093 \pm 61.135$ (dyn·s/cm$^5$).

Figure 38:
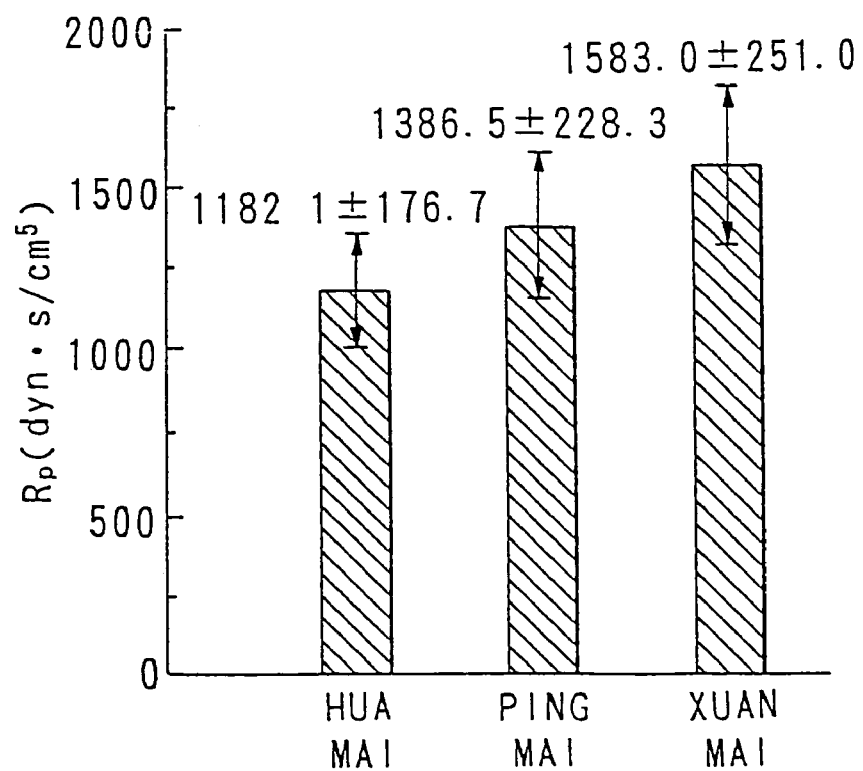
FIG. 38 is a bar graph to show the relationship between the distal section blood flow resistance $R_p$ and the three types of waveforms.

FIG. 38 shows the distal section resistance $R_p$ for the three waveform types. In this case, the Hua mai type exhibits the smallest resistance at $1182.1 \pm 176.7$ (dyn·s/cm$^5$); followed by the Ping mai type at $1386.5 \pm 228.3$ (dyn·s/cm$^5$); and the Xuan type mai type exhibits the largest resistance at $1583.0 \pm 251.0$ (dyn·s/cm$^5$).

Figure 39:
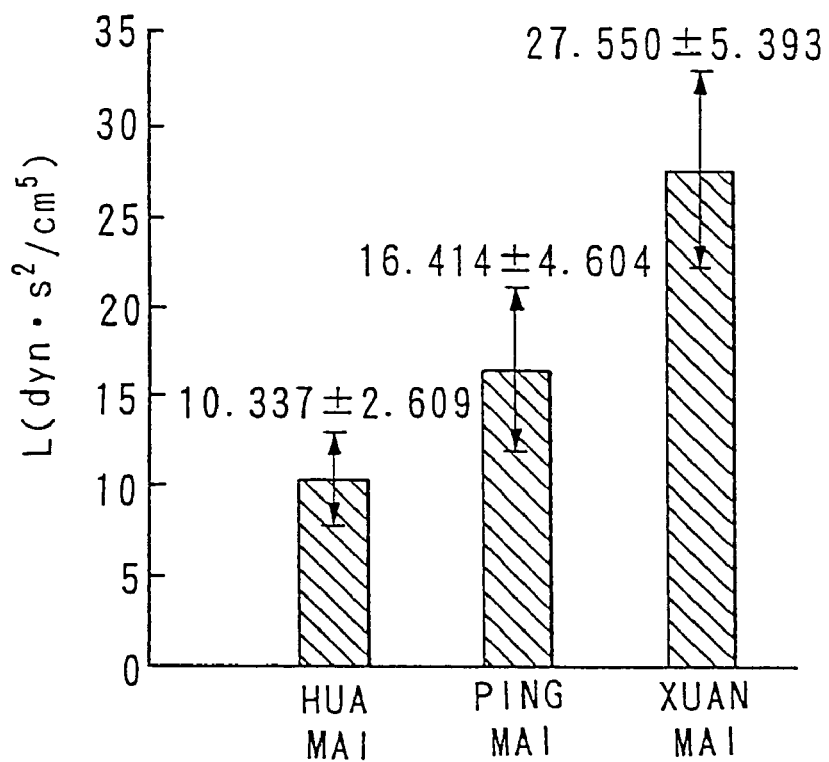
FIG. 39 is a bar graph to show the relationship between the blood flow momentum L and the three types of waveforms.

FIG. 39 shows the momentum L of the blood flow for the three waveform types. The momentum is the smallest in the Hua mai type at $10.337 \pm 2.609$ (dyn·s$^2$/cm$^5$); followed by that in the Ping may type at $16.414 \pm 4.604$ (dyn·s$^2$/cm$^5$); and the largest L is in the Xuan mai type at $27.550 \pm 5.393$ (dyn·s$^2$/cm$^5$).

Figure 40:
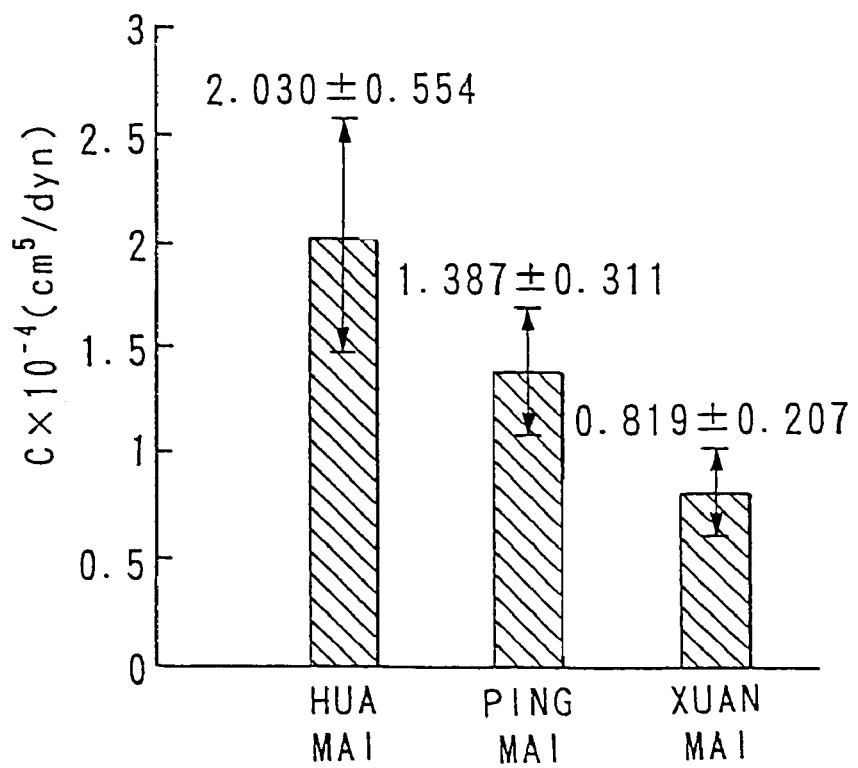
FIG. 40 is a bar graph to show the relationship between the compliance C and the three types of waveforms.

FIG. 40 shows the compliance C for the three waveform types. The largest compliance is exhibited by the Ping mai type at $(2.030 \pm 0.554) \cdot 10^{-4}$ (cm$^5$/dyn); followed by the Ping mai type at $(1.387\pm0.311)\cdot10^{-4}$ (cm$^5$/dyn); and the Xuan mai type has the smallest compliance at $(0.894\pm0.207)\cdot10^{-4}$ (cm$^5$/dyn). The compliance C values for the three types of waveforms seem to be opposite to the other parameters, but the order of the parameters becomes the same for all the waveform shapes, when inverse values, 1/C, of the compliance values are used. The relationship between the dynamic parameters and the three waveform types were subjected to the T-test, and the results were statistically significant with uncertainty of less than 0.05.

Chapter 3-1: Diagnostic Apparatus on the Basis of the Waveform Shapes

Next, the diagnostic apparatus (i) of the third embodiment will be explained. This apparatus computes the distortion from the measurement data of the pulse waveforms, decides the shape on the basis of the distortion and performs diagnosis on the basis of the waveform shapes.

FIG. 27 is a block diagram showing the structure of this apparatus (i). The reference numeral 311 refers to a pulse wave detection device, and FIG. 28 illustrates the method of detection. In FIG. 28, S1 refers to a pressure sensor for detecting the radial arterial waveforms of an examinee. The numeral S2 refers to a cuff belt worn on the upper arm to measure the blood pressure. The pulse wave detection device 311 modifies the radial arterial waveforms with blood pressure, and outputs the results as analogue electrical signals. In FIG. 27, the numeral 313 refers to an A/D converter to covert the analogue signals outputted by the pulse wave detection device 311 to digital signals. The numeral 314 refers to a distortion calculator comprising a Fourier analyzer 315 and a distortion computation device 317. The Fourier analyzer 315 includes microcomputers and others, and the analytical programs for Fourier analysis are stored in memories such as ROM. The Fourier analyzer 315 analyzes the digital signals outputted from the A/D converter 313, and outputs the amplitude $Q_1$ of the fundamental waveform, the amplitude $Q_2$ of the second harmonics, . . . and the amplitude $Q_n$ of the nth harmonics. The value of n is determined suitably depending on the amplitude of the nth harmonic distortion.

The distortion calculator 317 calculates the value of the distortion based on the outputted amplitudes $Q_1$, $Q_2$ and $Q_n$. The distortion value d is obtain from the expression:

$$d = \frac{\sqrt{Q_2^2 + Q_3^2 + \ldots + Q_n^2}}{Q_1}$$

The numeral 319 refers to a waveform shape analyzer which determines the shape of the waveforms based on the distortion factor d outputted from the distortion calculator 314 such that:

1.161>d>0.960 defines the Hua mai type;
0.960>d>0.854 defines the Ping mai type; and
0.798>d>0.670 defines the Xuan mai type.

The waveform shape analyzer 319 either outputs the results of the determination of the waveform type according to the above definitions, or displays or prints on an output device 321 that a waveform type is indeterminate.

In this case, the diagnostic apparatus presented in Chapter 1 may be used for diagnostics by storing data (potential illness) relating the waveform shapes to the conditions of the living body in the knowledge data base 26, and reading out data (i.e. diagnosis) to correspond with the results obtained from the waveform shape analyzer 319 of the third embodiment.

Chapter 3-2: Diagnostic Apparatus on the Basis of the Circulatory Parameters

Next, the diagnostic apparatus (ii) of the third embodiment will be explained. This apparatus computes the distortion from the measurement data of the pulse waves; computes the circulatory parameters by the distortion; and performs diagnosis on the basis of these parameters.

Figure 29:
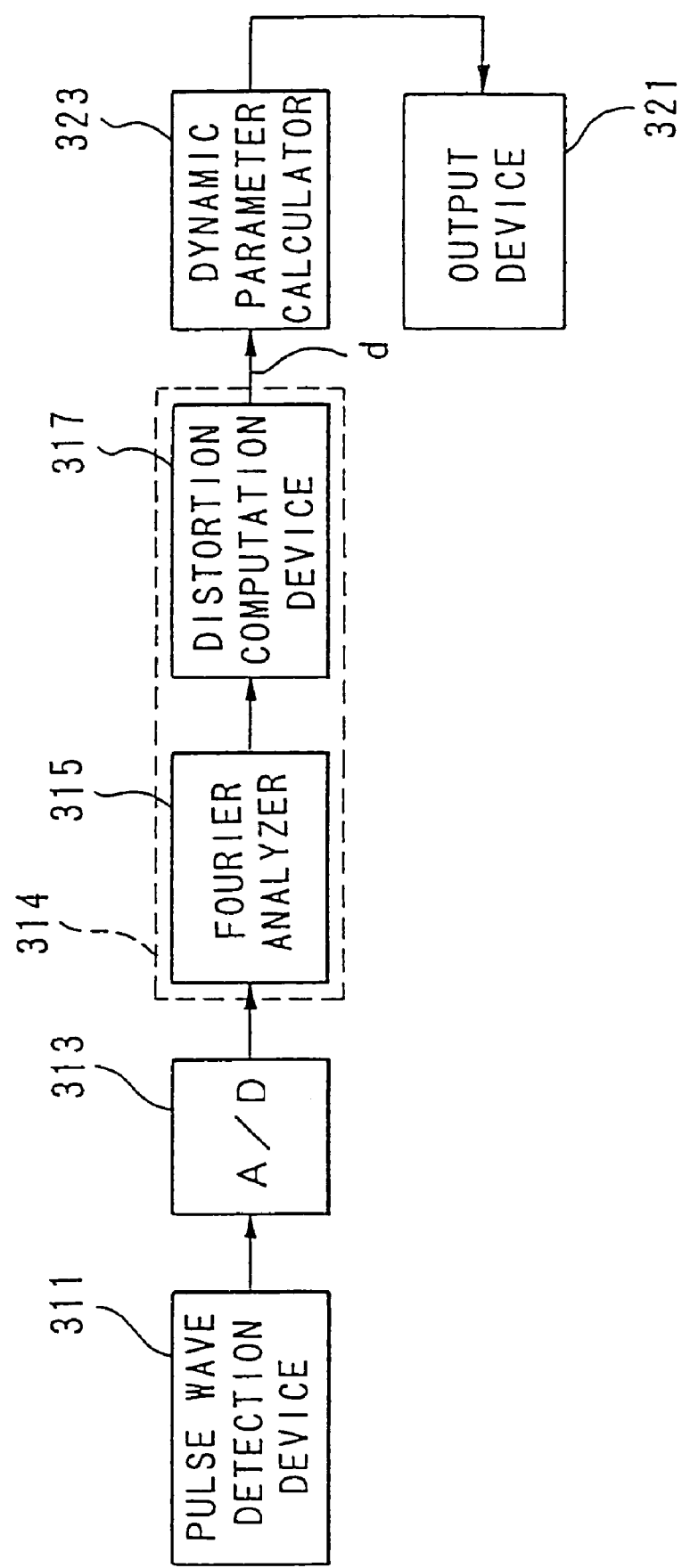
FIG. 29 is a schematic block diagram to show the configuration of another diagnostic apparatus.

The apparatus (ii) is shown in FIG. 29. In FIG. 29, those components which are the same as in the apparatus (i) shown in FIG. 27 are given the same reference numerals, and their explanations are omitted.

The numeral 323 refers to a circulatory dynamic parameter calculator, and computes the values of the proximal section resistance $R_c$, distal section resistance $R_p$, the momentum L and the compliance C on the basis of the values of the distortion factor d calculated by the distortion calculator 314. The circulatory dynamic parameters are calculated from the following expressions.

$$R_c = 58.68 \cdot d^{-0.394}$$

$$R_p = 2321 \cdot e^{-0.615d}$$

$$L = 162.8 \cdot e^{-2585d}$$

$$C = 10^{-4}(-1.607 + 3.342 \cdot d)$$

The units are the same as in the previous expressions in Chapter 2-1-1.

As explained above, by utilizing the relationship equations, it will be possible to compute the circulatory dynamic parameters without using the pulse wave analysis apparatus described in Chapter 2. It is obvious that the computed dynamic parameters are also applicable to the first embodiment described in Chapter 1.

The dynamic parameter calculator 323 determines the waveform type based on the dynamic parameters.

In this apparatus (ii), the Hua mai type is defined by:
$28.878 < R_c < 65.218$
$1005.4 < R_p < 1358.5$
$7.647 < L < 12.994$ and
$1.476 \times 10^{-4} < C < 2.584 \times 10^{-4}$,
the Ping mai type is defined by:
$55.543 < R_c < 128.531$
$1158.2 < R_p < 1614.8$
$11.810 < L < 21.018$ and
$1.076 \times 10^{-4} < C < 1.698 \times 10^{-4}$,
the Xuan mai type is defined by:
$164.958 < R_c < 287.228$
$1332.0 < R_p < 1834.0$
$22.157 < L < 32.943$ and
$0.612 \times 10^{-4} < C < 1.026 \times 10^{-4}$.

The dynamic parameter calculator 323 outputs the results of the determination through an output device 321.

It is obvious that the defined waveform types as parameters are also applicable to the first embodiment.

Chapter 3-3: Diagnostic Apparatus on the Basis of Waveform Shapes and Parameters Next, the apparatus (iii) of the third embodiment will be explained. This apparatus computes the distortion from the measurement data of the pulse waves; by the distortion, computes the circulatory parameters and determines the waveform shape type; and performs diagnosis on the basis of these parameters and the shapes.

Figure 30:
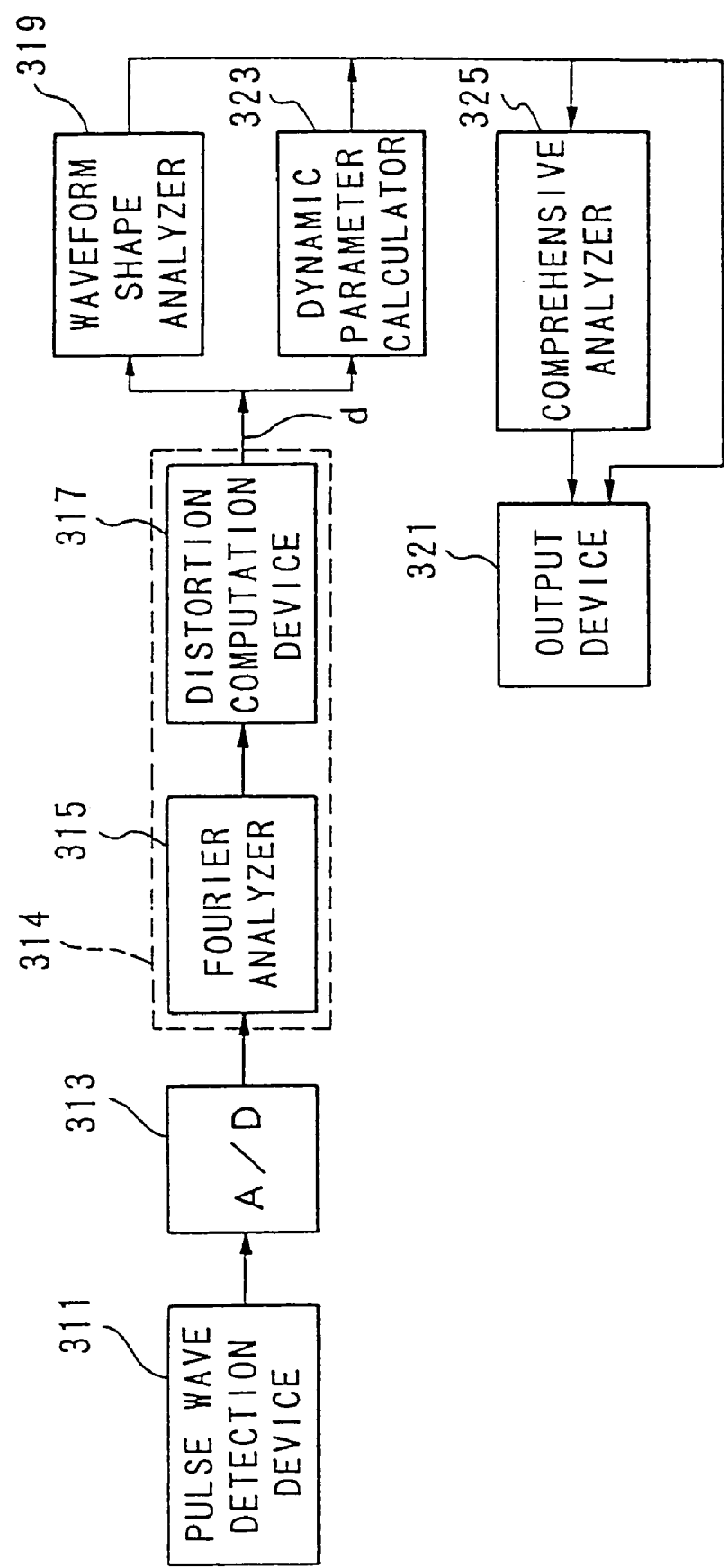
FIG. 30 is a schematic block diagram to show the configuration of the other diagnostic apparatus.

This apparatus (iii) is shown in FIG. 30. In FIG. 30, those components which are the same as in the apparatus (i) or (ii)

shown in FIGS. 27 or 29 are referred to by the same reference numerals, and their explanations are omitted.

The reference numeral 325 refers to a comprehensive analyzer, and performs pulse wave analysis based on the entire results of the waveform shape analyzer 319 and the dynamic parameter calculator 323. For example, the waveform results by the waveform analyzer 319 and the parameters determined by the dynamic parameter calculator 323 may be stored in a memory table in the comprehensive analyzer 325 for its use. The output results may be one of the three waveform shape types, or the names of the illness associated with that waveform. The output device 321 displays or prints the results outputted from the waveform shape analyzer 319, from the dynamic parameter calculator 323, from the comprehensive analyzer 325 and others. The user of the apparatus such as doctors and others are thus able to obtain the diagnostic information regarding the examinee.

Alternatively, a diagnosis may be performed in terms of the waveforms parameters in the first embodiment, determined on the basis of the waveform shape obtained from the waveform shape analyzer 319 and the circulatory dynamic parameters computed by the dynamic parameter calculator 323.

Figure 41:
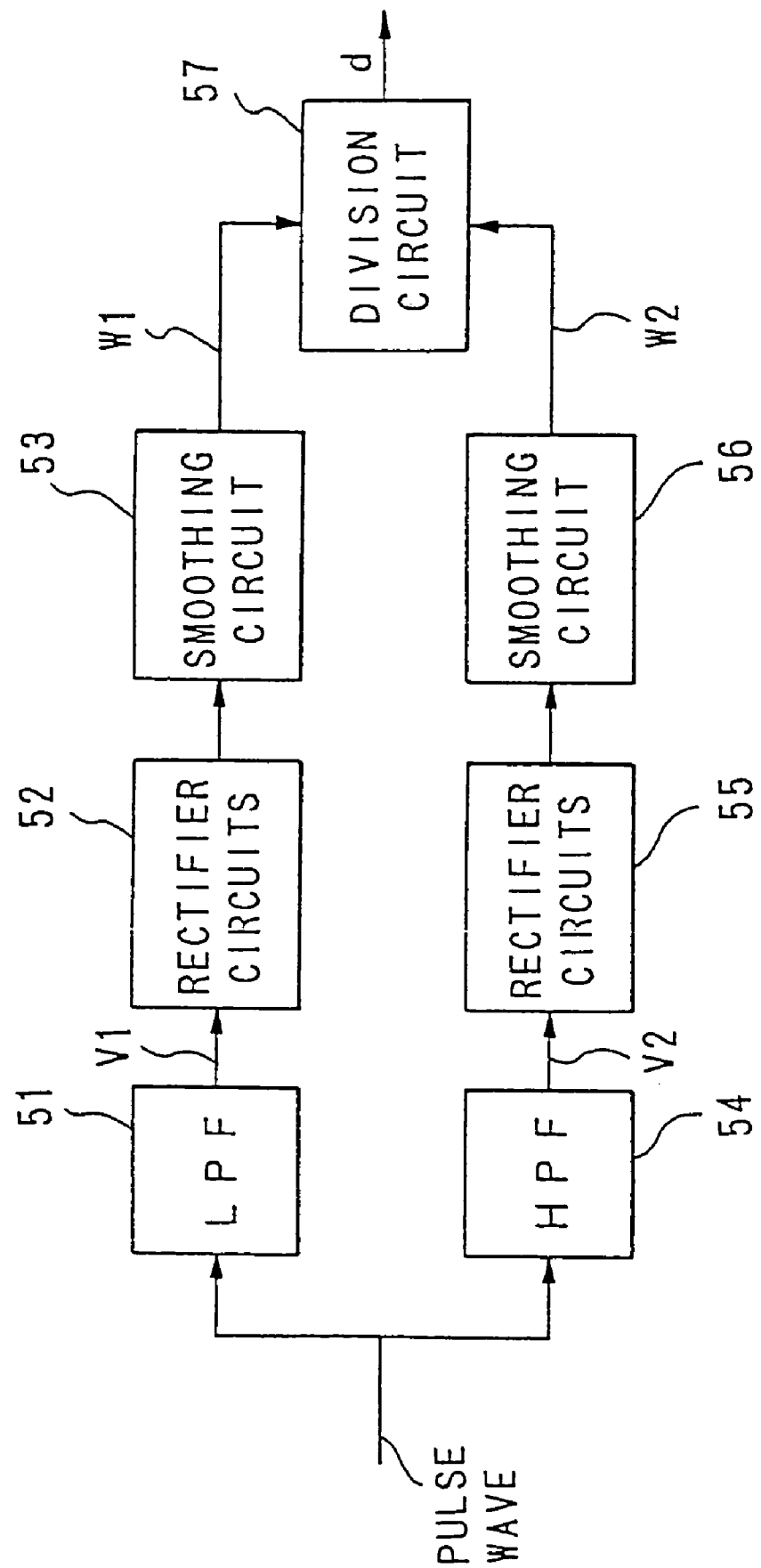
FIG. 41 is a block diagram to show another example of calculating the distortion factor d.

In the third embodiment, the distortion factor d may be defined in terms of the mathematical expression $$\frac{Q_2 + Q_3 + \ldots + Q_n}{Q_1},$$

or it may be defined in other ways, but the same relationship will be obtained. For example, the distortion factor d may be obtained by a method illustrated in FIG. 41. In this method, the pulse waves are inputted into a low-pass filter 351 and a high-pass filter 354 to output a low frequency component v1 and a high frequency component v2. The outputted-signals v1, v2 are passed through rectifier circuits 352, 355 and passed through smoothing circuits (normally used LPF) 353, 356 to obtain direct current signals w1, w2. The DC signals w1, w2 are forwarded to the division circuit 357 to obtain a value of the distortion factor d=w2/w1.

Chapter 4: Stress Level and Physiological Age Evaluation Apparatus

Recently, stress and fatigue has come to be one of the main causes of adult sickness, and so called death due to overwork. If the conditions of stress and fatigue can be grasped, then through appropriate precautionary measures taken at an early stage, the progression of the adult disease, and sudden death etc. can be prevented.

Presently there are few examination methods which can detect stress, fatigue and often physiological and psychological problem of a human body. Moreover, of these few examination methods, there are none which enable simple examination. For example, some methods measure the contents of catecholamine or cortisol included in the blood or urine, as an indication of physiological stress. However with these methods, a blood sample or a special assay method is necessary. The methods are thus not simple methods which can be made every day. Moreover, there is a method which measures the urine concentration of adrenocortical hormone metabolism production as an indication of stress. However, this method also cannot be considered simple since a urine sample is required. Moreover, the reliability as an examination method has yet to be established. The so called Claris system diagnostic questionnaire of the B&M company was an established method of measuring psychological stress. However this diagnostic questionnaire had 81 question items, thus imposing a heavy burden on the patient or the diagnostician at the time of questioning. Additionally, there has been a need for a device whereby one can easily perform of his own physiological age as well as stress level.

In view of the problems described above, the present inventors selected the peak points of the waveforms to be representative of the waveform parameters to be used in the determination of psychosomatic stress levels and physiological age, and produced a diagnostic apparatus of a fourth embodiment.

The application of the diagnosis of the present invention is not limited to the stress level or physiological age, further the parameters are not limited to disclosed waveform parameters used to the diagnosis in the embodiment of the invention. For other diagnoses, some suitable diagnostic apparatus can be developed using the same approach as presented in the following.

The peak points of the waveforms obtained by this diagnostic apparatus can be applicable to the first embodiment for the waveform parameters.

In this Chapter, the diagnostic, apparatus according to a fourth embodiment of the present invention will be explained.

Chapter 4-0: Pre-Examinations

The present inventor carried out the following pre-examinations when designing the device for stress evaluation.

Chapter 4-0-1: Characteristics for Substitutional Parameters

In order to carry out the stress evaluation without imposing a heavy burden on the examiner or the procedure, substitute parameters for stress parameters such as blood plasma catecholamine values, which reflect the stress level are necessary. The present inventor observed that waveforms of pulse waves change, due to physiological stress, physiological age and psychological stress, and selected waveforms of pulse waves as candidates for parameters for use in stress evaluation. In the process, the radial arterial pulses of 53 examinees was measured, and the following information, i.e., the peak points (inflection points) of pulse waveform was collected as characterizing waveform parameters to analyze the problem.

(a) The period $T_6$, which represents the time for one pulsation cycle from the rise of one pulsation (in the following, the time of this rise is referred to as the pulse wave initiation time) and the next pulsation rise.

(b) The blood pressure values $y_1$~$y_5$, representing a maximum point $P_1$, a minimum point $P_2$, a maximum point $P_3$, a minimum point $P_4$, and a maximum point $P_5$ appearing successively in the pulse waves.

(c) The elapsed periods $T_1$~$T_5$, corresponding to time period from the pulse wave initiation time to the appearance of the respective points $P_1$~$P_5$.

Figure 42:
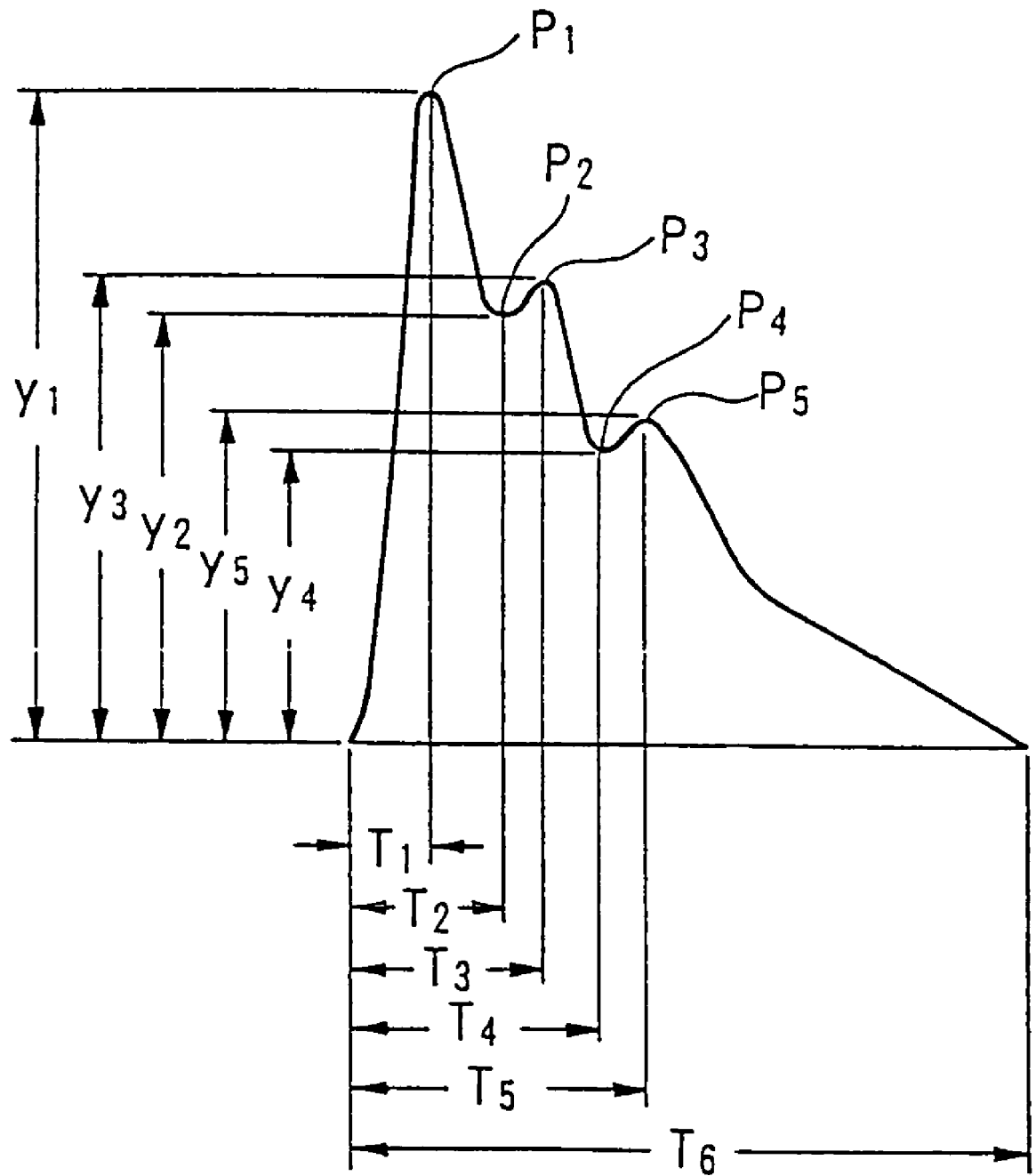
FIG. 42 is an example of pulse waves used in stress level evaluation according to an fourth embodiment of the present invention.

Refer to FIG. 42 for the above.

Moreover, the present inventor observed that conscious symptoms appear when the stress level became high, and measured psychosomatic fatigue level using the psychosomatic fatigue level diagnostic questionnaire shown in FIG. 43. The questions in the diagnostic questionnaire were to ascertain whether the patients was conscious of the various symptoms which are prominent at high stress levels. The examinee selected one of; never, sometimes, often, or always as a reply to the questions. Here the points for the respective replies were:

never at "0";
sometimes at "1";
often at "2";
and always at "3".

With an affirmative reply to a question, that is to say, a higher reply level for the degree of consciousness of the symptom, proportionally higher points were obtained. The total points obtained for the patient's selected answers become the psychosomatic fatigue level M.

Chapter 4-0-2: Reference Values for Stress Levels

The blood plasma catecholamine value has been recognized in the past as a stress index of physiological stress. Therefore the blood plasma adrenaline densities AD (ng/ml), and the blood plasma nor adrenaline densities NA (ng/ml), in the blood of 53 examinees were measured, and became the reference value for the physiological stress of each of the examinees.

For the psychological stress, a diagnostic questionnaire with 81 headings (B & M Claris System) was made for each of the examinees. The results of this became the reference value MS for the psychological stress level of the examinee.

Chapter 4-0-3: Correlation Analysis

A correlation analysis was made among the respective parameters obtained for each examinee in the above Chapter 4-0-1, and in the physiological stress level and psychological stress level obtained in the above Chapter 4-0-2.

(1) Physiological Stress

Initially, in making a correlation analysis of the blood plasma catecholamine value, and the waveform parameters, the following equation was obtained as a relationship equation with a high correlation coefficient "r", $$NA(ng/ml) = -0.44(T_5 - T_1) + 1.07 \quad (51)$$

with main correlation coefficient r=0.44 (probability p<0.000001, F value=25.42).

It was confirmed that with this equation as an indication of physiological stress level, the blood plasma nor adrenaline value could be estimated on the basis of the waveform parameters $T_1$ and $T_5$. In the present embodiment, the physiological stress level is calculated by calculating out the right side in equation (51).

In making a correlation analysis including not only the waveform parameters but also the psychosomatic fatigue level M, the following relationship equation was obtained, $$NA(ng/ml) = 0.46M + 0.24\frac{y_1}{T_1} \quad (52)$$

with r=0.51, (p<0.000001, F=12.47).

Also including the psychosomatic fatigue level M as a parameter in this way was confirmed to give a more accurate value for the estimation of the physiological stress level. In the present example, when it is possible to obtain the psychosomatic fatigue level M, the physiological stress level is calculated by calculating the right side in equation (52).

(2) Psychological Stress

In making a correlation analysis of the reference value MS for the psychological stress, the waveform parameters and the psychosomatic fatigue level M, the following equation was obtained as a relationship equation with a high correlation coefficient.

$$MS = 0.45M + \frac{0.29(T_4 - T_1)}{T_6} - 14.83 \quad (53)$$

with r=0.56, (p<0.000001, F=21.61).

In the present embodiment, the psychological stress level is calculated by carrying out the right side calculation in equation (53).

(3) Physiological Age

When the correlation relationship between the age Y of the examinee, and the waveform parameters was investigated, it was found that a correlation coefficient existed between both.

$$Y = -33.74(T_5 - T_4) + 61.64\frac{T_1}{T_6} - 8.0678\frac{(T_5 - T_4)}{T_6} + 33.324 \quad (54)$$

with r=0.56, (p<0.00000, F=12.609).

Chapter 4-1: Diagnostic Apparatus (i)

Next, the diagnostic apparatus (i) in accordance with the fourth embodiment of the present invention will be explained.

This apparatus performs diagnosis of physiological and psychological stress levels; and physiological age of the examinee on the base of the inputted parameters of his pulse waveforms.

Chapter 4-1-1: Structure of the Diagnostic Apparatus (i)

Figure 44:
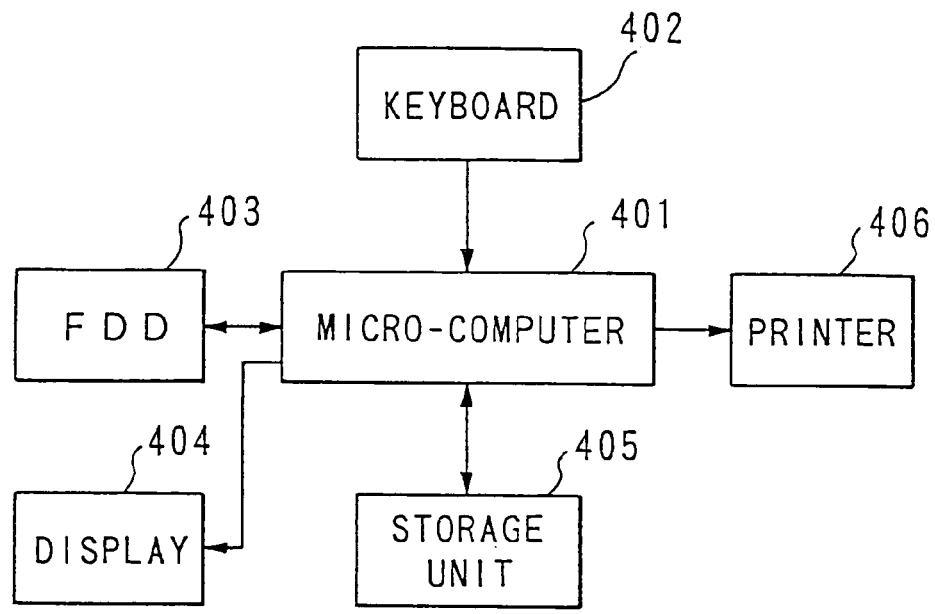
FIG. 44 is a block diagram showing a construction of a first variation of a stress level evaluation apparatus in accordance with the fourth embodiment of the invention.

FIG. 44 shows the structure of the apparatus according to the apparatus (i). In this Figure, numeral 401 indicates a micro-computer, for controlling the operation of the respective components of the apparatus, and for carrying out a diagnosis of the physiological stress level, psychological stress level and physiological age according to the above equations (52), (53) and (54). Numeral 402 indicates a keyboard which is used as an input means for command of the micro-computer 401, and for the input of parameters for diagnosis. Numeral 403 indicates a FDD (floppy disk drive unit) provided as a parameter input means in the case of a large number of examinees. The examiner installs a FD, on which is stored the parameters for the various examinees, into the FDD 403. Consequently, the parameters for all examinees can be transferred to the micro-computer 401 as a batch. The means for storage of the parameters to be inputted to the apparatus is not limited to a magnetic disk such as a floppy disk, and disks such as optical magnetic disks may be used. Numeral 404 indicates a display apparatus such as a CRT, which displays the messages and stress level diagnosis results output from the micro-computer 401, for viewing by the examiner. Numeral 405 indicates a large capacity storage unit provided for storing the diagnosis results of the stress levels etc., and the parameters for use in the diagnosis, serially for each examinee. Numeral 406 indicates a printer for the output of diagnosis results such as stress level.

Chapter 4-1-2: Operation of the Diagnostic Apparatus (i)

On switching on the power supply to the diagnostic apparatus (i), an initialization process is carried out by the micro-computer 401, and a menu screen for prompting the selection of either the keyboard 402 or the FDD 403 for carrying out the parameter input, appears on the display device 404. The examiner inputs a command from the keyboard, and selects the desired input configuration.

(1) Parameter Input

When the keyboard input configuration is selected, the examiner inputs successively by way of keyboard 402, the identification information for the examinee, the parameters necessary for evaluation, that is to say the waveform parameters and psychosomatic fatigue level obtained by the above fatigue level diagnostic questionnaire, and the year, month and day of collection of these parameters. This information is successively inputted to the buffer memory inside the micro-computer 401.

On the other hand, when the FDD input configuration is selected, the examiner inserts into the FDD 403, the floppy disk on which is stored the identifying information for each examinee, the parameters necessary for evaluation of stress level etc., and the year, month and day of collection of these parameters, and inputs a command from the keyboard 402 directing input from the floppy disk to the buffer memory. As a result, the information corresponding to each of the examinees on the FD is input sequentially from the FDD 403 to the buffer memory inside the micro-computer 401.

(2) Diagnosis of Stress Level (and the Like)

On completion of input of the above mentioned parameters, the parameters in the buffer memory for diagnosis of the stress of each examinee, are substituted into the above mentioned equations (52), (53) and (54) to obtain the physiological stress level, psychological stress level and physiological age for each of the examinees. The resultant physiological and psychological stress levels and physiological age for each of the examinees are stored temporarily in the buffer memory. Furthermore, the stress level for each of the examinees and the parameters used for calculation of the stress levels are displayed for each examinee on the display device 404.

(3) Storage of Diagnosis Results

On completion of the diagnosis, the examiner directs storage of the diagnosis results from the keyboard 402, so that the information in the buffer memory corresponding to each of the examinee, is successively written to the large capacity storage unit 405. Then, more specifically, with the present apparatus, the diagnosis results such as stress level, and the information used in the diagnosis are partitioned for each examinee, and stored. The information related to the respective examinees that is read from the buffer memory, is added to the end of the previously stored information corresponding to the respective examinees in the large capacity storage unit 405.

(4) Print Out of Diagnosis Results

When the examiners inputs from the key board 402, the command for output of the diagnosis results, the micro-computer 401 sends the identification information and stress levels for each of the examinees which are stored in the buffer memory, to the printer 406 for print out. Furthermore, if the examiner inputs identification information for a specific examinee, together with a command for a time series display of the stress levels, the micro-computer 401 reads from the large capacity storage unit 405, the stress levels obtained by a predetermined number of previous diagnosis corresponding to the selected examinee, and the collection year month and day of the parameters used in the stress diagnosis. The micro-computer 401 then generates data for printing a graph showing the time change of stress level, and sends this to the printer 406. As a result, the printer 406 prints out the stress level time changes for the selected examinee.

Chapter 4-2: Diagnostic Apparatus (ii)

Next, the diagnostic apparatus (ii) in accordance with the fourth embodiment.

This apparatus (ii), adds to the apparatus (i) described in Chapter 4-1, a means for measuring the pulse wave of the examinee, and a means for detecting the waveform parameters from these pulse waves, thereby enabling the collection of parameters from the examinee, and stress evaluation to be carried out simultaneously.

Chapter 4-2-1: Structure of the Diagnostic Apparatus (ii)

Figure 45:
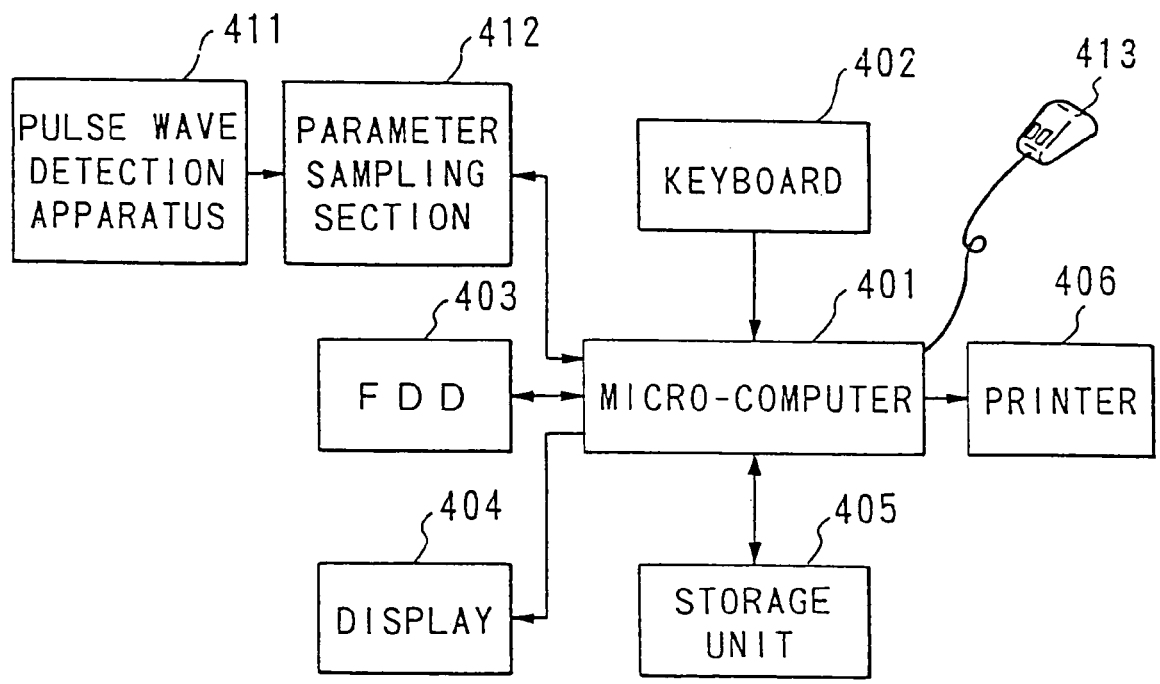
FIG. 45 is a block diagram showing a construction of a second variation of a stress level evaluation apparatus.

FIG. 45 is a block diagram showing the structure of a diagnostic apparatus. In this figure, components corresponding to those of the apparatus (ii explained in Chapter 4-1 are indicated by the same symbols and description is omitted.

In FIG. 45, numeral 411 indicates a pulse wave detection apparatus, which detects the radial pulse waveform by means of a pressure sensor attached to the examinee's wrist (not shown on the figure), and outputs a pulse wave signal (analog signal). Numeral 412 indicates a parameter sampling section, which processes signals under micro-computer 401 control, to extract waveform parameters necessary for diagnosis of the stress level, from the pulse wave signal output from the pulse wave detection apparatus 411. Numeral 413 indicates a mouse, which is connected to the micro-computer 401, and acts as a designation device when manually designating the waveform parameter, without using the parameter sampling section 412.

Figure 46:
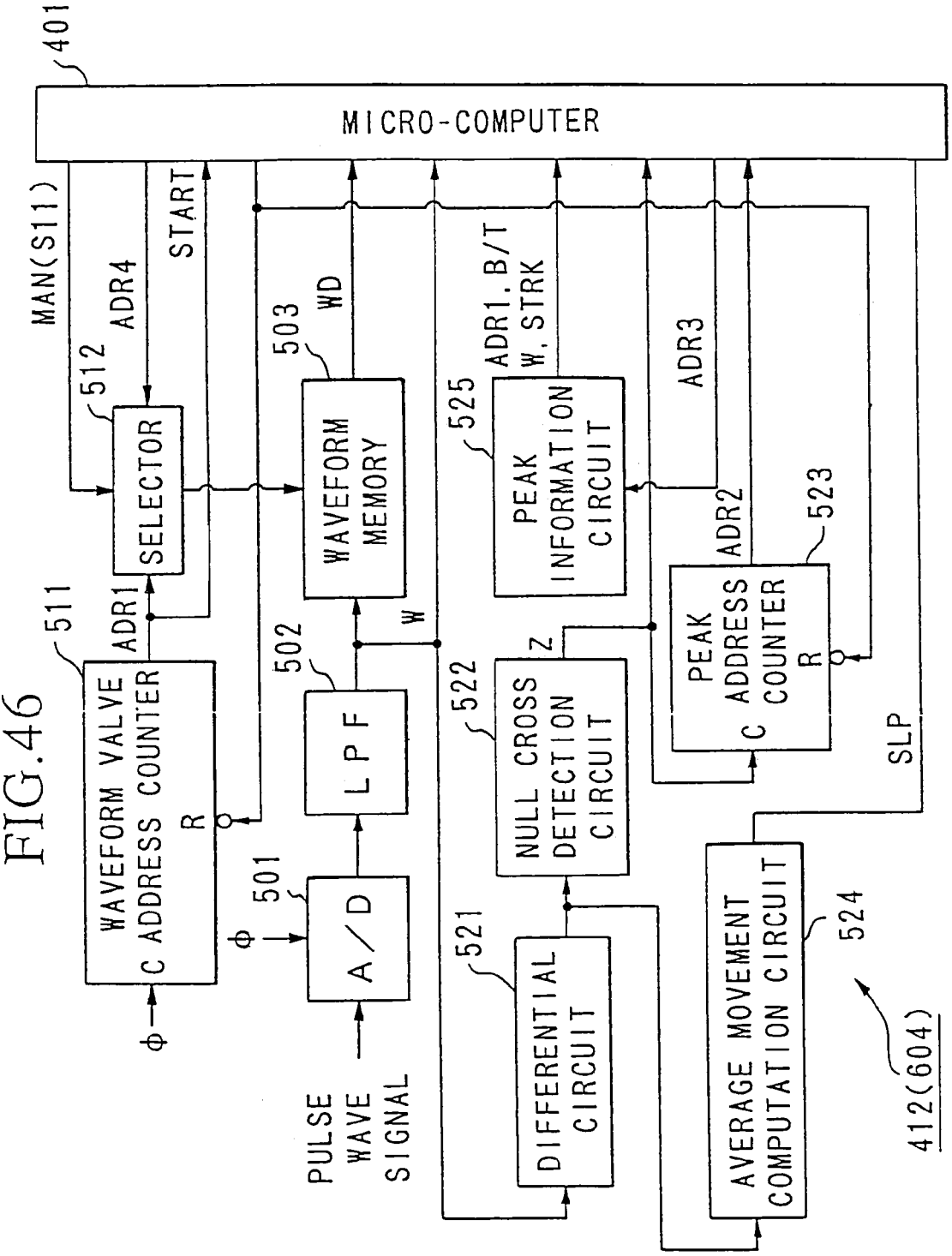
FIG. 46 is a block diagram showing a structural example of the parameter sampling unit (or the waveform sampling memory) of the second variation.

The following is a description of the construction of the parameter sampling section 412, with reference to FIG. 46. In FIG. 46, numeral 501 indicates an A/D (analog/digital) converter which converts the pulse wave signal output by the pulse wave detector 411, into a digital signal, in accordance with a sampling clock f of a fixed period, and outputs this. Numeral 502 indicates a low pass filter which carries out processing to eliminate components of the successively output digital signal from the A/D converter 501, that are above a predetermined cut-off frequency. The result is successively outputted as waveform values W. Numeral 503 indicates a waveform memory comprising a RAM (random access memory) which successively stores the waveform values W supplied by way of the low pass filter 502. Numeral 511 indicates a waveform address counter which counts the sampling clock f during the period when the waveform collection directive START from the micro-computer 401 is outputted. The count results are output as waveform addresses ADR1 into which the waveform values W are to be written. Numeral 512 indicates a selector which selects the waveform addresses ADR1 output by the waveform address counter 511, when the manual output mode signal MAN is not outputted, and supplies these to the address input terminal of the waveform memory 503; and selects the read addresses ADR4 outputted by the microcomputer 401, when the manual output mode signal MAN is outputted, and supplies these to the address input terminal of the waveform memory 503.

Numeral 521 indicates a differentiating circuit which computes the time differentials of the waveform values W which are successively output from the low pass filter 502, and outputs these. Numeral 522 indicates a null cross detection circuit which outputs a null cross detection pulse Z when the time differential of the waveform value W is "0" due to the waveform value W being a maximum value or a minimum value. Numeral 523 indicates a peak address counter which counts the null cross detection pulse Z during the period when the waveform collection directive. START from the micro-computer 401 is outputted. The count results are outputted as peak addresses ADR2. Numeral 524 indicates an average movement computation circuit which computes, up to the present time point, the mean value of the time differential values of a predetermined number of previous waveform values W, which are outputted from the differentiating circuit 521, and outputs the result as slope information SLP which shows the slope of the pulse waves up until the present time point. Numeral 525 indicates a peak information memory (to be discussed later) for storing peak information.

The micro-computer 401 carries out the following control steps based on the information inputted from the respective elements described above.

(1) Peak Information Editing

The differentiation circuit 521, and the null cross detection circuit 522 inside the parameter sampling section 412, obtain the following listed information for each detection of a waveform peak point. This information is written to the peak information memory 525 as peak information.

Contents of the Peak Information (1)-1: Waveform Value Address ADR1:

This is the write address ADR1 which is output from the waveform address counter 511 at the time point when the waveform value W outputted from the low pass filter 502, becomes a maximum or minimum value. That is to say, the write address in the waveform memory 503 for the waveform value W corresponding to the maximum or minimum value.

(1)-2: Peak Classification B/T:

This is information which indicates whether a waveform value W written to a waveform value address ADR1 is a maximum value T (Top), or a minimum value B (Bottom).

(1)-3: Waveform Value W:

This is the waveform value corresponding to the maximum value or the minimum value.

(1)-4: Stroke STRK:

This is the change portion of the waveform value, from the immediately preceding peak value to the present peak value.

(1)-5: Slope Information SLP:

This is the mean value of the time differential of the predetermined number of previous waveform values up until the present peak value.

On the stress level diagnosis, the microcomputer 401 shifts to the following operational mode.

(a) Automatic Diagnosis Mode

Reads the storage contents of the peak information memory 525, generates the waveform parameters, and carries out the stress level diagnosis in a similar manner to that of the first working diagnostic apparatus (i).

(b) Manual Designation Mode

Displays the waveform stored in the waveform memory 503 on the display device 404, detects the waveform peak point designated by operator mouse operation, and carries out the computation of the waveform parameters and diagnosis of the stress level, on the basis of the results.

Chapter 4-2-2: Operation of the Diagnosis Apparatus (ii)

The following is a description of the operation of the Diagnosis apparatus.

(a) Automatic Diagnosis Mode (a)-(1) Collection of Waveform and Peak Information Initially, on input by way of keyboard 402 of a command to obtain the stress level, the micro-computer 401 outputs a waveform collection directive START, and releases the reset of the waveform address counter 511 and the peak address counter 523, in the parameter sampling section 412.

As a result, the waveform address counter 511 starts counting the sampling clock f, and the count value is supplied via the selector 512, to the waveform memory 503 as a waveform address ADR1. The radial arterial pulse waveform detected by the pulse wave detector 411 is input to the A/D converter 501, and converted sequentially into a digital signal according to the sampling clock f, and then outputted sequentially as waveform values W, via the low pass filter 502. The waveform values W outputted in this way are supplied sequentially to the waveform memory 503, and written to a memory area designated by the waveform address ADR1 at that time point. By means of the above operation, one row of waveform values W corresponding to the radial pulse waveform illustrated in FIG. 48, are stored in the waveform memory 503.

Detection of the peak information, and writing to the peak information memory 525 is carried out in parallel with the above operation as described below.

Initially the time differential of the waveform value W output from the low pass filter 502, is computed by the differentiating circuit 521. This time differential is then input to the null cross detection circuit 522 and the mean movement calculating circuit 524. The mean movement calculating circuit calculates the mean value (that is to say mean movement value) of the predetermined number of previous time differentials for each time differential value of this type of waveform value W supplied, and the calculated result is output as slope information SLP. Here, when the waveform value W is increasing or has a maximum condition after increasing, a positive value is outputted as the slope information SLP, while when decreasing or with a minimum value after decreasing, a negative value is output as the slope information SLP.

Figures 47, 48:
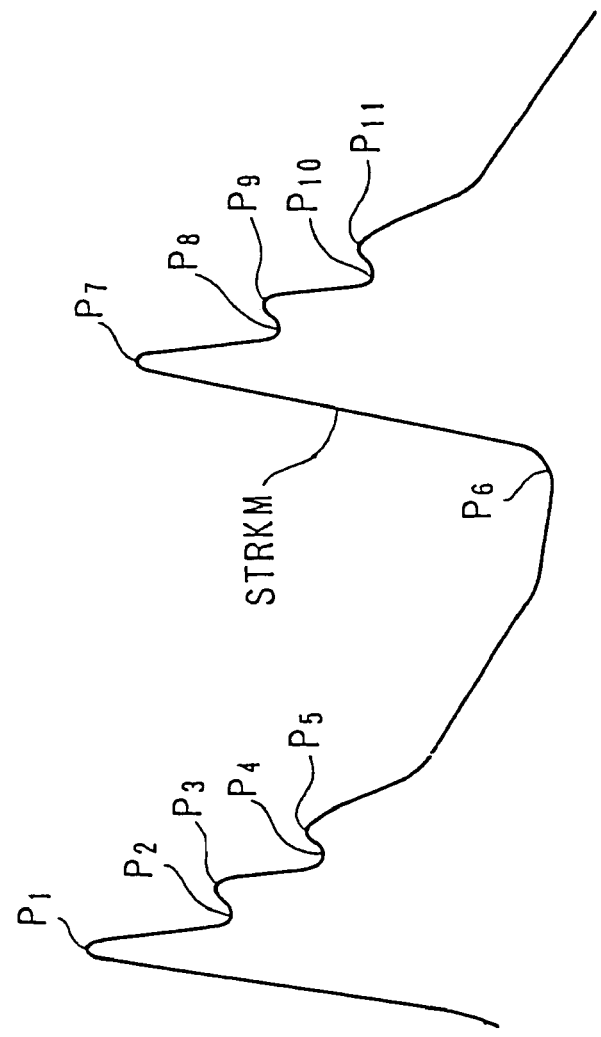
FIG. 47 is a diagram illustrating the stored contents of the peak information memory of the variation.
FIG. 48 is a diagram illustrating the radial arterial pulse waveform recorded in the waveform memory of the variation.

On output of the waveform value W corresponding to the maximum point $P_1$ as shown in FIG. 48, from the low pass filter 502, a "0" for the time differential is outputted from the differentiating circuit 521, and a null cross detection pulse Z is outputted from the null cross detection circuit 522.

As a result, the micro-computer 401 fetches, the waveform address ADR1 being 30 the count value of the waveform address counter 511, the waveform value W, the peak address ADR2 being the count value of the peak address counter (in this case ADR2="0"), and the slope information SLP, for that time point. Due to the output of the null cross detection signal Z, the count value ADR2 of the peak address counter 523 becomes "2".

Subsequently, the micro-computer 401 creates a peak classification B/T based on the symbol of the fetched slope information SLP. In this case, since positive slope information is outputted at the time point when the waveform value W for the maximum value $P_1$ is outputted, the micro-computer 401 sets the value of the peak information B/T to one corresponding to a maximum value. The micro-computer 401 then designates the peak address ADR2 (in this case ADR2=0) as fetched from the peak address counter 523, as the write address ADR3, and writes the waveform value W, the waveform address ADR1 corresponding to the waveform value W, the peak classification B/T, and the slope information SLP, into the peak information memory 525 as first peak information. In the case of writing the first peak information, since there is no peak information immediately prior to this, then the creation and writing of stroke information is not carried out.

Subsequently, on output of a waveform value W corresponding to the minimum point $P_2$ as shown in FIG. 48, from the low pass filter 502, a null cross detection pulse Z is outputted in a similar manner to the above, and the write address ADR1, waveform value W, peak address ADR2 (=1), and the slope information SLP (<0) are fetched by the micro-computer 401. Subsequently, the micro-computer 401 determines the peak classification B/T (in this case bottom B) based on the slope information SLP in a similar manner to the above. Moreover, the micro-computer 401 supplies an address that is one smaller than the peak address ADR2, to the peak information memory 525 as a read out address ADR3, and reads out the first written waveform value W. Then, the micro-computer 401 calculates the difference between the waveform value W fetched this time from the low pass filter 502, and the first waveform value W read from peak information memory 525, to obtain the stroke information STRK. The peak classification B/T, and stroke information STRK obtained in this way are written together with other information ADR1, W, slope information SLP, as second peak information, to, an area corresponding to the peak address ADR3=1 of the peak information memory 525. The subsequent operations for when the peak points $P_3$, $P_4$ etc. are detected, are carried out in a similar manner.

Then after the elapse of a predetermined period, the output by the micro-computer 401, of the waveform collection directive START is stopped, terminating collection of the waveform values W and peak information.

(a)-(2) Waveform Parameter Sampling

Prior to waveform parameter extraction, the micro-computer 401 carries out a process to specify information corresponding to waveforms of one wave length, for collecting the waveform parameters from amongst the various information stored in the peak information memory 525.

Initially the slope information SLP and stroke information STRK corresponding to respective peak points $P_1$, $P_2$ etc. are successively read out from the peak information memory 525. After this, stroke information corresponding to a positive slope (that is to say corresponding to slope information SLP with a positive value) is selected from amongst the respective stroke information STRK. Then, from amongst this stroke information, a predetermined number of higher rank stroke information having large values is further selected. After this, one corresponding to a middle values is selected from amongst the selected stroke information STRK, and the stroke information is obtained for the rising part of the pulse wave of one wave length portion which is to be subjected to waveform parameter extraction, for example the rising portion indicated by symbol STRKM in FIG. 48. Subsequently the peak address one prior to the peak address of the said stroke information is obtained. That is to say, the peak address of the start point $P_6$ of the pulse wave of the one wave length portion which is to be subjected to waveform parameter extraction.

Next the micro-computer 401 refers to the respective peak information in the peak information memory 525, which corresponds to the pulse wave of one wave length portion, and computes respective peak information for substitution into the beforementioned computational equations (51)~(54). For example the following information.

$y_1$: $y_1$ is the waveform value $y_1$ corresponding to peak point $P_7$.

$T_1$: $T_1$ is calculated by subtracting the waveform address corresponding to peak point $P_6$ from the waveform address corresponding to peak point $P_7$, and multiplying the result by the period of the sampling clock Ø.

$T_4$~$T_6$: $T_4$~$T_6$ are calculated in a similar manner to $T_1$, based on the difference between the waveform addresses of the respective peak points.

The respective parameters obtained in this way are stored in the buffer memory.

(b) Manual Directive Mode

With the diagnostic apparatus (ii), it is possible to set a manual directive mode (a) using keyboard 402 operation, in addition to the above automatic diagnosis mode. When this manual directive mode is set, the examiner can designate by operation of a mouse, the peak points of the pulse waves necessary for the calculations of the waveform parameters. That is to say, according to the following.

In the manual directive mode, after outputting the waveform collection directive START for a predetermined time, the micro-computer 401 outputs a manual mode signal MAN. Then, read addresses ADR4 increasing successively from "0" are output by the micro-computer 401, and supplied to the waveform memory 503 by way of the selector 512. Radial pulse waveforms stored in the waveform memory 503 are thus read out and displayed on the display device 404.

Through operation of the mouse 413, the examiner moves the cursor position on the display device 404, and successively indicates the first point and last point of the pulse wave, and the various maximum and minimum points of the pulse wave with a click input. The micro-computer 401 detects the mouse operation, reads from the waveform memory 503 digital signals corresponding to the first point and last point, and the respective maximum and minimum points of the pulse wave designated by the examiner, and extracts the necessary waveform parameters (see the above equation (52) and (53)) from the read out information, and stores these in the buffer memory.

(c) Psychosomatic Fatigue Level Input

On completion of the waveform parameter collection through either of the above (a) or (b) mode, the micro-computer 401 displays the psychosomatic fatigue level diagnostic questionnaire shown in FIG. 43 on the display device 404 in accordance with the keyboard or mouse directive of the examiner. The examiner then makes a question diagnosis of the examinee corresponding to the displayed questions diagnosis table, and inputs the examinees response to the micro-computer 401 by mouse 413 operation. Here the question diagnosis may be a dialogue form of input. That is to say, each question on the diagnostic questionnaire is displayed one at time, or outputted as a voice, and the answer corresponding to this can take the format of examinee input by a keyboard or the like, to the micro-computer 401. The micro-computer 401 calculates the psychosomatic fatigue level on the basis of the input answers, and writes the result into the buffer memory.

All of the information necessary for this stress evaluation is arranged in the buffer memory as above. The micro-computer 401 makes a stress level diagnosis based on the information stored in the buffer memory, and thereafter the results are outputted and stored under the directive of the examiner in a similar manner to the apparatus (i) in explained in Chapter 4-1.

Chapter 4-3: Diagnostic Apparatus (iii)

Figure 49:
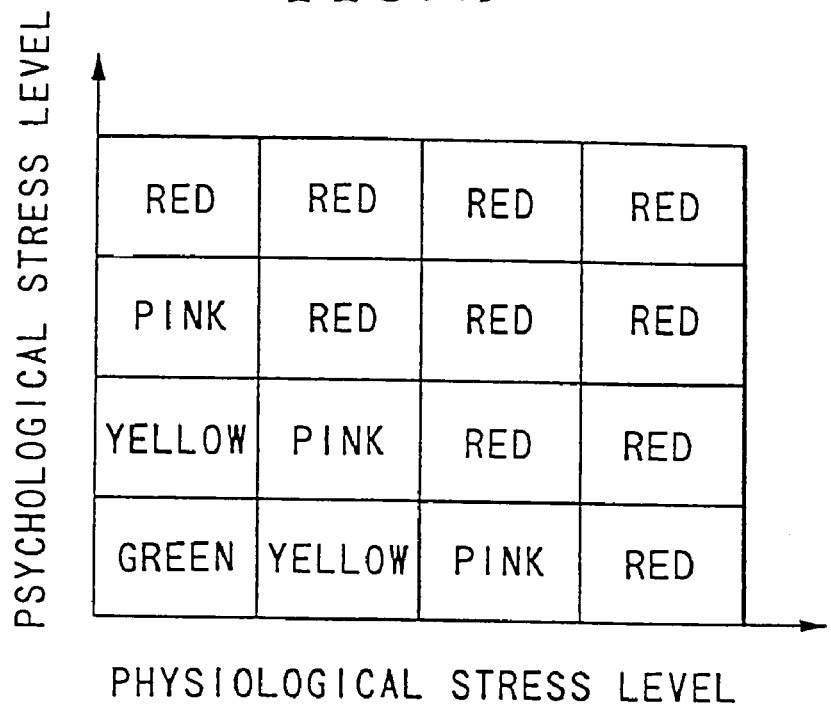
FIG. 49 is a display of stress level evaluated by a third variation of a stress level evaluation apparatus.

Next is a description of a diagnostic apparatus (iii). This stress level diagnostic apparatus has a color display device (not shown in the figure) as a stress level display means, in addition to the construction to the apparatus (ii) explained in Chapter 4-2. The micro-computer 401 in this apparatus, after calculating the physiological stress level and the psychological stress level, determines the display color according to the illustrated table of FIG. 49, and displays this on the color display unit.

The physiological stress level, psychological stress level and physiological age are obtained and these may be color displayed. In this case, rather than the two dimensional table shown in FIG. 49, a three dimensional display defining colors corresponding to the respective combinations of physiological stress level, psychological stress level and physiological age, can be used to determine the display color.

With the present apparatus, the combined stress levels of the physiological stress level and psychological stress level are indicated by the display color of the color display device. Hence even the general public, who have no judgment basis with respect to numerical values of stress level, can easily confirm their own stress level.

With the above apparatus, the examinee can use it as an automatic system for diagnosing his/her own stress level, without the need for a examiner such as a doctor.

Chapter 4-4: Variation of the Fourth Embodiment

The fourth embodiment is not limited to the above diagnostic apparatuses (i) to (ii). For example, a number of variations such as given below are also possible.

Apparatus (iv)

With the above apparatuses, both the waveform parameter and the psychosomatic fatigue level are used as parameters, and both the physiological stress and the psychological stress diagnosis performed. However, it is also possible to have a construction wherein only the physiological stress or physiological age are evaluated based on only the waveform parameter according to equation (51) or equation (54). In this case, since the effort of input of the psychosomatic fatigue level is omitted, use of the apparatus is simplified.

Apparatus (v)

In the above respective apparatuses, the stress level is performed of diagnosis on the basis of the examinees radial arterial pulse wave. However, the arterial pulse wave can be measured at locations from the radial portion to the finger portion, and the stress level diagnosis performed on the basis of this arterial pulse wave.

Apparatus (vi)

In the above apparatus (iii), a structure was adopted wherein the stress level etc. was made visible by means of display colors. However, the stress level display means is not limited to this. For apparatus, in a situation wherein the examinee recognizes the stress level in a visual sense, the stress level may be represented by the shading of the display color. It is also possible to display character information describing the stress level. Moreover, the display is not limited to visual methods of expression, and it may be possible to have a method wherein the stress level is expressed by appealing to a sense of hearing. For example, the pitch, volume, and tone of the sound may be changed depending on the stress level etc., and played to the examinee. Also, a voice output explaining the evaluation results of the stress level etc. is possible. Music may be provided corresponding to the stress level. etc., such as bright music when the stress level is low and gloomy music when the stress level is high.

In Chapter 4, the apparatus for performing diagnosis for the stress level and the physiological age were presented. Utilizing the method used in the above apparatus, a diagnostic apparatus for other subjects can be structured.

In this case, the waveform parameters which have the highest correlation for the diagnostic subject may be used. For example, the dynamic circulatory parameters described in Chapter 2, the pulse waveform spectrum described in Chapter 1, and so on, may be used as waveform parameters.

The means for obtaining the waveform parameter used to diagnose is not limit to the above apparatuses, and may be selected so as to be favorable to obtaining required parameter.

For example, there are the two methods to obtain the circulatory dynamic parameters; using the electrical model in Chapter 2, and computing the distortion factor of pulse waveform in Chapter 3. Either of the two methods may be favorably selected by considering the operational speed, accuracy, and so like for requirement.

As explained, diagnosis for the stress level can be accurately performed considering the psychosomatic fatigue level. Similarly, there are cases when a diagnosis may be more accurately performed by the taking the conscious symptom of the examinee into consideration. In this case, by adding inputting means for inputting conscious symptoms in the diagnostic apparatus, diagnosis may be performed based on both the inputted conscious symptom and waveform parameter of the pulse wave.

Moreover, depending on the diagnostic subjects, there are cases when it is wanted not only simply the name of disease but also the seriousness of the disease and outputting the computed degree. In such a case, using visual data (color, density, character and so on) and/or the audio data (music, voice and so on), diagnostic apparatus may express and output the degree of seriousness of the disease (stress level in the diagnostic apparatus of the fourth embodiment). Diagnosis for each predetermined period my depends on the diagnosis contents.

Chapter 5: Pulse Wave Analyzing Apparatus for Analyzing Spectrum of Pulse Waves

Recently, pulse diagnosis has come to the public attention, resulting in intensified research to explore the health condition of the body based on pulse waves. As general waveform analyzing techniques, there are techniques such as the FFT frequency analysis technique, and pulse wave analysis using this type of frequency analyzing technique is under investigation.

A pulse waveform is not the same shape for all pulses, and changes moment by moment. Moreover, the wavelength of each pulse wave is not constant. A technique has been considered wherein a pulse wave having such chaotic (random) behavior is considered as a waveform having an extremely long period, and subjecting it to a Fourier transformation. With such a technique, a detailed waveform spectrum can be obtained, however since the amount of computation becomes immense, the technique is not suited for use in rapidly obtaining the spectrum of pulse waves occurring moment by moment. If wave parameters representing the characteristics of the separate waves making up the pulse wave can be obtained continuously, then a much greater amount of information relating to a living body can be obtained. However a device to meet such requirements is presently not available.

Therefore, the one of objectives is to provide an apparatus for analyzing the characteristic of each individual pulse waves rapidly. Furthermore, the fifth embodiment enables higher performance to be achieved in the various apparatuses presented in Chapter 1 to 5.

In the following, the pulse wave analysis apparatus according to the fifth embodiment will be explained.

Chapter 5-1: Pulse Wave Analyzer (i)

This analyzer performs computation of spectrum of pulse waves for each pulsation.

Chapter 5-1-1: Structure of the Analyzer (i)

Figure 50:
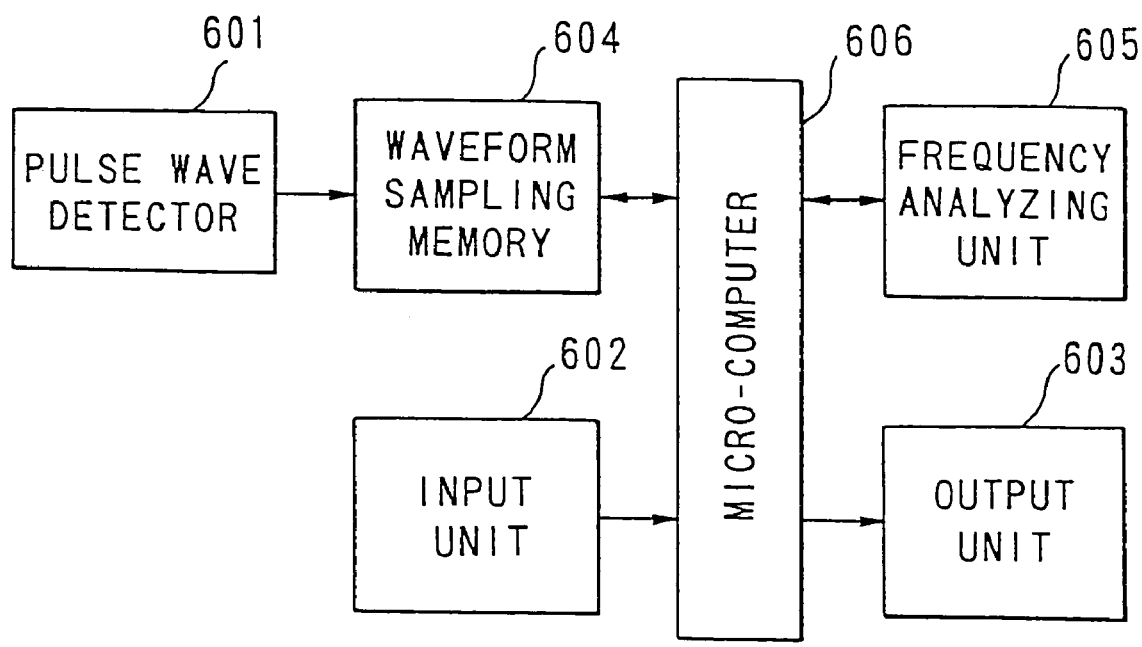
FIG. 50 is a block diagram showing a structure of a pulse wave analyzing apparatus according to a fifth embodiment of the present invention.

FIG. 50 shows the structure of a pulse wave analyzer according to the fifth embodiment of the present invention. As is shown in the FIG. 50, the pulse wave analyzer comprises a pulse wave detector 601, an input unit 602, an output unit 603, a waveform sampling memory 604, a frequency analyzing unit 605 and a micro-computer 606 which controls all of these.

The pulse wave detector 601 comprises a strain gauge or the like, which can be pressed against an examinee's radial artery to detect the pressure, and output this as a pulse wave signal (analog signal). The input unit 602 is a device provided for command input such as a keyboard to the micro-computer 606. The output unit 603 comprises a printer, display devices and other. These devices come under the control of the micro-computer 606 and store, display etc. the pulse wave spectrum obtained from the examinee. The waveform sampling memory 604, under control of the micro-computer 606, successively records the waveform signals output from the pulse wave detector 601, and also extracts and stores information showing the change points in the pulse wave signal, that is to say the point of change from a pulse wave corresponding to one pulse to the pulse wave corresponding to the next pulse. The detail structure of the waveform sampling memory 604 is same as the structure of the waveform sampling section 412.

Figure 51:
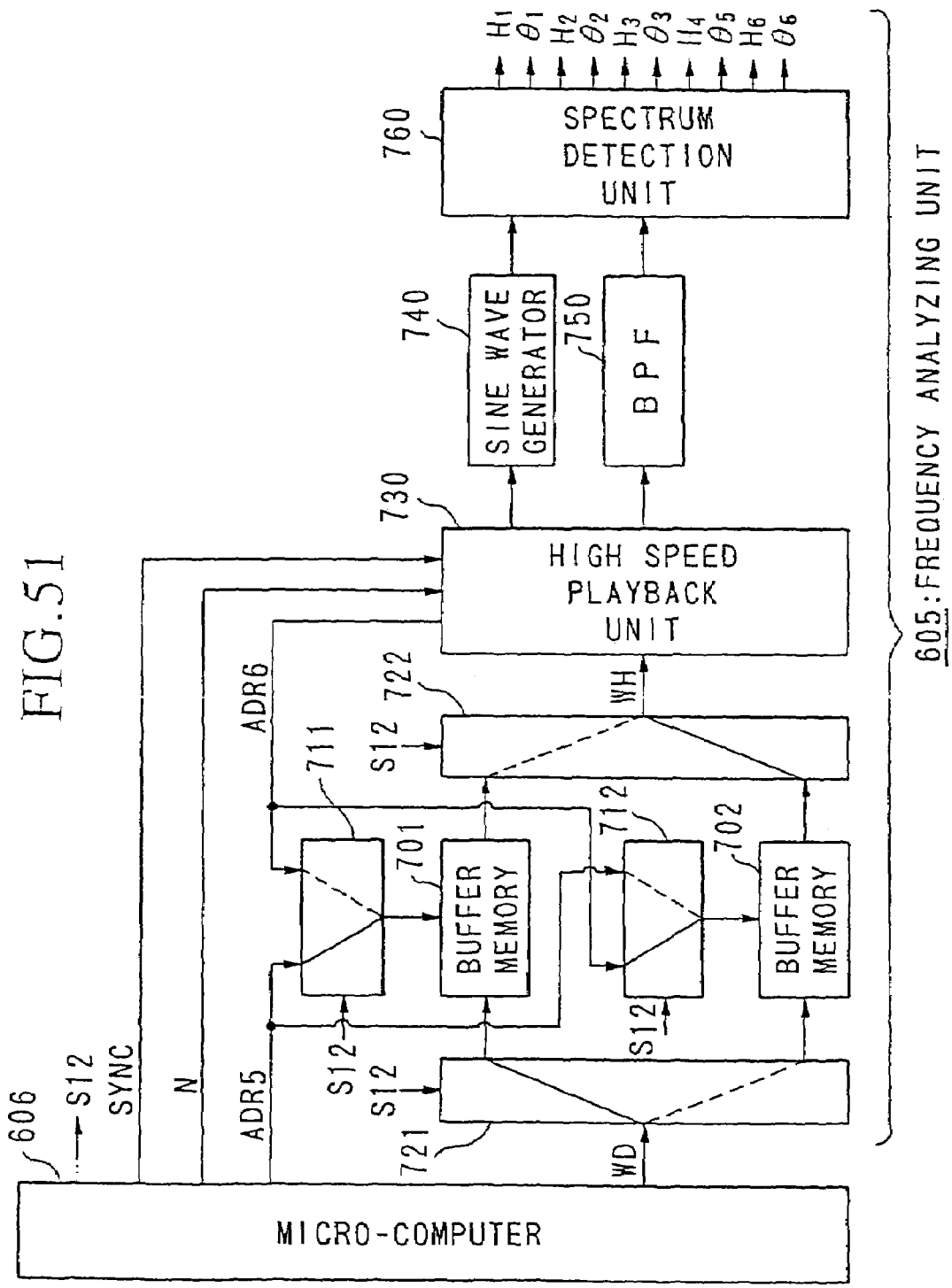
FIG. 51 is a block diagram showing the structure of frequency analyzing unit in the embodiment.

The frequency analyzing unit 605 gives a repeating high speed playback of the pulse wave signal stored in the waveform sampling memory 604, for each pulsation, and obtains and outputs the spectrum making up the pulse wave for each pulsation. FIG. 51 shows details of the construction. The pulse wave spectrum for each respective pulsation obtained from the frequency analyzing unit 605, is fetched by the micro-computer 606 and outputted from the output unit 603.

Chapter 5-1-1-1: Structure of the Waveform Sampling Memory 604

The waveform sampling memory 604 may use the parameter sampling section 412 with its signals and information shown in FIG. 46. The explanation of the waveform sampling memory 604 is omitted to avoid duplication. It is maintained that the manual output mode signal MAN shown is replaced with the select signal S11, and the numeral 401 is replaced with 606 for the micro-computer.

Chapter 5-1-1-2: Structure of the Frequency Analyzing Unit 605

Next is a detailed description of the construction of the frequency analyzing unit 605, with reference to FIG. 51. The frequency analyzing unit 605 receives, a waveform value WD for a pulse wave from the waveform memory 503 in the waveform sampling memory 604, by way of the micro-computer 606. The received waveform value WD is repeatedly played back at high speed, and the frequencies are analyzed for each pulse to compute spectrums for the pulse waves. Moreover, the frequency analyzing unit 605 serially computes respective spectrums which construct the pulse waves, in the order of an initial basic spectrum of the pulse wave, following by the second harmonic wave spectrum, and so on.

When the first waveform value WD for the waveform of one pulse component is output to the frequency analyzing unit 605, the micro-computer 606 outputs a synchronizing signal SYNC and an integer N of the waveform value WD which is included in that pulse, and changes the select signal S12. Furthermore, during the output of the waveform value WD for one pulse component, the micro-computer 606 successively outputs write addresses ADR5 changing from "0" through to "N-1", synchronously with the transfer of the respective waveform values WD.

Buffer memories 201, and, 202 are provided for storing the waveform values WD outputted from the micro-computer 606. A distributor 721 takes a waveform value WD for a pulse wave from the sampling memory 604 supplied via the micro-computer 606, and outputs this to one of buffer memory 701 or 702 as designated by a select signal S12. Furthermore, a selector 722 selects from the buffer memories 201, 202, the buffer memory designated by the select signal S2, and a waveform value WH read from the selected buffer memory is outputted to the high speed playback unit 730 (to be described later). Selectors 711 and 712 select the write addresses ADR5, or the read addresses ADR6 (to be mentioned later) generated by the high speed playback unit 730, according to the select-signal S12, so that each is supplied to the respective buffer memory 701 and 702.

By switching control the above described distributor 721, selector 722, and 701 and 702 on the basis of the select signal S12, data is read from the buffer memory 702 and supplied to the high speed playback unit 730, while writing data to buffer memory 701 and while writing data to the buffer memory 702, data is read from the buffer memory 701 and supplied to the high speed playback unit 730.

The high speed playback unit 730 is a means for reading from the buffer memories 701 and 702 the waveform values corresponding to the respective pulses. The read addresses ADR6 are changed in the range from "0" to "N-1" (where N is the number of waveforms to be read). More specifically, the high speed playback unit 730 generates read addresses ADR6 during the period when each waveform value WD corresponding to a certain pulse is being written to one buffer memory, and repeatedly reads over a number of times from the other buffer memory, all the waveform values WD corresponding to the pulse before that pulse. At this time, the generation of the read addresses ADR6 is controlled so that all of the waveform values WD corresponding to one pulse are read out normally within one fixed period. The period for reading all of the waveform values for one pulse is changed to correspond to the level of the spectrum to be detected, with a change to T when a basic wave spectrum is detected, a change to 2T for a second harmonic spectrum, a change to 3T for a third harmonic spectrum, and so on. Moreover, the high speed playback unit 730 has an internal interpolator which interpolates the waveform values WH read from the buffer memory 701 or 702, and outputs this as a waveform value of a predetermined sampling frequency m/T (m is a predetermined integer).

A band pass filter 750 is a filter having a central frequency of a predetermined value 1/T. A sine wave generator 740 is a variable frequency waveform generator and comes under control of the micro-computer 606. It sequentially outputs respective sign waves of periods T, 2T, 3T, 4T, 5T and 6T corresponding to the spectrum level to be detected. A spectrum detection unit 760 detects respective pulse amplitudes $H_1$ to $H_6$ of each spectrum of the pulse wave, on the basis of the output signal level from the band pass filter 750, and detects the respective spectrum phases $\theta_1$ to $\theta_6$ on the basis of the difference between the phase of the band pass filter 750 output signal and the phase of the sine wave output by the sine wave generator 740.

Chapter 5-1-2: Operation of the Analyzer (i)

The following is a description of the operation of the present embodiment shown in FIGS. 46, 50 and 51.

Initially, on input of a frequency analysis start command from the input unit 602, a waveform collection directive START is outputted by the micro-computer 606, and the waveform address counter 511 and the peak address counter 523 the inside the waveform sampling memory 604 are reset.

(1) Waveform Division

As a result, the waveform address counter 511 starts counting the sampling clock f, and the waveform sampling memory 604 carries out in a similar manner of the waveform section 412 explained at the index (a)-(1) in Chapter 4-2-2.

In other words, the waveform values W output in this way are supplied sequentially to the waveform memory 503, and written to a memory area designated by the waveform address ADR1 at that time point $P_1$ to $P_3$.

In this analyzer, when the STRK is above a predetermined value, or more specifically, when the STRK is considered sufficiently close to correspond to that for the rising portion of the pulse wave (STRKM in FIG. 48), then the micro-computer 606 reads the waveform address for the minimum value stroke start point (STRKM start point $P_6$ in FIG. 48) from the peak information memory 525, and writes this to the internal shift register. The subsequent operations for when the peak points $P_3$, $P_4$ etc. are detected, are carried out in a similar manner.

(2) Wave Shape Transfer

In parallel with the above operation, the micro-computer 606 successively reads the waveform values from the waveform memory 503 inside the waveform sampling memory 604, and transfers these to the frequency analyzing unit 605 as waveform data WD. The operation is described below with reference to FIGS. 52 and 53.

Figure 53:
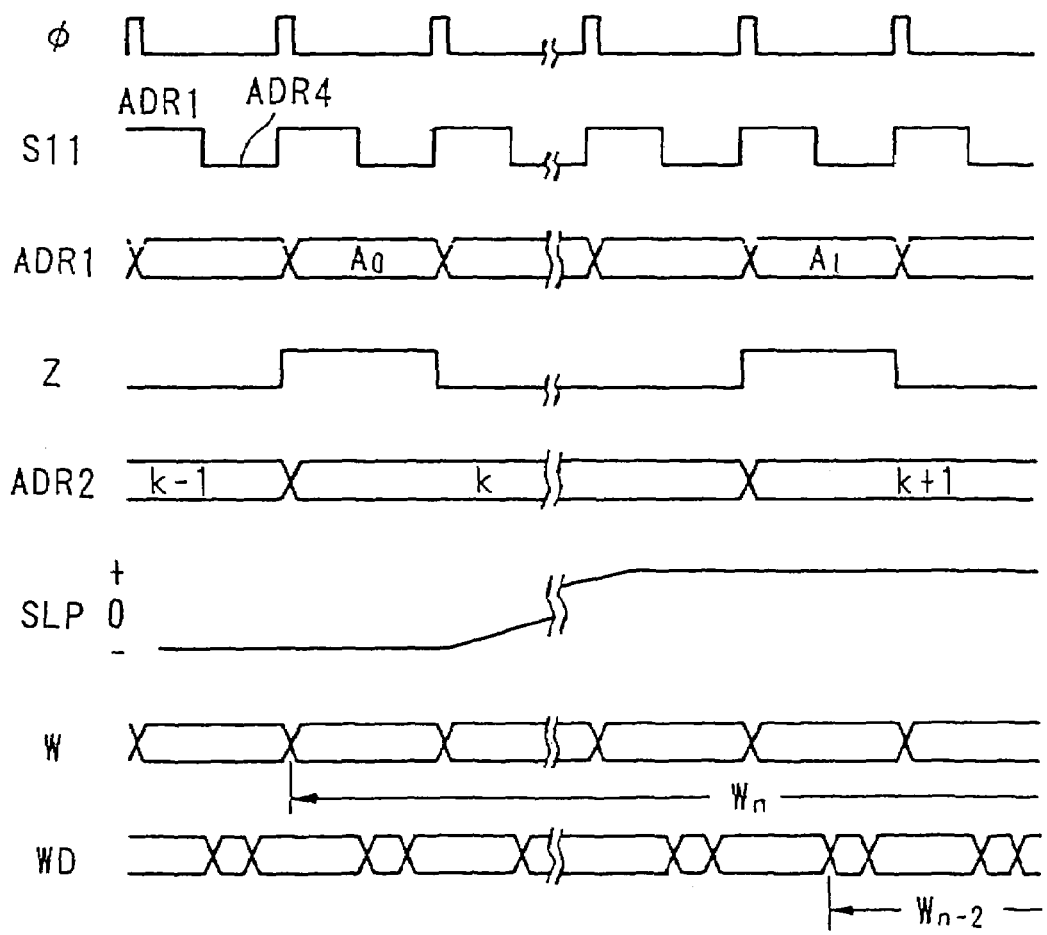
FIG. 53 is a timing chart showing an operation inside the waveform sampling memory.

As shown in FIG. 53, the select signal S11 is changed synchronously with the clock phase, and the waveform memory 503 synchronously, carries out a mode switching between the write mode and read mode.

Figure 52:
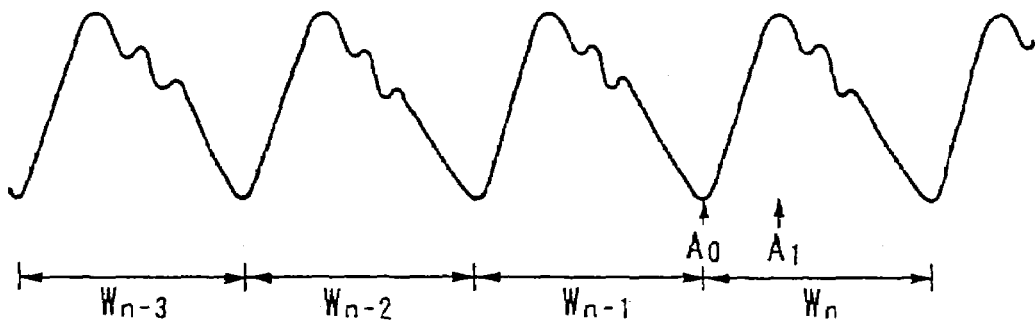
FIG. 52 is a diagram illustrating waveform transfer timing from a waveform sampling memory to a frequency analyzing unit.

In FIG. 52, when the waveform value of the pulse wave $W_n$ of one pulse portion corresponding to a certain pulsation, is inputted to the waveform memory 503, then at first the null cross detection signal Z is generated at the time point of input of the initial minimum value of the pulse wave corresponding to the pulse. That waveform address ADR1=$A_0$ is written to the peak information memory 525 (see FIG. 53). After this, on input of the maximum value (address $A_1$) into the waveform sampling memory 604, again a null cross detection signal Z is generated (see FIG. 53). When the stroke between the maximum value and the immediately preceding minimum value (address $A_0$) is above a predetermined value, the address $A_0$ of the minimum value is written to the shift resistor (not shown in the figure) inside the micro-computer 606. The waveform address written in this way, is then outputted from the shift resistor with a delay equivalent to two pulsations, and fetched to the micro-computer 606 as the initial address of the waveform value WD of the one pulse portion to be transferred to the frequency analyzing unit 605. That is to say, in FIG. 52, on writing the address $W_n$ of the maximum value of the pulse wave $W_N$ corresponding to the certain pulsation, into the shift register, the starting address of the pulse wave $W_{n-2}$ read into the same shift resistor two pulses earlier (address of the first maximum value), is outputted from the shift register, and detected by the micro-computer 606.

At this time point, the micro-computer 606 refers to the contents of the shift register and obtains the difference amount, from the waveform address for the first minimum value of the pulse wave $W_{n-2}$ until the address of the first minimum value of the next pulse wave $W_{n-1}$. That is to say the number N of waveform values included in the pulse wave $W_{n-1}$ of the single pulse portion is obtained. This is then outputted together with the synchronizing signal SYNC to the frequency analyzing unit 605. Moreover, the internal connection conditions of the distributor 721, selector 711 and 712, and selector 721 are changed, for example to the solid line conditions in FIG. 51, by changing the select signal S12 which is synchronized with the synchronizing signal SYNC.

Subsequently, the micro-computer 606 successively increases the read address ADR4 from the waveform address of the first minimum value of the pulse wave $W_{n-2}$, and supplies this to the waveform memory 503 by way of the selector 512. Here the read address ADR4 is changed at a faster speed (for example two times the speed) than is the write address ADR1. This is so that all the waveform values corresponding to the pulse wave $W_{n-2}$ which is prior to the pulse wave $W_{n-1}$, can be read out before the maximum value of the pulse wave $W_{n+1}$ of the pulse after the pulse wave $W_n$ is input to the waveform sampling memory 604. In parallel with the storage of the pulse wave $W_n$ in the waveform memory 503, the micro-computer 606 reads the waveform value WD for the pulse wave $W_{n-2}$ two pulses prior, from the waveform memory 503, and transfers these values to the frequency analyzing unit 605, and successively supplies the values to the buffer memory 701 by way of the distributor 721. The write address ADR5 is successively increased from "0" to "N-1", synchronously while the waveform values WD are successively supplied to the buffer memory 701, and these write addresses ADR5 are supplied to the buffer memory 701 by way of the selector 711. As a result, the respective waveform values WD corresponding to the pulse wave $W_{n-2}$, are stored in the respective storage areas for the addresses "0" to "N-1", in the buffer memory 701.

(3) High Speed Playback

In parallel with the above operation, the high speed playback unit 730 outputs the read addresses ADR6, and supplies these to the buffer memory 702 by way, of the selector 712.

As a result, the respective waveform values WD corresponding to the pulse wave $W_{n-3}$ one pulse prior to the pulse wave $W_{n-2}$ are read out from the buffer memory 702, and fetched to the high speed playback unit 730 by way of the selector 722.

Figure 54:
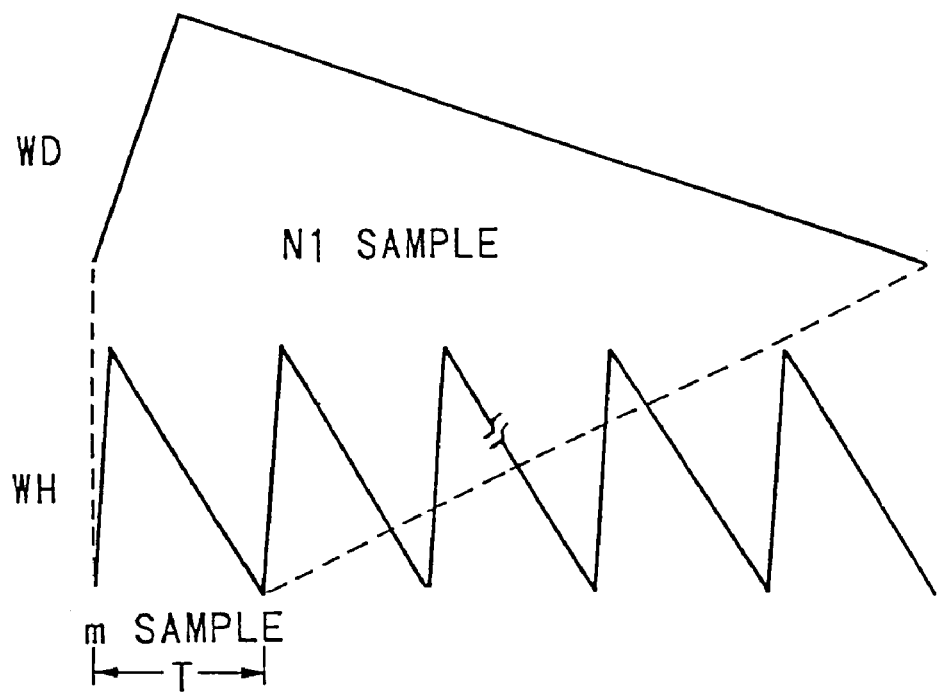
FIG. 54 is a diagram explaining an operation of a high speed playback unit.
Figure 55:
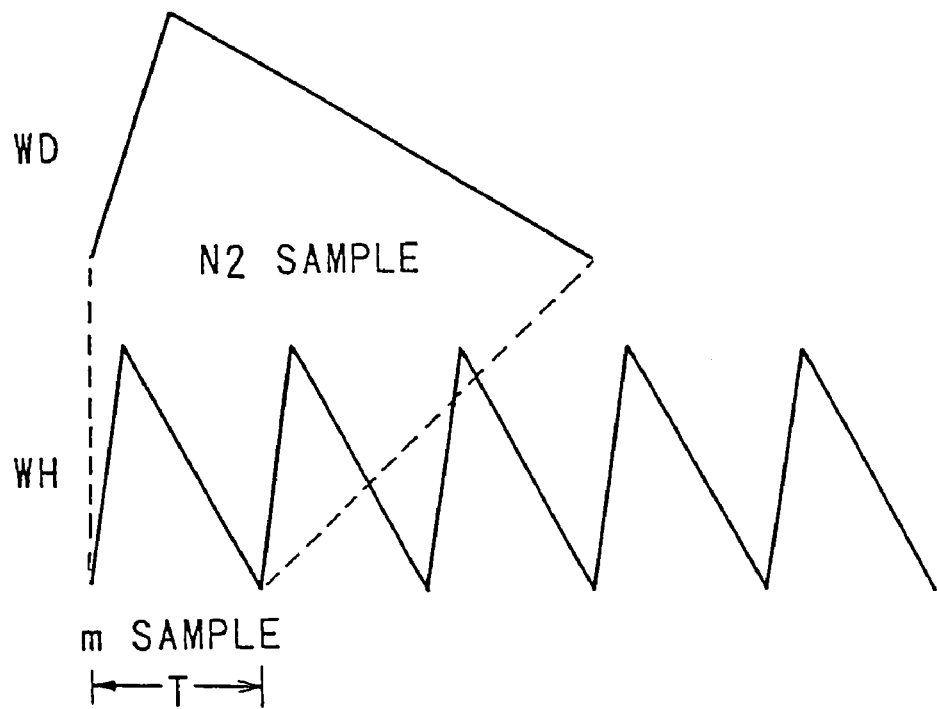
FIG. 55 is a diagram explaining the operation of the high speed playback unit.

Here, the respective waveform values WD corresponding to the pulse wave $W_{n-3}$ inside the buffer memory 702, are repeatedly read over a plurality of cycles at a higher speed than the speed at which the respective waveform values corresponding to the pulse wave $W_{n-2}$ are stored in the buffer memory 701. At this time, the incrementing speed of the read address ADR6 is controlled so that the waveform values WD1 corresponding to the pulse wave $W_{n-3}$ are all read out within a specified period T. That is to say, the high speed playback unit 730 increments the read address ADR6 at a higher speed when the number of waveform values WD to be read from the buffer memory 702 has a large N1 value as shown in FIG. 54. On the other hand, in the case of a small N2 value as shown in FIG. 55, the read address ADR6 is incremented at a slower speed, so that the read address ADR6 changes the "0" to "N1-1" or "0" to "N2-1" segment within the specified period T. The waveform value WD successively read out in this way is subject to an interpolation operation in the high speed playback unit 730, and on attaining a waveform value WH of a specified sampling frequency m/T, is supplied to the band pass filter 750.

(4) Spectrum Detector

Figure 56:
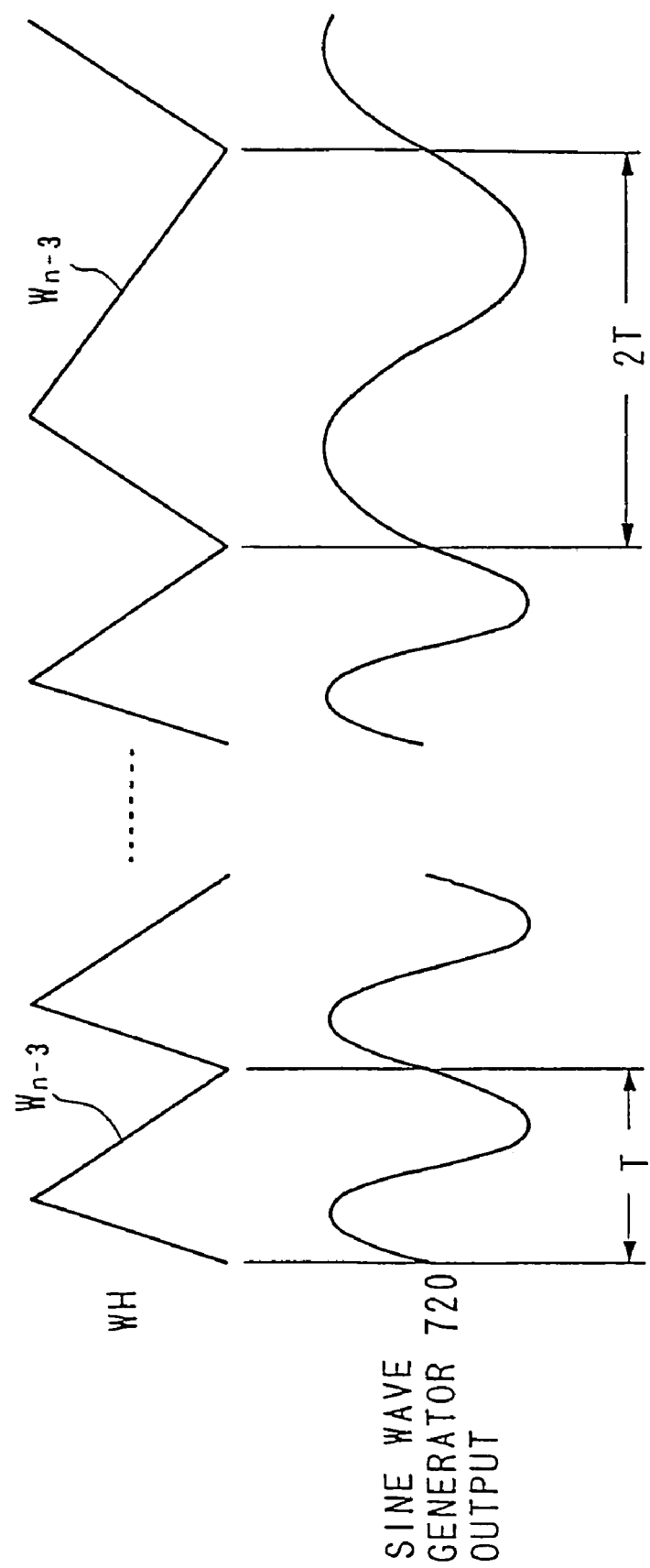
FIG. 56 is a diagram explaining the operation of the high speed playback, and a sine wave generator.

The band pass filter 750 selects and passes a signal of frequency 1/T from the time series data for the waveform WH, and supplies this to the spectrum detection unit 760. On the other hand, the sine wave generator 740 generates a sine wave having a period T as shown in FIG. 56, and supplies this to the spectrum detection unit 760. The spectrum detection unit 760 detects the output signal level from the band pass filter 750 over several waves, and outputs a representative value as the basic wave spectrum amplitude $H_1$ of the pulse wave $W_{n-3}$. It also detects the phase difference between the output signal phase of the band pass filter 750, and the output sine wave phase from the sine wave generator 740 over several waves, and outputs the representative value as the basic wave spectrum phase $q_1$ for the pulse wave $W_{n-3}$. From these respective representatives values, are calculated for example the output signal level corresponding to the respective waves immediately before output of the basic wave spectrum, and the mean movement value of the phase difference.

Next, the high speed playback unit 730 sets the incrementing speed of the read address ADR6 to ½ in the case of basic wave spectrum detection, so as to read all of the waveform values for the pulse wave $W_{n-3}$ within the specified period 2T. It also repeatedly reads out the waveform values WH corresponding to the pulse wave $W_{n-3}$, and supplies these to the band pass filter 750 (see FIG. 56). Then a signal of frequency 1/T, in the time scale data constituting the waveform value WH, that is to say the signal corresponding to the second harmonic of the pulse wave $W_{n-3}$, is passed by the band pass filter 750, and supplied to the spectrum detection unit 760. As a result the amplitude $H_2$ of the second harmonic spectrum of the pulse wave $W_{n-3}$, is detected by the spectrum detection unit 760, and is outputted.

On the other hand, the sine wave generator 740 generates a sine wave having a period 2T, and supplies this to the spectrum detection unit 760 (see FIG. 56). As a result, the phase $q_2$ of the basic wave spectrum of the pulse wave $W_{n-3}$ is outputted by the spectrum detection unit 760.

After this, in the case of the basic wave spectrum, the increment speed of the read address ADR6 is successively changed as ⅓, ¼, ⅕, ⅙. The period of the sine wave generated by the sine wave generator 740 is also successively changed in conformity as 3T, 4T, 5T, 6T, and an operation similar to the above carried out. The amplitudes $H_3$ to $H_6$ and phases $q_3$ to $q_6$ of the 3rd to 6th harmonic spectrums, are output from the spectrum detection section 760. The respective spectrums for the pulse wave $W_{n-3}$ obtained in this way are fetched by the micro-computer 606.

The micro-computer 606 then computes the frequency:

$$f = \frac{1}{N \cdot \tau}$$

of the basic wave, using the number N of waveform values WD corresponding to the pulse wave $W_{n-3}$ and the period $\tau$ of the clock $\phi$, and outputs this together with the above-mentioned spectrum, from the output section 603.

Subsequently, the pulse wave $W_{n+1}$ one pulsation after the pulse wave $W_n$, rises, and on input of the initial maximum value into the waveform sampling memory 604, the micro-computer 606 generates a synchronized signal SYNC and outputs the number N of the waveform values WD included in the pulse wave $W_{n-2}$. Furthermore, the select signal S12 is inverted so that the internal connection conditions in the distributor 721, selectors 711 and 712, and selector 721 become those shown by the broken line in FIG. 51. Moreover, in parallel with storage of the pulse wave $W_{n+1}$ in the waveform memory 503, the micro-computer 606 reads from the waveform memory 503, the waveform values WD for the pulse wave $W_{n-1}$ two pulses prior, and transfers these to the frequency analyzing unit 605, and successively supplies them to the buffer memory 702 by way of the distributor 721. On the other hand, in parallel with this operation, the high speed playback unit 730 reads from the buffer memory 701, the respective waveform values WD corresponding to the pulse wave $W_{n-2}$ one pulsation prior to the pulse wave $W_{n-1}$, and then outputs these as waveform values WH after interpolation by the high speed playback unit 730. A similar processing to that for pulse wave $W_{n-3}$, is then carried out on the waveform values WH corresponding to the pulse wave $W_{n-2}$, and the spectrum obtained.

Subsequently, the successively arriving respective pulse waves are processed in a similar manner to the above, and the spectrums for the respective pulse waves are obtained in succession and are outputted from the output unit 603, as waveform parameters corresponding to the individual pulses.

Chapter 5-2: Pulse Wave Analyzer (ii)

In the analyzer (i) explained in Chapter 5-1, the waveform data stored in the waveform memory 503, was played backed as pulsations and the pulse wave spectrum computed for each pulsation. In contrast to this, with the present analyzer (ii), a technique is used such as that proposed by the present inventor in Chapter 2. With this technique, the values for respective elements of the electrical model, modeled on the arterial system dynamics of an examinee, are obtained on the basis of the pulse waves obtained from the examinee, and the results used as condition indicating parameters.

The Model considers four parameters of the factors deciding the behavior of the human circulatory arterial system; namely the moment due to the blood flow in the arterial system proximal section, the vascular resistance due to the blood viscosity in the proximal section, the compliance of the blood vessels (viscous elasticity) at the proximal section, and the vascular resistance at the distal section, and models these four parameters as an electrical model. The details of the model have described in Chapter 2-1.

In the present analyzer (ii), the micro-computer 606 by way of the selector 722, successively writes to one of the buffer memories 701, 702, the waveform data corresponding to the respective pulses, and reads from the other buffer memory which is not being written to, waveform data corresponding to one pulse. It then simulates the operation of the four parameter model at the time an electrical signal corresponding to the pressure wave at the arterial beginning section is applied thereto, estimates the values for the various parameters of the electrical model so as to output waveforms corresponding to the waveform data read from the buffer memory 701 or 702, and outputs the calculated results as waveform parameters. The values for the various parameters in the electrical model can be obtained through trial and error by changing the values for the parameters and repeating the simulation operation. However it is also possible to use the technique described in Chapter 2. Moreover, the dynamic circulatory parameters may be obtained from the distortion of the pulse waveform described in Chapter 3.

Chapter 5-3: Variation of the Fifth Embodiment

The fifth embodiment is not limited to the above analyzers (i) and (ii). For example, a number of variations such as given below are also possible.

Analyzer (iii)

In the above analyzer (i) described in Chapter 5-1, the frequency analysis of the pulse wave was carried out by hardware. However the present embodiment is not limited to this, and frequency analysis may be carried out with software executed by the micro-computer 606. Furthermore frequency analysis methods such as DFT (Discrete Fourier Transform), FFT (Fast Fourier Transform) and the like may be suitable.

Analyzer (iv)

In the above respective Analyzers (i) and (ii) described in Chapter 5-1 and 5-2, the waveform parameters corresponding to the respective pulsations were outputted in real time as they were each obtained. However the output method for the waveform parameters is not limited to this method. For example the micro-computer 606 can compute the mean sum value of the waveform parameters for a predetermined number of pulsations and output this. Moreover, the micro-computer 606 can calculate the mean sum value of the waveform parameters of the predetermined number of previous pulsations, that is to say, the, mean movement value of the waveform parameters, and output this in real time.

Analyzer (v)

In Chapter 5-1 and 5-2, the above respective analyzers (i) and (ii) for carrying out analysis of the radial pulse has been described. However the object of analysis of the present invention is not limited to only the radial pulse. For example it may also be applicable to fingertip pulse waves etc. and other types of pulse waves.

Analyzer (vi)

Many parameters apart from those given in the respective examples can be considered as waveform parameters of the pulse wave. When the pulse wave analyzer according to the present invention is used for diagnosis, the waveform parameters can be changed to obtain those suitable for the diagnosis. For example, in Chapter 4, the present inventor proposed an apparatus for obtaining an examinee's stress level based on the amplitude and phase of the peak points appearing in the pulse wave. With the apparatus according to the above embodiment, information related to the peak points can be obtained from the pulse waves corresponding to each pulse, and used for evaluation of stress levels.

In the present invention, the living body refers to the body of the examinee to be subjected to diagnosis or analysis, but the living body is not necessarily limited only to a human body. The basic principle outlined in the present invention should be equally applicable to animal bodies.

Furthermore, the present invention is not limited by the embodiments presented in Chapter 1 to Chapter 5. Various other modifications or applications are possible within the principle of diagnosis based on detailed analyses of pulse waveforms.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulse wave analyzing apparatus comprising: p1 pulse wave detecting means for detecting a pulse waveform from a living body; and
   analyzing means for outputting at least one of peak point data or timing data of the pulse waveform detected by said pulse wave detecting means; and
   wherein the analyzing means comprises:
      differential means for differentiating the pulse waveform detected by the pulse wave detecting means;
      inflection detecting means for detecting a timing when an output from said differential means is "0";
      count means for counting a sampling clock; and
      means for outputting peak point data or timing data for waveform parameters on the basis of the count value counted by the count means and the amplitude of pulse waveform detected by the detecting means when the output from the differential means is "0".

2. A pulse wave analyzing apparatus in accordance with claim 1, wherein said living body is a living human body.

3. A pulse wave analyzing apparatus comprising:
   pulse wave detecting means for detecting a pulse waveform from a living body; and
   analyzing means for outputting at least one of peak point data or timing data of the pulse waveform detected by said pulse wave detecting means
   wherein said analyzing means comprises:
      display means for displaying the pulse waveform detected by said pulse wave detecting means;
      designating means for designating a peak point of the pulse waveform displayed in display means; and
      means for outputting peak point data or timing data for waveform parameters on the basis of the peak point designated by the designating means.

4. A pulse wave analyzing apparatus in accordance with claim 3, wherein said living body is a living human body.

5. A diagnostic apparatus comprising:
   analyzing means for creating waveform parameters from information representing a pulse wave of a living body; and
   diagnostic means for performing a diagnosis of a condition of the living body on the basis of the waveform parameters,
   wherein said analyzing, means outputs as waveform parameters, peak point data or timing data of the pulse wave obtained from the living body; and
   wherein said analyzing means comprises:
      differential means for differentiating the pulse waveform parameters;
      inflection detecting means for detecting a timing when an output from said differential means is "0"; and
      count means for counting a sampling clock; and
      means for outputting peak point data or timing data for the pulse waveform parameters on the basis of the count value counted by the count means and the amplitude of the pulse waveform parameters when the output from said differential means is "0".

6. A diagnostic apparatus as in claim 5, wherein the diagnostic means perform a diagnosis of a stress level of a living body.

7. A diagnostic apparatus as in claim 5, wherein the stress level is a physiological stress level.

8. A diagnostic apparatus as in claim 5, wherein the stress level is a psychological stress level.

9. A diagnostic apparatus as in claim 5, wherein the diagnostic means performs a diagnosis of a physiological age of said living body.

10. A diagnostic apparatus as in claim 5, further comprising an inputting means for inputting psychosomatic fatigue levels that are quantified as to the degree of matching with a patient having symptoms that are prominent at high stress levels, and wherein the diagnostic apparatus performs a diagnosis of stress level on the basis of both the waveform parameters and the psychosomatic fatigue levels.

11. A diagnostic apparatus as in claim 10, wherein said diagnostic means outputs a message asking the degree of matching with the patient having symptoms that are prominent at high stress levels, and further comprising interactive input means for receiving an answer to the message, and said psychosomatic fatigue level is computed on the basis of the answer received by the interactive input means.

12. A diagnostic apparatus as in claim 5, further comprising a reading means for reading out both psychosomatic fatigue levels that are quantified as to the degree of matching with a patient having symptoms that are prominent at high stress levels and the waveform parameters from a storage media, and wherein the diagnostic means performs a diagnosis on the basis of the read information.

13. A diagnostic apparatus comprising:
   analyzing means for creating waveform parameters from information representing a pulse wave of a living body; and
   diagnostic means for performing a diagnosis of a condition of the living body on the basis of the waveform parameters,
   wherein said analyzing means outputs as waveform parameters, peak point data or timing data of the pulse wave obtained from the living body; and
   wherein said analyzing means comprises:
      display means for displaying the pulse waveform parameters; and
      designating means for designating a peak point of the pulse waveform parameters displayed in the display means, and
      means for outputting peak point data or timing data for the waveform parameters on the basis of the peak point designated by the designating means.

14. A diagnostic apparatus as in claim 13, wherein the diagnostic means perform a diagnosis of a stress level of a living body.

15. A diagnostic apparatus as in claim 13, wherein the stress level is a physiological stress level.

16. A diagnostic apparatus as in claim 13, wherein the stress level is a psychological stress level.

17. A diagnostic apparatus as in claim 13, wherein the diagnostic means performs a diagnosis of a physiological age of said living body.

18. A diagnostic apparatus as in claim 13, further comprising an inputting means for inputting psychosomatic fatigue levels that are quantified as to the degree of matching with a patient having symptoms that are prominent at high stress levels, and wherein the diagnostic apparatus performs a diagnosis of stress level on the basis of both the waveform parameters and the psychosomatic fatigue levels.

19. A diagnostic apparatus as in claim 18, wherein said diagnostic means outputs a message asking the degree of matching with the patient having symptoms that are prominent at high stress levels, and further comprising interactive input means for receiving an answer to the message, and said psychosomatic fatigue level is computed on the basis of the answer received by the interactive input means.

20. A diagnostic apparatus as in claim 13, further comprising a reading means for reading out both psychosomatic fatigue levels that are quantified as to the degree of matching with a patient having symptoms that are prominent at high stress levels and the waveform parameters from a storage media, and wherein the diagnostic means performs a diagnosis on the basis of the read information.

* * * * *

UNITED STATES PATENT AND TRADEMARK OFFICE
CERTIFICATE OF CORRECTION

| | | |
|---|---|---|
| PATENT NO. | : 7,465,274 B2 | Page 1 of 1 |
| APPLICATION NO. | : 10/869587 | |
| DATED | : December 16, 2008 | |
| INVENTOR(S) | : Kazuhiko Amano et al. | |

It is certified that error appears in the above-identified patent and that said Letters Patent is hereby corrected as shown below:

<u>Column 47,</u>
Line 15, please delete "p1"

<u>Column 47,</u>
Line 57, please delete ","

Signed and Sealed this

Nineteenth Day of May, 2009

JOHN DOLL
*Acting Director of the United States Patent and Trademark Office*